(12) United States Patent
Kim et al.

(10) Patent No.: US 11,261,175 B2
(45) Date of Patent: Mar. 1, 2022

(54) FLUORENE DERIVATIVE OR PHARMACEUTICALLY ACCEPTABLE SALT THEREOF, PREPARATION METHOD THEREFOR, AND PHARMACEUTICAL COMPOSITION COMPRISING SAME AS EFFECTIVE INGREDIENT FOR PREVENTING OR TREATING HCV-RELATED DISEASE

(71) Applicants: Seoul National University R&DB Foundation, Seoul (KR); Postech Academy-Industry Foundation, Gyeongsangbuk-do (KR)

(72) Inventors: Byeong Moon Kim, Seoul (KR); Sung Key Jang, Gyeongsangbuk-do (KR); Young Su You, Seoul (KR); Il Hak Bae, Daegu (KR); Heejo Moon, Gyeonggi-do (KR); Byeong Wook Kim, Gyeongsangnam-do (KR); Hee Sun Kim, Jeollanam-do (KR); Jaegon Mun, Gyeongsangnam-do (KR)

(73) Assignees: Seoul National University R&DB Foundation, Seoul (KR); Postech Academy-Industry Foundation, Gyeongsangbuk-Do (KR)

(*) Notice: Subject to any disclaimer, the term of this patent is extended or adjusted under 35 U.S.C. 154(b) by 0 days.

(21) Appl. No.: 16/633,382

(22) PCT Filed: Sep. 20, 2018

(86) PCT No.: PCT/KR2018/011182
§ 371 (c)(1),
(2) Date: Jan. 23, 2020

(87) PCT Pub. No.: WO2019/059687
PCT Pub. Date: Mar. 28, 2019

(65) Prior Publication Data
US 2020/0231573 A1  Jul. 23, 2020

(30) Foreign Application Priority Data
Sep. 22, 2017 (KR) .................. 10-2017-0122791

(51) Int. Cl.
| | |
|---|---|
| *C07D 403/12* | (2006.01) |
| *A23L 33/10* | (2016.01) |
| *A61P 31/14* | (2006.01) |
| *C07D 403/14* | (2006.01) |
| *C07D 413/14* | (2006.01) |
| *C07D 491/113* | (2006.01) |
| *C07D 519/00* | (2006.01) |

(52) U.S. Cl.
CPC ............ *C07D 403/12* (2013.01); *A23L 33/10* (2016.08); *A61P 31/14* (2018.01); *C07D 403/14* (2013.01); *C07D 413/14* (2013.01); *C07D 491/113* (2013.01); *C07D 519/00* (2013.01)

(58) Field of Classification Search
CPC .. C07D 403/12; C07D 403/14; C07D 413/14; C07D 491/113; C07D 519/00; A61P 31/14
See application file for complete search history.

(56) References Cited

U.S. PATENT DOCUMENTS

| | | | | |
|---|---|---|---|---|
| 9,598,362 | B2* | 3/2017 | Jang .................. | C07K 5/06026 |
| 10,421,779 | B2* | 9/2019 | Keum ................ | C07K 5/06078 |
| 2015/0148386 | A1* | 5/2015 | Jang .................... | C07D 413/14 |
| | | | | 514/376 |
| 2016/0031810 | A1 | 2/2016 | Jang et al. ........... | C07D 207/16 |

FOREIGN PATENT DOCUMENTS

| | | |
|---|---|---|
| KR | 10-2015-0065130 | 6/2015 |
| WO | 2010/096462 | 8/2010 |
| WO | 2011/059763 | 5/2011 |
| WO | 2015/042375 | 3/2015 |
| WO | 2015/096674 | 7/2015 |
| WO | 2017/076201 | 5/2017 |

OTHER PUBLICATIONS

Kim; Antiviral Research 2020, 174, 1046782. (Year: 2020).*
World Health Organization, "Hepatitis C", Jul. 27, 2020. 6 pages. Downloaded Jun. 17, 2021 from https://www.who.int/news-room/fact-sheets/detail/hepatitis-c (Year: 2020).*
WO2017076201 Unverified Machine translation. Published May 11, 2017 in Chinese language. (Year: 2017).*
Link et al. "Discovery of Ledipasvir (GS-5885): A Potent, Once Daily Oral NS5A Inhibitor for the Treatment of Hepatitis C Virus Infection" Journal of Medicinal Chemistry 2014 57:2033-2046.
Zhong et al. "Potent bisimidazole-based HCV NS5A Inhibitors bearing annulated tricyclic motifs" Bioorganic & Medicinal Chemistry Letters 2014 24:5738-5742.
Alter, H.G. "Chronic Consequences of Non-A, Non-B Hepatitis" Current Pespective in Hepatology 1989 p. 83.

(Continued)

*Primary Examiner* — Daniel R Carcanague
(74) *Attorney, Agent, or Firm* — Licata & Tyrrell P.C.

(57) ABSTRACT

The present invention relates to a fluorene derivative or a pharmaceutically acceptable salt thereof, a preparation method therefor, and a pharmaceutical composition comprising the same as an effective ingredient for preventing or treating HCV-related disease. A fluorene derivative according to the present invention is identified to exhibit an antiviral performance against not only HCV, but also highly against HCV mutants, particularly double mutants and thus can be used in a pharmaceutical composition for prevention or treatment of HCV-caused liver disease, such as acute hepatitis C, chronic hepatitis C, liver cirrhosis, hepatocellular cancer, etc., particularly, liver disease caused by mutants of HCV. The derivative can be useful in a pharmaceutical composition for prevention or treatment of HCV-related liver disease by which the problem of resistant mutation against conventional therapeutic agents is solved.

12 Claims, No Drawings

(56) References Cited

OTHER PUBLICATIONS

Bae et al. "Novel Benzidine and diaminofluorene prolinamide derivatives as potent hepatitis C virus NS5A inhibitors" European Journal of Medicinal Chemistry 2015 101:163-178.
Davis et al. "Treatment of Chronic Hepatitis C with Recombinant Interferon Alfa" N Engl. J. Med. 1989 3211:1501-1506.
Hayashi, N. & Takahara, T. "Antiviral therapy for chronic hepatitis C: past; present, and future" J. Gastroenterol. 2006 41:17-27.
Kronenberger et al. "Novel Hapatitis C Drugs in Current Trials" Clin Liver Dis. 2008 12:529-555.
이진오 (Lee) et al. "Hepatitis C virus research trend" Korean Society for Biochemistry and Molecular Biology 2013 12 pages 107.
Li, G. & De Clercq, E. "Current therapy for chronic hepatitis C: The role of direct acting antivirals" Antiviral Research 2017 142:83-122.
Manns et el. "The way forward in HCV treatment—finding the right path" Nat. Rev. Drug. Discov. 2007 6:991-1000.
International Search Report in PCT/KR2018/011182 dated Jan. 8, 2019 with tranlation.

\* cited by examiner

FLUORENE DERIVATIVE OR PHARMACEUTICALLY ACCEPTABLE SALT THEREOF, PREPARATION METHOD THEREFOR, AND PHARMACEUTICAL COMPOSITION COMPRISING SAME AS EFFECTIVE INGREDIENT FOR PREVENTING OR TREATING HCV-RELATED DISEASE

This patent application is the National Stage of International Application No. PCT/KR2018/011182 filed Sep. 20, 2018, which claims the benefit of priority from Korean Application No. 10-2017-0122791, filed Sep. 22, 2017, each of which are herein incorporated by reference in their entirety.

BACKGROUND OF THE INVENTION

1. Field of the Invention

The present invention relates to a fluorene derivative or a pharmaceutically acceptable salt thereof, a preparation method therefor, and a pharmaceutical composition comprising the same as an effective ingredient for preventing or treating HCV-related disease.

2. Description of the Related Art

HCV (Hepatitis C Virus) is an enveloped virus that belongs to the Flavivirus family. HCV genome is (+)RNA (plus-strand RNA) in the size of 9.6 kb and expresses a poly-protein composed of 3,010 amino acids. The poly-protein is separated into three structural proteins and six nonstructural proteins by the host cell and virus enzymes.

At the 5' and 3' ends of the HCV genome, there are untranslated regions where the nucleotide sequences of almost all genotypes remain the same. 330-341 nucleotides have been recently found at the 5' end and 98 nucleotides have also been identified behind poly A at the 3' end, which are believed to play an important role in viral RNA replication or translation. Viral RNA produces viral structural proteins core, E1 and E2 after intracellular translation, and other regions produce nonstructural proteins. Structural proteins include core, E1 and E2, which form a viral envelope. These proteins are translated into a poly-protein and then separated by signal peptidase existing in ER (endoplasmic reticulum). Nonstructural proteins are separated by the serine protease NS3 and the cofactor NS4A. The separated nonstructural proteins play an important role in viral RNA replication, assembly and release. In particular, NS5B has RNA-dependent RNA polymerase function, and NS5A is an essential protein for viral gene replication and virus assembly.

HCV is a major human pathogen, and it is estimated that about 70 million people are infected with HCV worldwide. A high proportion of those people infected with HCV are confirmed to have a severe progressive liver disease including cirrhosis and hepatocellular carcinoma developed therefrom.

HCV infection is caused by transfusion and is community-acquired, and about 70% of HCV infection has been reported by renal dialysis. Once infected with HCV, acute hepatitis with cirrhosis is developed in about 20% of the infected people within 5 years, which progresses to liver cancer (non-patent reference 1 (Davis et al, New. Engl. J. Med., [0010] 321 (1989) 1501) and non-patent reference 2 (Alter et al, Leonard et al., Current Perspective in Hepatology, (1989) p. 83)). This high chronic infection rate is very rare in RNA virus, which is evidence that HCV is a key mediator to cause liver cancer with a high rate. Recently, all blood has been tested for HCV, so that infection caused by blood transfusion has been significantly reduced. However, community-acquired infection is not controlled effectively, and therefore the infection rate is high. Therefore, it is recognized as an important problem world-widely.

In addition, HCV is distributed evenly over the world, unlike hepatitis B virus (HBV), and it is reported that 0.5%~1% of the world population is infected with HCV. HCV infection characteristically progresses to chronic hepatitis. The probability of progress of HCV infection to cirrhosis and liver cancer is significantly higher than that of hepatitis B. Taxonomically, HCV belongs to a completely different virus family from hepatitis B virus (HBV). Therefore, it is not possible to prevent HCV with hepatitis B virus vaccine.

On the other hand, combination of interferon and ribavirin, the antiviral agents, is currently used to treat HCV infection (see non-patent reference 3 (Hayashi N., et al., J. Gastroenterol., 41, (2006), 17)), but response to those drugs is very different according to the genotype and the effect is very weak. Besides, these two drugs used in combination therapy cause serious side effects and are expensive. Therefore, it is requested to develop a novel efficient anti-HCV agent.

The anti-HCV agents studied so far in order to overcome the problems above characteristically express their pharmacological activity as anti-HCV drugs by blocking a certain stage of HCV life cycle, that is, virus replication and assembly.

The life cycle of HCV is as follows. Once attached on the surface of a host cell, HCV invades into the host cell by endocytosis. Then, a precursor protein consisting of about 3,000 amino acid residues is generated from RNA of the HCV introduced in the host cell. Thereafter, about 10 kinds of viral proteins such as capsid protein, envelope protein, NS3 and NS4 proteases, NS5A protein and NS5B RNA polymerase, etc, are generated by the interaction between HCV genome or host cell signal peptidase and encoded NS3 and NS4 proteases. The HCV RNA replicated by NS5B polymerase is assembled with a capsid protein and an envelope protein modified by α-glucosidase in ER, resulting in the formation of a virus particle. The HCV particles are then released from the host cell (see non-patent reference 4 (Manns M P., et al., Nat. Rev. Drug. Discov., 6, (2007), 991)).

Until recently, cultured cells could not be infected with HCV, and HCV could not be proliferated in cultured cells. In 1999, however, there was a limited achievement. A system was developed to replicate HCV RNA by transfecting a liver cancer cell line with the HCV RNA region encoding non-structural proteins, which is called HCV RNA replicon. The use of replicon has allowed in vitro screening of drugs that inhibit HCV proliferation (see non-patent reference 5 (Hepatitis C virus research trend, Journal of Biochemistry & Molecular Biology, 2013, 12)).

In 2001, Dr. Wakita's research team in Japan cloned HCV from a Japanese patient having fulminant hepatitis (named JFH-1 for Japanese fulminant hepatitis), which was a rare case among HCV patients. They developed HCV RNA replicon using the cloned HCV, which displayed very strong replicon activity. In 2005, those liver cancer cell lines good for HCV replication were selectively collected and the cell lines were transfected with the HCV RNA including the structural protein using the JFH-1 non-structural region as a backbone, resulting in the establishment of a HCV infection model in in vitro cell culture. The HCV obtained from these cultured cells was called HCVcc (cc is derived from cell culture). HCV infection by HCVcc was confirmed in chimpanzees, suggesting that the establishment of a cell culture derived HCV infection model was successful. HCVcc could be obtained by transfecting liver cancer cell lines with the JFH-1 RNA obtained through in vitro transcription, and the obtained HCVcc was confirmed to infect liver cancer cells again. The success of the establishment of a cell culture derived HCV infection model accelerated HCV research and therefore new discoveries are accelerated as well (see non-patent reference 5 (Hepatitis C virus research trend, Journal of Biochemistry & Molecular Biology, 2013, 12)).

Drugs that display anti-HCV activity by blocking a certain stage of HCV life cycle are classified into NS5B-RNA polymerase inhibitor type, NS3/4 protease inhibitor type, NS5A inhibitor type and other types based on HCV life cycle. For example, sofosbuvir, an FDA-approved inhibitor, is a type of RNA polymerase inhibitor and Daclatasvir (BMS-790052), ledipasvir (GS-5885), ombitasvir (ABT-267), elbasvir (MK-8742) and velpatasvir (GS-5816) are inhibitors that are targeting NS5A. Protease inhibitor type drugs are exemplified by Grazoprevir, Simeprevir and Paritaprevir. In addition, cyclophilin inhibitor type drugs are exemplified by Alisporivir, Bis-amide derivative, NIM258 and Phenylepyrrolidine derivative (see non-patent reference 6 (Kronenberger B., et al., Clin Liver Dis., 12, (2008), 529) and non-patent reference 7 (G Li et al. Antiviral Res 142, 83-122)).

However, since the emergence of a virus that is resistant to the anti-HCV drugs currently on the market has been reported, it is urgently required to develop a novel anti-HCV drug that exhibits an anti-HCV effect with the efficacy of solving the problem of resistant mutation against the conventional anti-HCV agents.

On the other hand, the difficulty in treating HCV is attributed to the diversity of the virus. The virus is classified into seven major genotypes including at least 50 subtypes. The reason of existing tens of different subtypes is that hepatitis C virus (HCV) has the highest mutation rate among hepatitis viruses. HCV has an immune evasion mechanism. First of all, mutations in the T cell receptor antigens on the surface of HCV cause protein modification to evade T-cell response, which is one of the reasons of high mutation rate.

For this reason, the treatment method of HCV is changing from the combination therapy of peg-interferon and ribavirin (PR), which has been accepted as a standard treatment method for more than 15 years up to date, to DAA (direct acting agent). Interferon which has been widely used in the standard treatment method causes many side effects such as flu symptoms, alopecia, skin pruritus at the injection site, leukopenia due to bone marrow suppression and depression. On the other hand, patients with advanced liver cirrhosis or aged patients are vulnerable for the side effects of these drugs, and therefore they often cannot finish the treatment. Even though those patients endure the treatment period, the treatment response is not so good. The drugs used in PR combination therapy are not comfortable because of injection, and are ineligible due to side effects and drug resistance. Thus, there is a need for development of a novel drug for oral administration as a new alternative to overcome these shortcomings. Interferon has an indirect therapeutic principle that enhances the host's immunity to gain antiviral efficacy. In the meantime, a direct acting agent targets the viral replication mechanism directly.

The NS5A inhibitor is one of the direct acting agents and is a replication complex inhibitor. The said NS5A inhibitor includes Daclatasvir (BMS-790052), ledipasvir (GS-5885), ombitasvir (ABT-267), elbasvir (MK-8742) and velpatasvir (GS-5816). These drugs inhibit the replication complex. Daclatasvir showed very limited therapeutic effect in genotype 1a and high therapeutic effect in genotype 1b. On the other hand, in the case of NS5A inhibitor, NS5A-L31 and NS5A-Y93 gene mutations appear, which causes drug resistance, so that the therapeutic effect is reduced.

In HCV, not only single mutation but also multiple mutations such as double mutations and triple mutations can occur. Such multiple mutations have been an issue because they can reduce the therapeutic effect significantly due to stronger drug resistance than single mutation.

Thus, the present inventors tried to develop a novel compound that exhibits an antiviral performance against HCV. In the course of our study, the present inventors confirmed that the fluorene derivative according to the present invention displayed an antiviral performance against not only HCV, but also highly against HCV mutants, so that it was able to be used as a pharmaceutical composition for the prevention or treatment of HCV-caused liver disease, such as acute hepatitis C, chronic hepatitis C, liver cirrhosis and hepatocellular cancer, leading to the completion of the present invention.

SUMMARY OF THE INVENTION

It is an object of the present invention to provide a fluorene derivative, an optical isomer thereof or a pharmaceutically acceptable salt thereof.

It is another object of the present invention to provide a preparation method for the fluorene derivative above.

It is also an object of the present invention to provide a pharmaceutical composition for preventing or treating HCV-related disease comprising the fluorene derivative, the optical isomer thereof or the pharmaceutically acceptable salt thereof as an active ingredient.

It is further an object of the present invention to provide a health functional food composition for preventing or ameliorating HCV-related disease comprising the fluorene derivative, the optical isomer thereof or the pharmaceutically acceptable salt thereof as an active ingredient.

To achieve the above objects, the present invention provides a compound represented by formula 1 below, an optical isomer thereof or a pharmaceutically acceptable salt thereof:

[Formula 1]

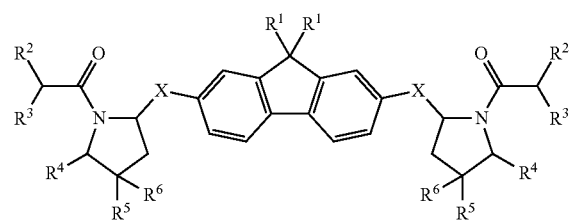

In Formula 1,

X is —NHC(=O)—, —C(=O)NH— or 5-8 membered heteroaryl containing one or more heteroatoms selected from the group consisting of N, O and S, in which at least one of X is necessarily —NHC(=O)— or —C(=O)NH—;

$R^1$ is straight $C_2$-$C_{10}$ alkyl nonsubstituted or substituted with one or more halogens;

$R^2$ is straight or branched $C_{1-10}$ alkoxycarbonylamino;

$R^3$ is straight or branched $C_{1-10}$ alkyl or $C_{6-10}$ aryl;

$R^4$ is hydrogen or can form $C_{3-7}$ cycloalkyl along with one of $R^5$ and $R^6$, and C atoms to which they are attached; and $R^5$ and $R^6$ are independently hydrogen, —OH, halogen, straight or branched $C_{1-10}$ alkoxy, straight or branched $C_{1-10}$ alkoxy-$C_{1-4}$ alkyl or —O(C=O)$R^a$, wherein $R^a$ is straight or branched $C_{1-10}$ alkyl or 5 or 6 membered heterocycloalkyl containing one or more heteroatoms selected from the group consisting of N, O and S-straight or branched $C_{1-4}$ alkyl, or, can form carbonyl, $C_{3-7}$ cycloalkyl or 3-7 membered heterocycloalkyl containing one or more O atoms along with C atoms to which they are attached.

The present invention also provides a preparation method of a compound represented by formula 1 comprising the step of preparing the compound represented by formula 1 by reacting the compound represented by formula 2 with the compound represented by formula 3, as shown in reaction formula 1 below:

[Reaction Formula 1]

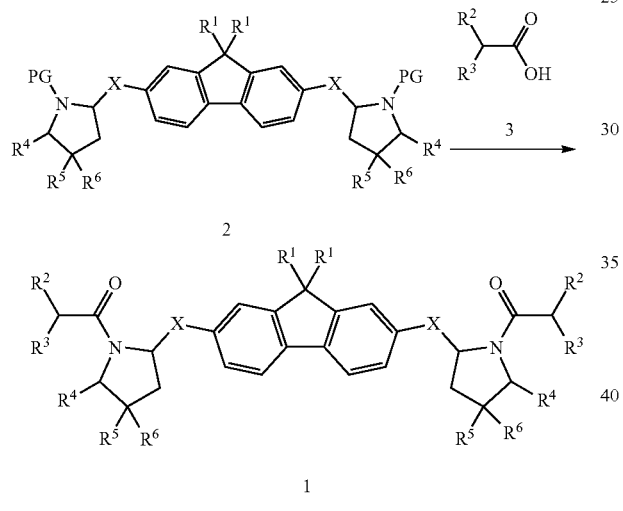

In reaction formula 1, $R^1$, $R^2$, $R^3$, $R^4$, $R^5$, $R^6$, and X are as defined in formula 1 above; and PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc).

The present invention also provides a pharmaceutical composition for preventing or treating HCV-related disease comprising the compound represented by formula 1 above, the optical isomer thereof or the pharmaceutically acceptable salt thereof as an active ingredient.

The present invention also provides a health functional food composition for preventing or ameliorating HCV-related disease comprising the compound represented by formula 1 above, the optical isomer thereof or the pharmaceutically acceptable salt thereof as an active ingredient.

The present invention also provides a method for preventing or treating HCV-related disease, which comprises the step of administering a pharmaceutical composition or a health functional food composition comprising the compound represented by formula 1 above, the optical isomer thereof or the pharmaceutically acceptable salt thereof as an active ingredient to a subject in need.

In addition, the present invention provides a use of the pharmaceutical composition or the health functional food composition comprising the compound represented by formula 1 above, the isomer thereof, the hydrate thereof or the pharmaceutically acceptable salt thereof in the prevention or treatment of HCV related liver disease.

Advantageous Effect

The fluorene derivative according to the present invention is identified to exhibit an antiviral performance against not only HCV, but also highly against HCV mutants, particularly double mutants and thus can be used in a pharmaceutical composition for prevention or treatment of HCV-caused liver disease, such as acute hepatitis C, chronic hepatitis C, liver cirrhosis, hepatocellular cancer, etc., particularly, liver disease caused by mutants of HCV. The derivative can be useful in a pharmaceutical composition for prevention or treatment of HCV-related liver disease by which the problem of resistant mutation against conventional therapeutic agents is solved.

DESCRIPTION OF THE PREFERRED EMBODIMENTS

Hereinafter, the present invention is described in detail.

The present invention provides a compound represented by formula 1 below, an optical isomer thereof or a pharmaceutically acceptable salt thereof:

[Formula 1]

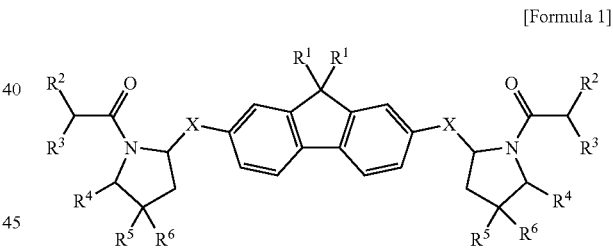

In formula 1,

X is —NHC(=O)—, —C(=O)NH— or 5-8 membered heteroaryl containing one or more heteroatoms selected from the group consisting of N, O and S, in which at least one of X is necessarily —NHC(=O)— or —C(=O)NH—;

$R^1$ is straight $C_2$-$C_{10}$ alkyl nonsubstituted or substituted with one or more halogens;

$R^2$ is straight or branched $C_{1-10}$ alkoxycarbonylamino;

$R^3$ is straight or branched $C_{1-10}$ alkyl or $C_{6-10}$ aryl;

$R^4$ is hydrogen or can form $C_{3-7}$ cycloalkyl along with one of $R^5$ and $R^6$, and C atoms to which they are attached; and $R^5$ and $R^6$ are independently hydrogen, —OH, halogen, straight or branched $C_{1-10}$ alkoxy, straight or branched $C_{1-10}$ alkoxy-$C_{1-4}$ alkyl or —O(C=O)$R^a$, wherein $R^a$ is straight or branched $C_{1-10}$ alkyl or 5 or 6 membered heterocycloalkyl containing one or more heteroatoms selected from the group consisting of N, O and S-straight or branched $C_{1-4}$ alkyl, or, can form carbonyl, $C_{3-7}$ cycloalkyl or 3-7 membered heterocycloalkyl containing one or more O atoms along with C atoms to which they are attached.

Preferably,

X is —NHC(=O)—, —C(=O)NH— or 5-6 membered heteroaryl containing one or more heteroatoms selected from the group consisting of N, O and S, in which at least one of X is necessarily —NHC(=O)— or —C(=O)NH—;

$R^1$ is straight $C_2$-$C_6$ alkyl nonsubstituted or substituted with one or more halogens;

$R^2$ is straight or branched $C_{1-6}$ alkoxycarbonylamino;

$R^3$ is straight or branched $C_{1-6}$ alkyl or phenyl;

$R^4$ is hydrogen or can form $C_{3-5}$ cycloalkyl along with one of $R^5$ and $R^6$, and C atoms to which they are attached; and $R^5$ and $R^6$ are independently hydrogen, —OH, halogen, straight or branched $C_{1-6}$ alkoxy, straight or branched $C_{1-6}$ alkoxy-$C_{1-2}$ alkyl or —O(C=O)$R^a$, wherein $R^a$ is straight or branched $C_{1-6}$ alkyl or 6 membered heterocycloalkyl containing one or more heteroatoms selected from the group consisting of N, O and S—$C_{1-2}$ alkyl, or can form carbonyl, $C_{3-5}$ cycloalkyl or 3-5 membered heterocycloalkyl containing one or more 0 atoms along with C atoms to which they are attached.

More preferably,

X is —NHC(=O)—, —C(=O)NH— or imidazole, in which at least one of X is necessarily —NHC(=O)— or C(=O)NH—;

$R^1$ is straight $C_2$-$C_6$ alkyl nonsubstituted or substituted with one or more F;

$R^2$ is straight or branched $C_{1-4}$ alkoxycarbonylamino;

$R^3$ is straight or branched $C_{1-4}$ alkyl or phenyl;

$R^4$ is hydrogen or can form cyclopropyl or cyclopentyl along with one of $R^5$ and $R^6$, and C atoms to which they are attached; and $R^5$ and $R^6$ are independently hydrogen, —OH, halogen, straight or branched $C_{1-4}$ alkoxy, straight or branched $C_{1-4}$ alkoxy-$C_{1-2}$ alkyl or —O(C=O)$R^a$, wherein $R^a$ is straight or branched $C_{1-4}$ alkyl or morpholinyl-$C_{1-2}$ alkyl, or can form carbonyl, $C_{3-5}$ cycloalkyl or 5 membered heterocycloalkyl containing one or more 0 atoms along with C atoms to which they are attached.

Most preferably,
X is

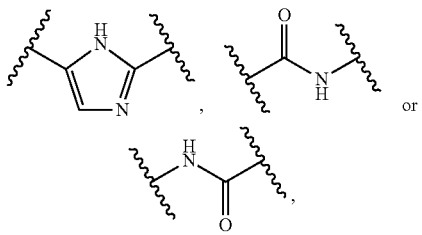

in which at least one of X is necessarily

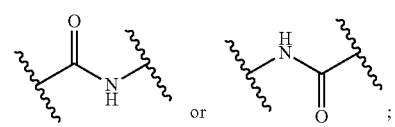 [SMILES: *NC(*)=O ; *NC(*)=O]

$R^1$ is —CH$_2$CH$_3$, —(CH$_2$)$_2$CH$_3$, —(CH$_2$)$_3$CH$_3$— (CH$_2$)$_4$CH$_3$, —(CH$_2$)$_3$CF$_3$ or —(CH$_2$)$_4$CF$_3$;
$R^2$ is

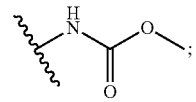

$R^3$ is isopropyl or phenyl;
$R^4$ is hydrogen or can form cyclopentyl along with one of $R^5$ and $R^6$, and C atoms to which they are attached; and
$R^5$ and $R^6$ are independently hydrogen, —OH, —F, —OCH$_3$, —CH$_2$OCH$_3$, —O(CH$_2$)$_2$OCH$_3$,

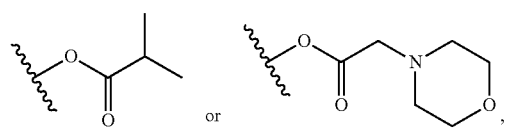

or can form carbonyl, cyclopropyl or 1,3-dioxolanyl along with C atoms to which they are attached.

Preferable examples of the compound represented by formula 1 according to the present invention include the compounds represented by formulas 1-1 to 1-42 below.

[Formula 1-1]

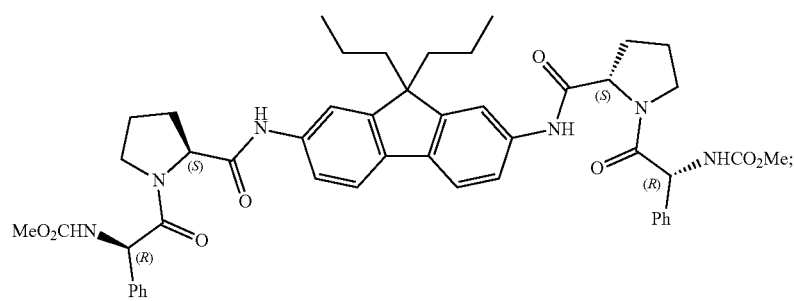

[Formula 1-2]
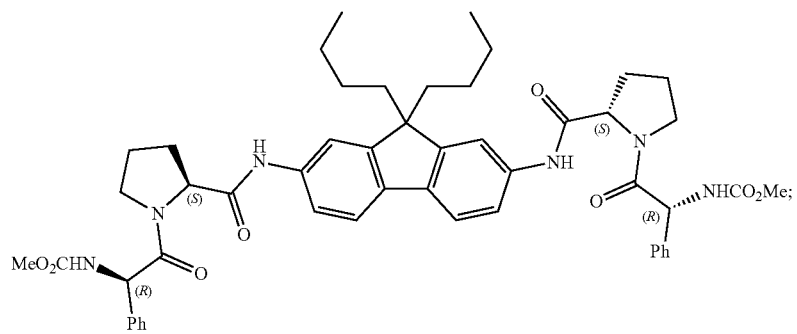
[Formula 1-3]
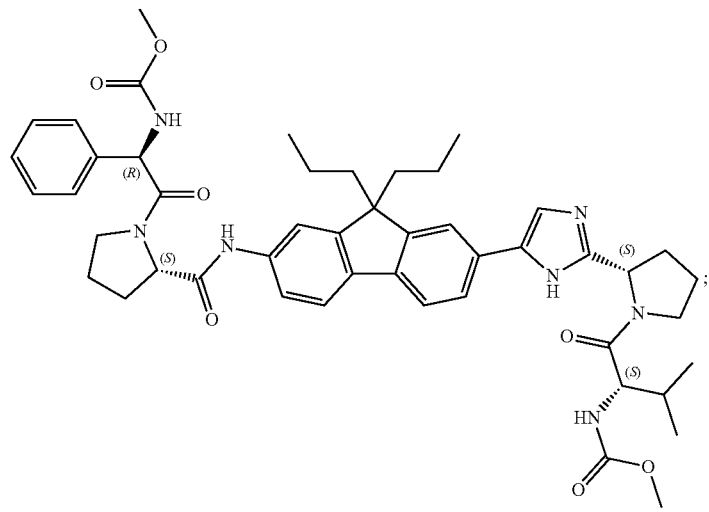
[Formula 1-4]
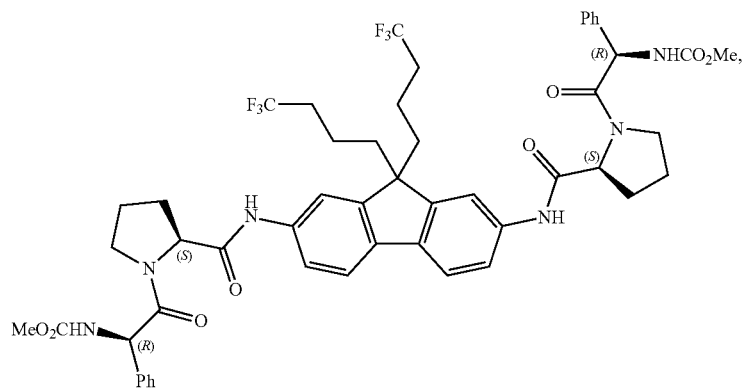
[Formula 1-5]
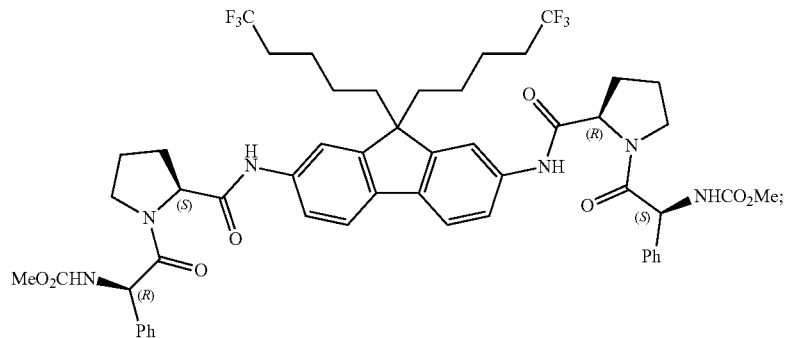

[Formula 1-6]
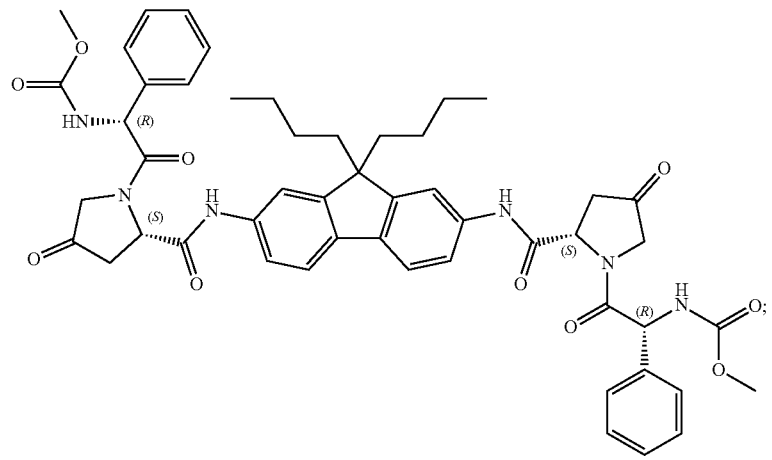
[Formula 1-7]
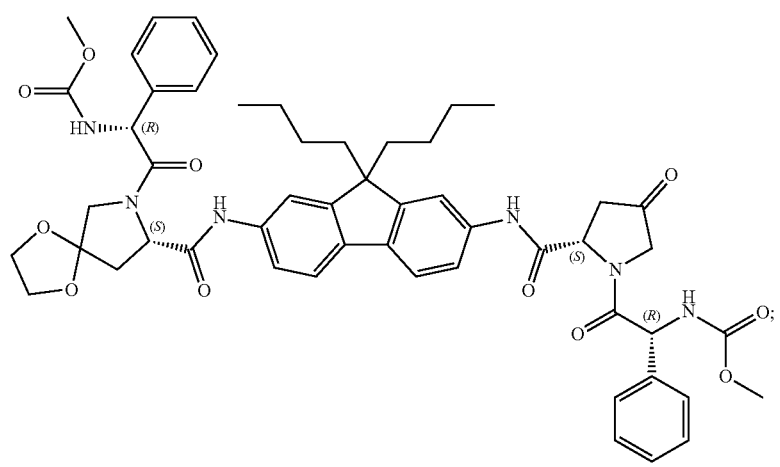
[Formula 1-8]
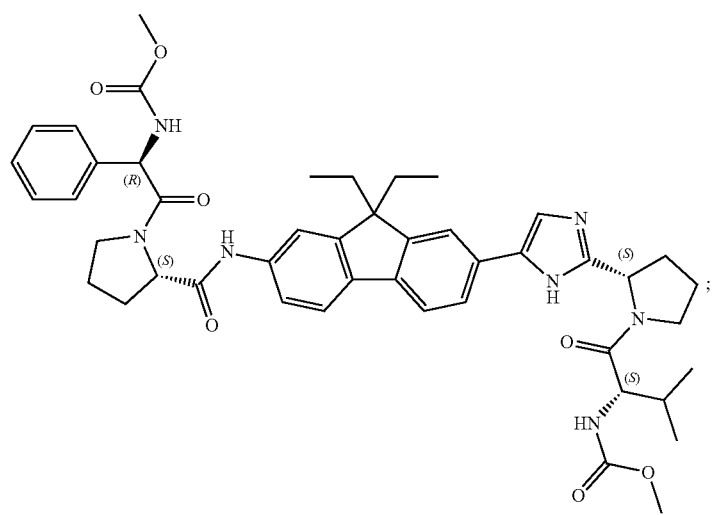

[Formula 1-9]
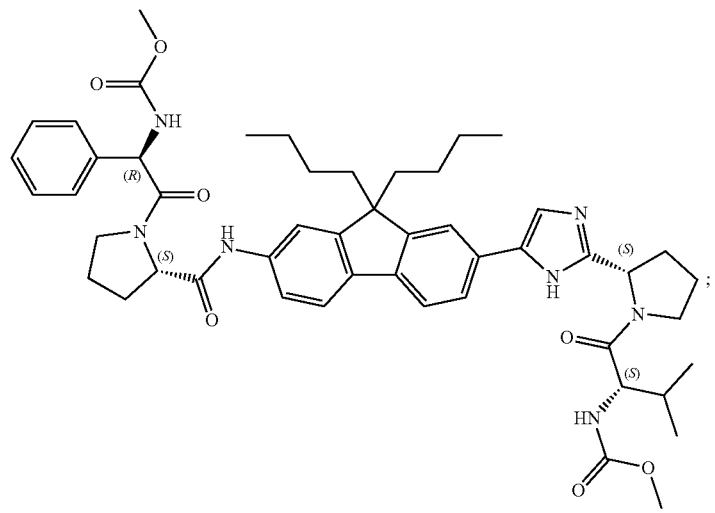
[Formula 1-10]
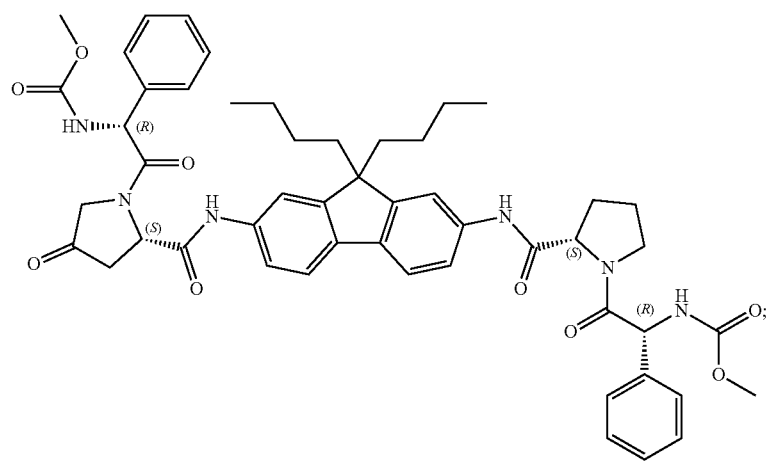
[Formula 1-11]
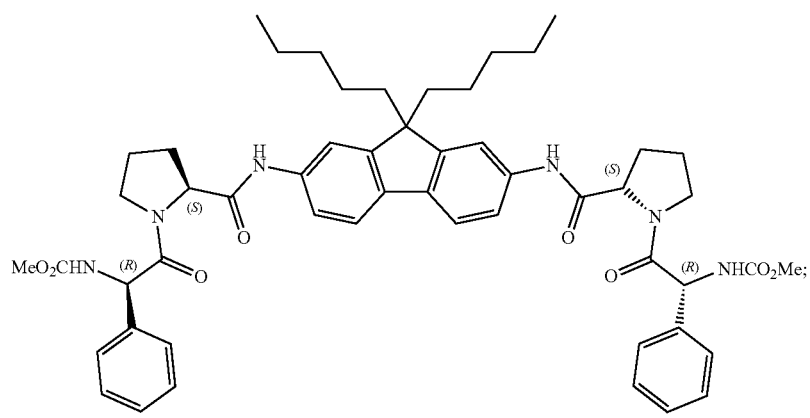

[Formula 1-12]
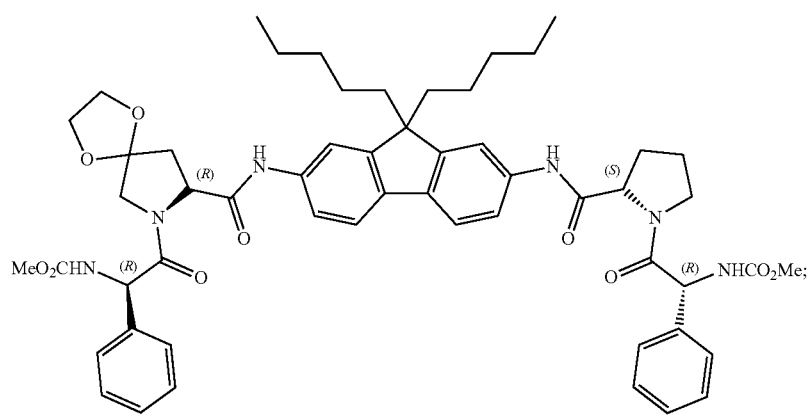
[Formula 1-13]
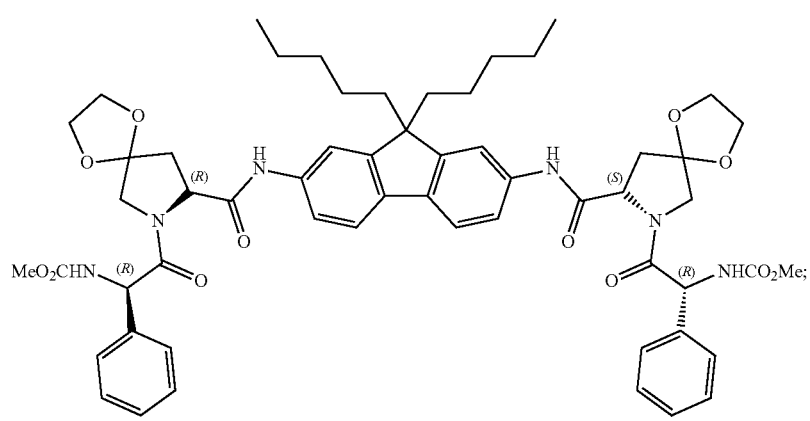
[Formula 1-14]
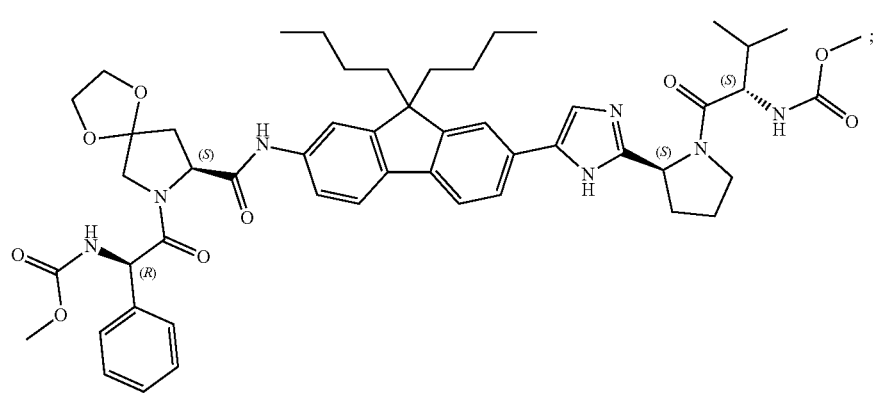
[Formula 1-15]
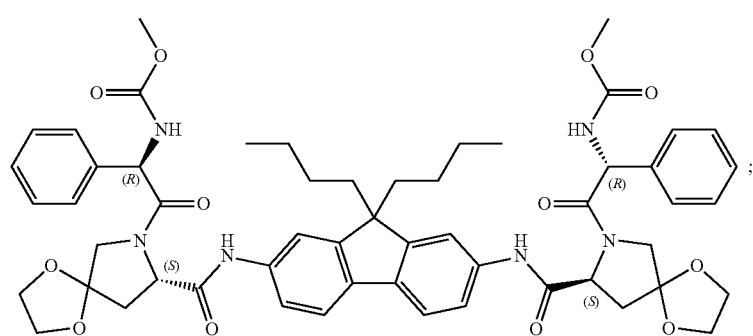

[Formula 1-16]
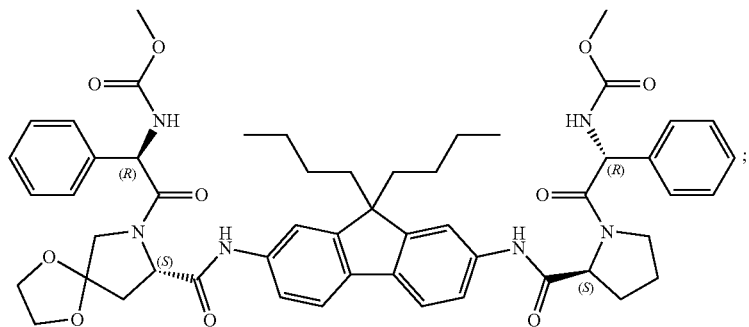
[Formula 1-17]
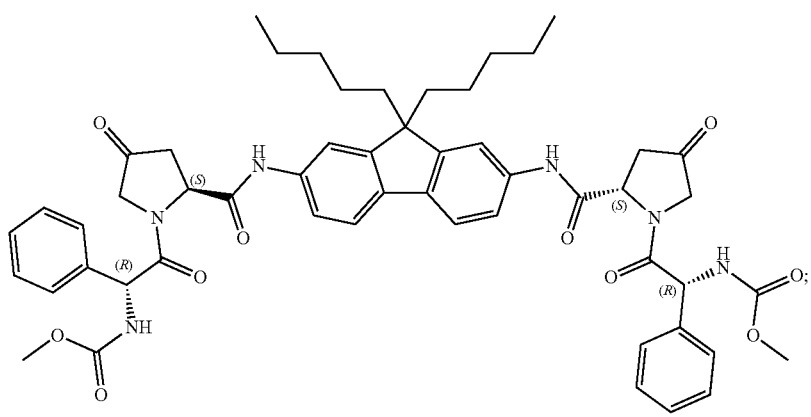
[Formula 1-18]
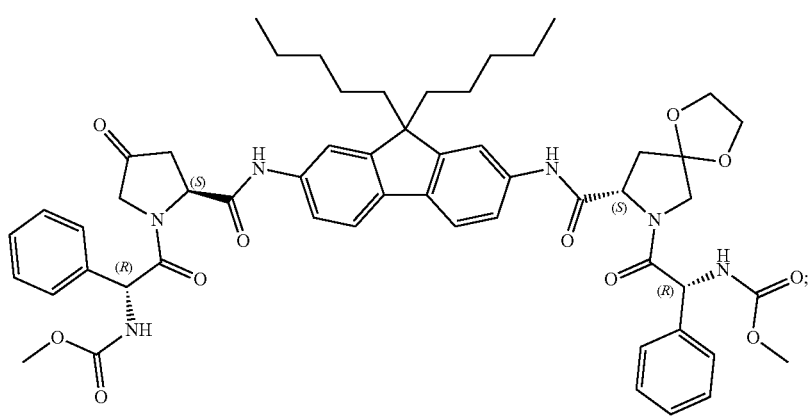
[Formula 1-19]
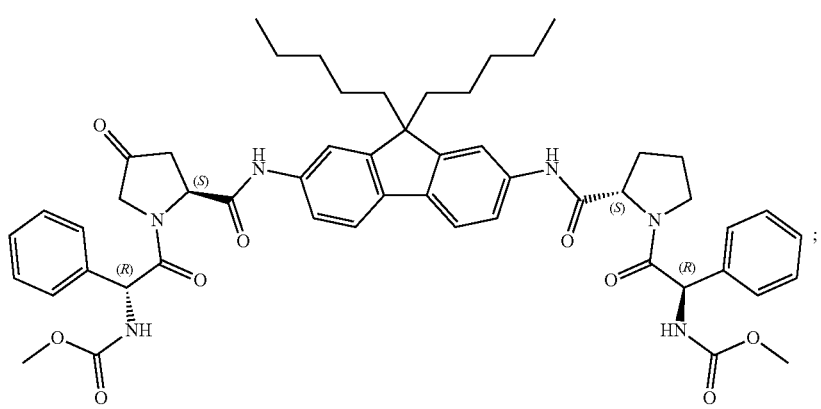

-continued
[Formula 1-20]
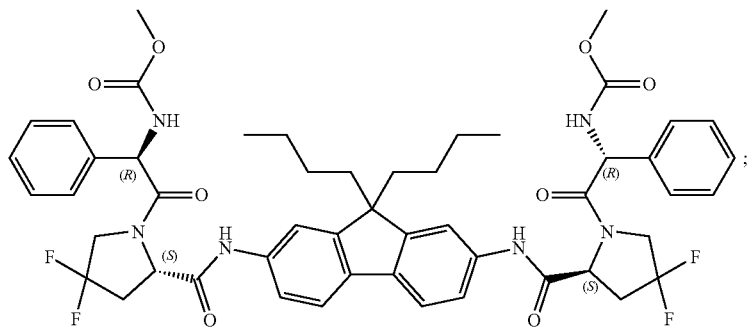
[Formula 1-21]
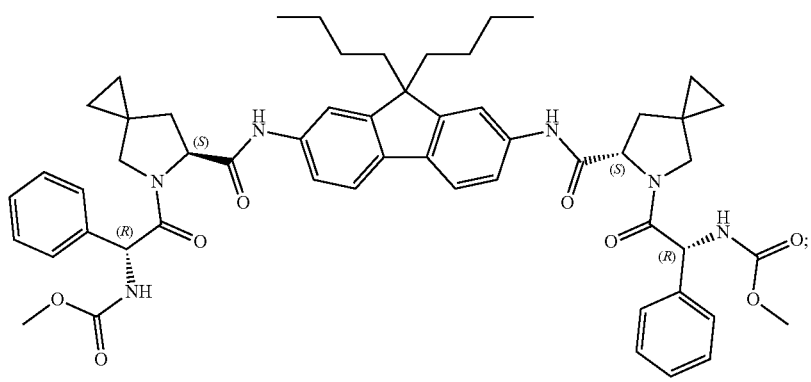
[Formula 1-22]
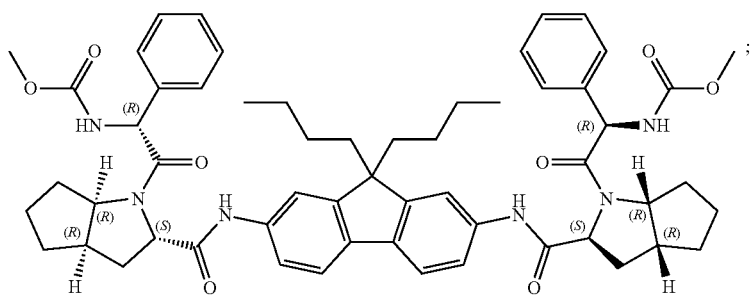
[Formula 1-23]
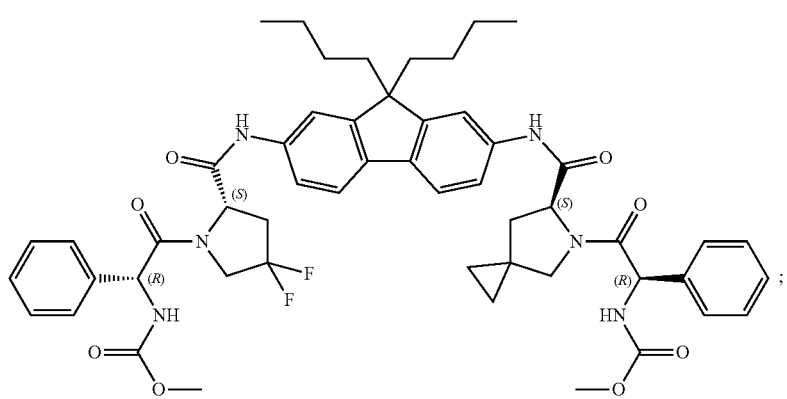

[Formula 1-24]
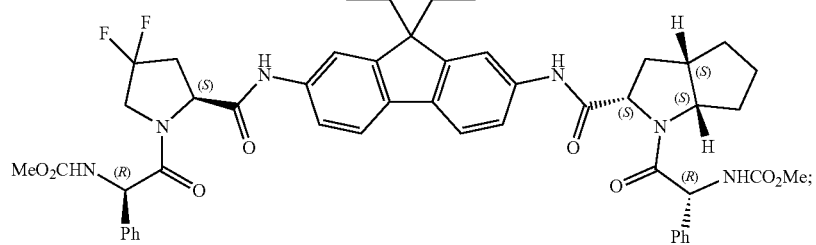
[Formula 1-25]
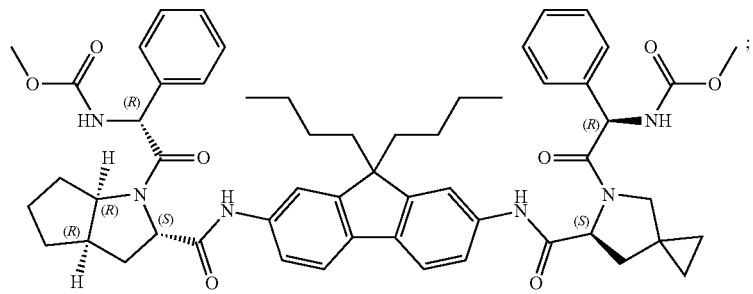
[Formula 1-26]
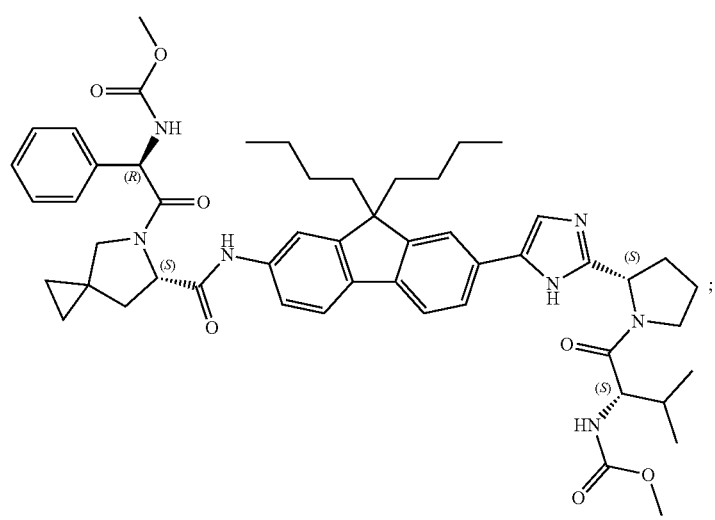
[Formula 1-27]
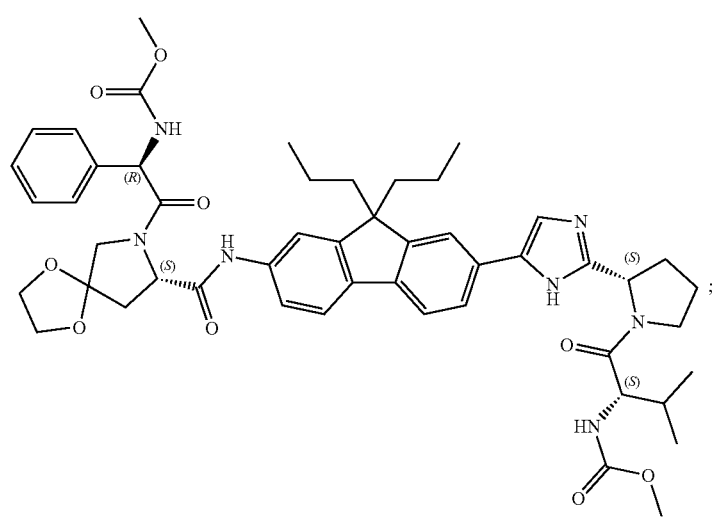

[Formula 1-28]
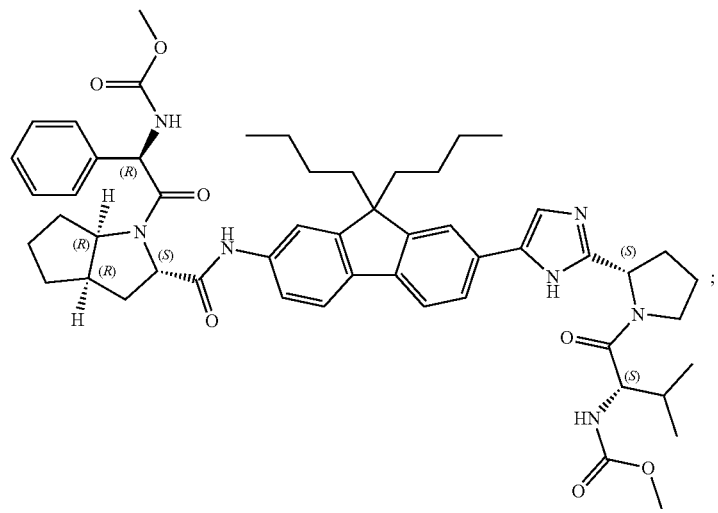
[Formula 1-29]
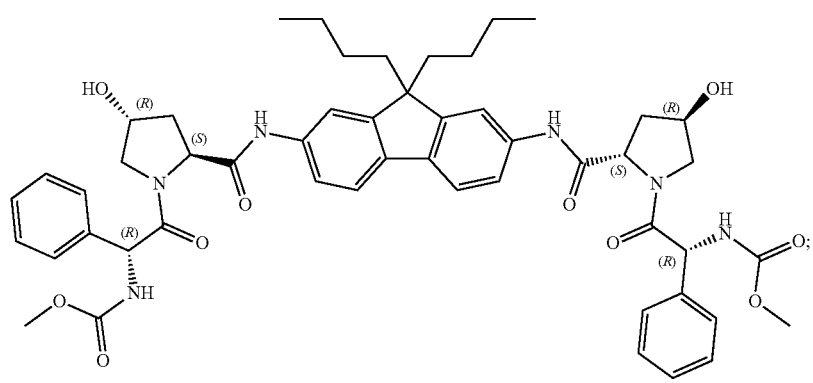
[Formula 1-30]
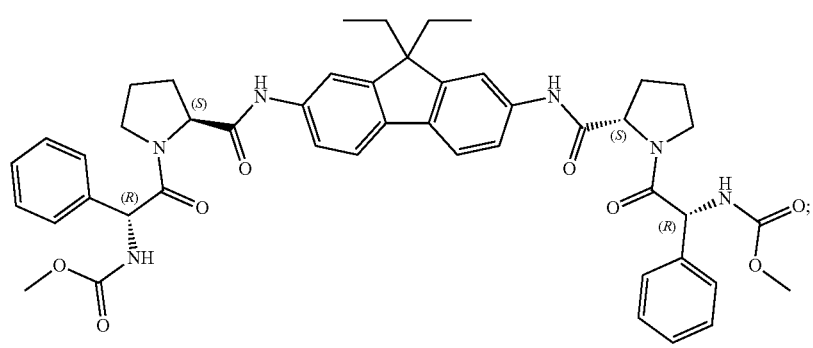

[Formula 1-31]
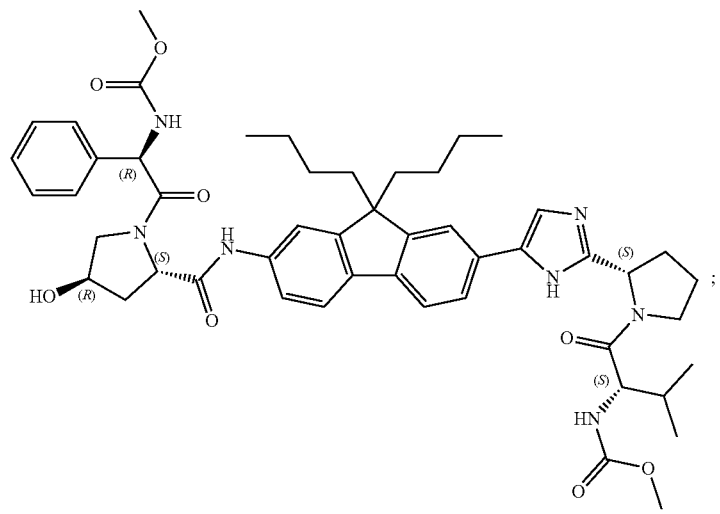
[Formula 1-32]
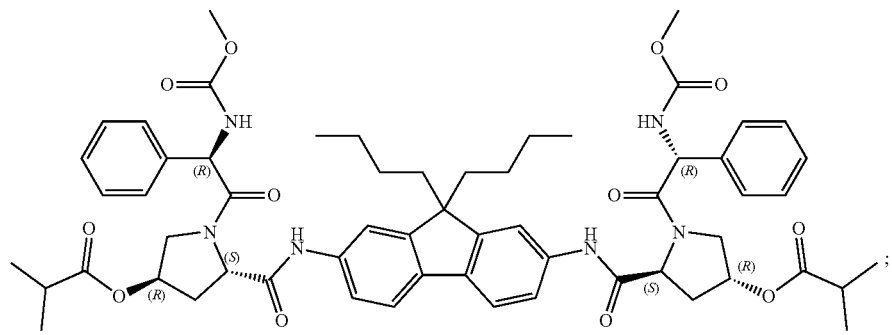
[Formula 1-33]
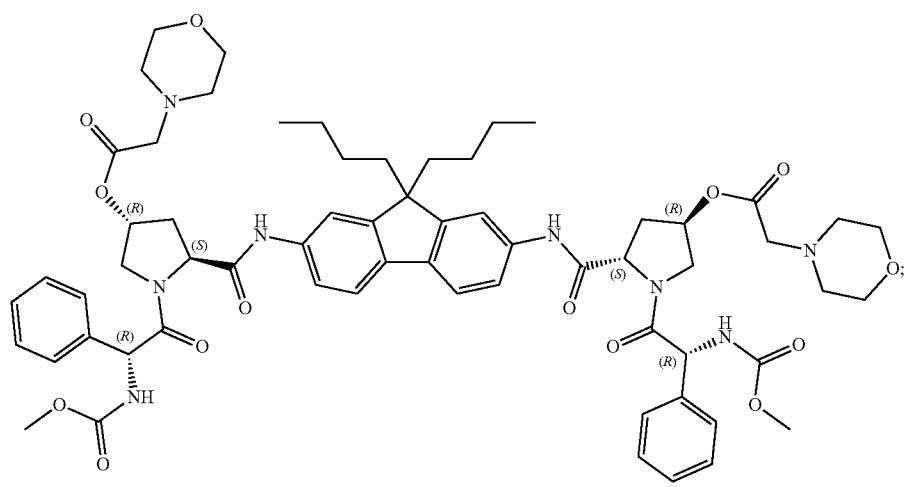

[Formula 1-34]
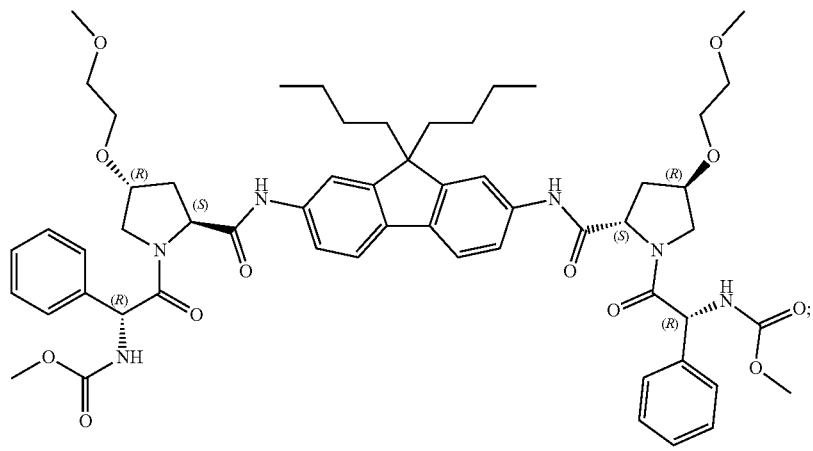
[Formula 1-35]
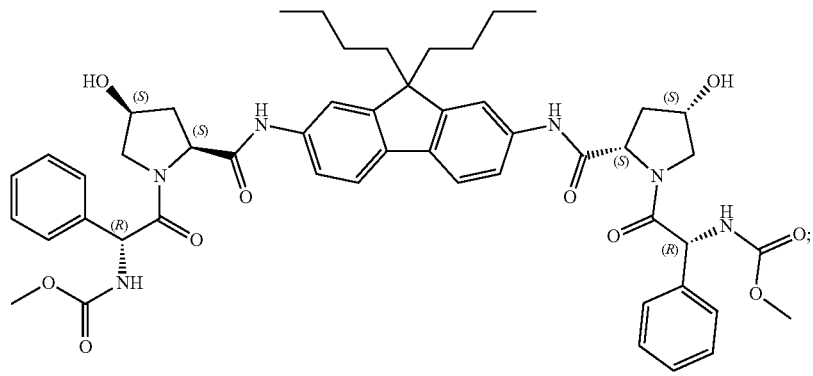
[Formula 1-36]
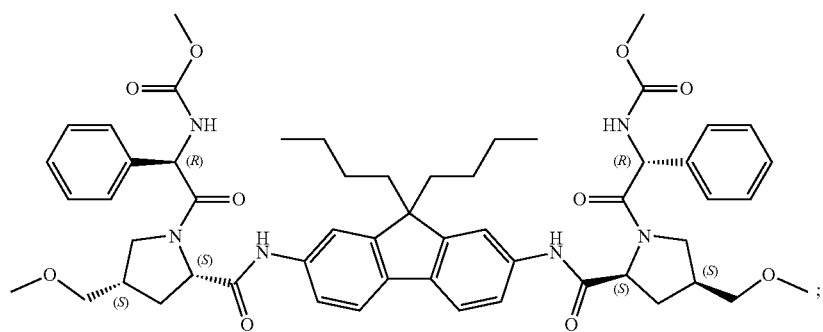
[Formula 1-37]
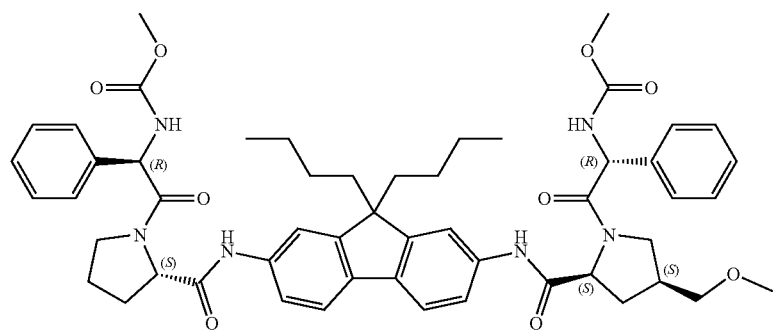

-continued
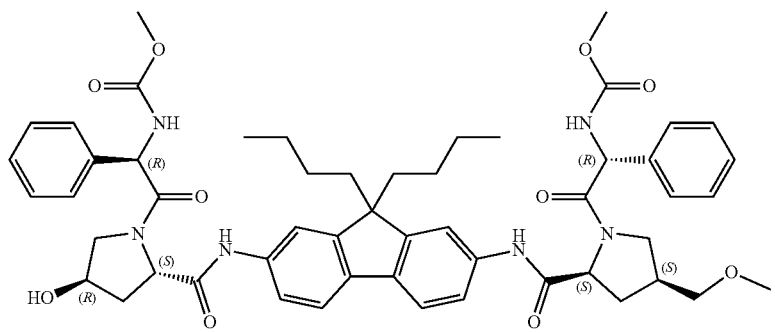
[Formula 1-38]
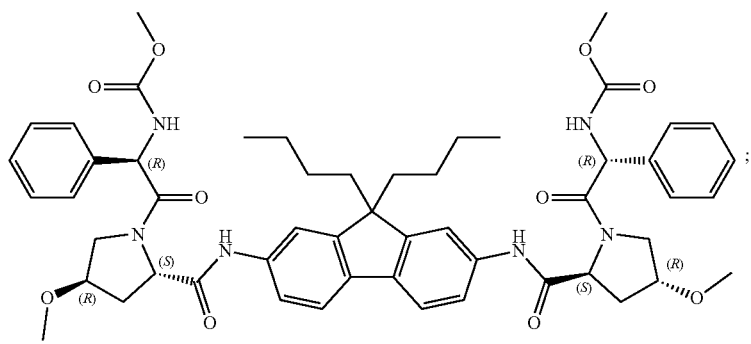
[Formula 1-39]
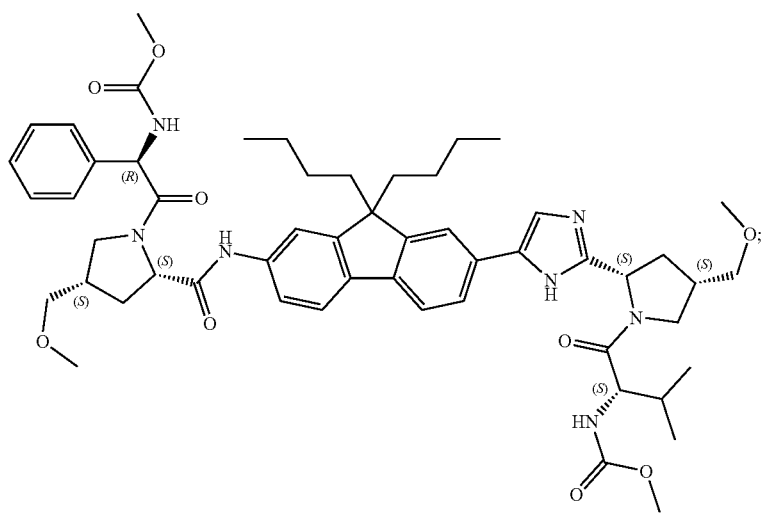
[Formula 1-40]

[Formula 1-41]

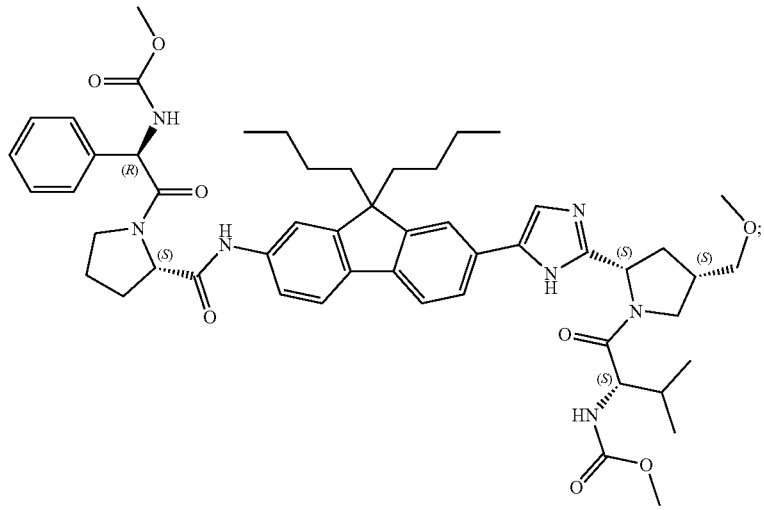

[Formula 1-42]

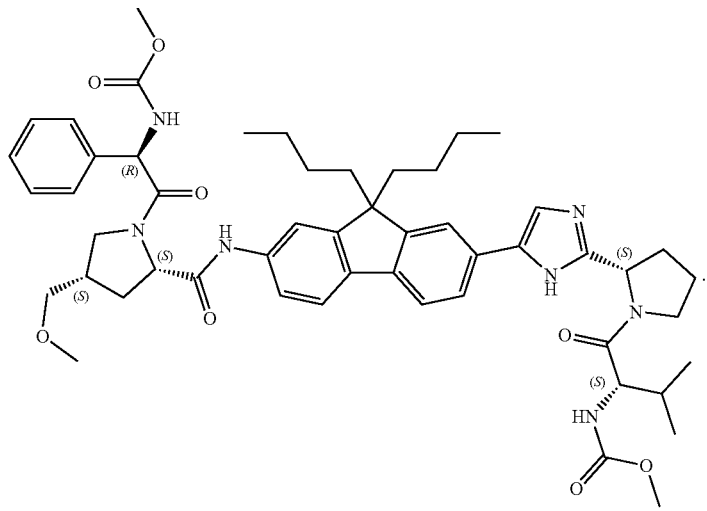

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex, silver nitrate).

In addition, the present invention includes not only the compound represented by formula 1 but also a pharmaceutically acceptable salt thereof, and a solvate, an optical isomer or a hydrate possibly produced from the same.

The present invention also provides a preparation method of a compound represented by formula 1 comprising the step of preparing the compound represented by formula 1 by reacting the compound represented by formula 2 with the compound represented by formula 3, as shown in reaction formula 1 below:

[Reaction Formula 1]

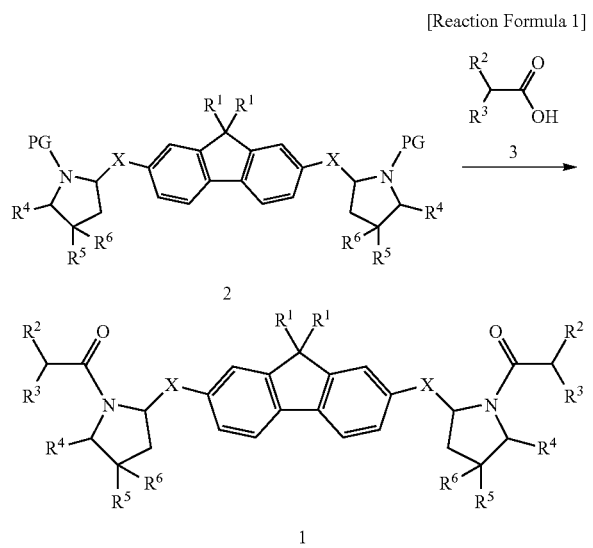

In reaction formula 1, $R^1$, $R^2$, $R^3$, $R^4$, $R^5$, $R^6$ and X are as defined in formula 1 above; and PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc).

Hereinafter, the preparation method of a compound represented by formula 1 according to the present invention is described in more detail.

In the preparation method of a compound represented by formula 1 according to the present invention, a compound represented by formula 1 can be prepared by reacting a compound represented by formula 2 with a compound represented by formula 3, as shown in reaction formula 1.

Particularly, the compound represented by formula can be prepared by removing an amine protecting group of the compound represented by formula 2 and adding the compound represented by formula 3 in the presence of an amide reagent thereto, followed by reacting.

At this time, the amine protecting group can be t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) or aryloxycarbonyl (Alloc), and t-butyloxycarbonyl (BOC) is more preferred herein.

In addition, the amine protecting group can be removed by the conventional method. For example, it can be removed under the conditions using an acid or a base. The acid can be exemplified by hydrochloric acid, sulfuric acid, trifluoroacetic acid, bromic acid, and the like, and the base can be exemplified by piperidine, ammonia gas, etc., which can be used in an equivalent amount or excessive amount.

As the amide reagent, benzotriazol-1-yl-oxy-tris (dimethylamino)-phosphonium hexafluorophosphate (Py-BOP), O-benzotriazole-N,N,N,N-tetramethyl-uronium-hexafluoro-phosphate (HBTU), 2-(7-aza-1H-benzotriazol-1-yl)-1,1,3,3-tetramethyluronium hexafluorophosphate (HATU), hydroxybenzotriazole (HOBt), dicyclohexylcarbodiimide (DCC), 1-ethyl-3-(3-dimethylaminopropyl)carbodiimide (EDCI) or carbonyldiimidazole (CDI) can be used. Preferably, 1-ethyl-3-(3-dimethylaminopropyl) carbodiimide (EDCI) can be used with diisopropylethylamine (DIPEA), triethylamine (TEA) or dimethylaminopyridine (DMAP).

The solvent usable in the reaction is exemplified by ether solvents such as tetrahydrofuran, dioxane and 1,2-dimethoxyethane; aromatic hydrocarbon solvents such as benzene, toluene and xylene; lower alcohols such as methanol, ethanol, propanol and butanol; dimethylformamide (DMF); dimethylsulfoxide (DMSO); acetonitrile; and water, which can be used independently or in combination.

In addition, the present invention provides a pharmaceutical composition for preventing or treating HCV-related liver disease comprising the compound represented by formula 1 above, the optical isomer thereof or the pharmaceutically acceptable salt thereof as an active ingredient.

Preparation of Starting Material (Compound Represented by Formula 2)

A compound of formula 2, which is a starting material of reaction formula 1, can be prepared by the preparation method as shown in reaction formulas 2 to 4 below.

The derivative 2a of the compound represented by formula 2, wherein X is all —NHC(=O)— or —C(=O)NH—, can be prepared by the preparation method as shown in reaction formula 2 or 3.

The derivative 2a of the compound represented by formula 2, wherein X is all —NHC(=O)— or —C(=O)NH—, can be prepared by the preparation method comprising the following steps, as shown in reaction formula 2 below:

preparing a compound represented by formula 6 by reacting a compound represented by formula 4 with a compound represented by formula 5 (step 1);

preparing a compound represented by formula 8 by reacting the compound represented by formula 6 obtained in step 1 above with a compound represented by formula 7 (step 2);

preparing a compound represented by formula 10 by reacting the compound represented by formula 8 obtained in step 2 above with a compound represented by formula 9 (step 3); and preparing a compound represented by formula 2a by reacting the compound represented by formula 10 obtained in step 3 above with a compound represented by formula 11 (step 4).

[Reaction Formula 2]

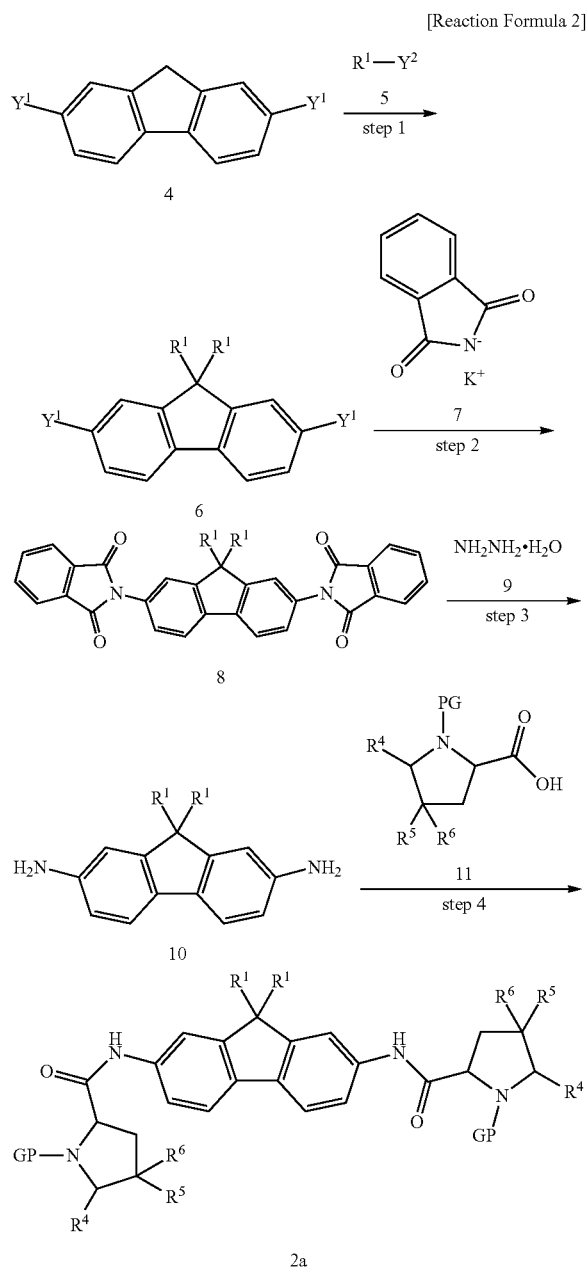

In reaction formula 2, $R^1$, $R^4$, $R^5$ and $R^6$ are as defined in formula 1 above;

PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc); and $Y^1$ and $Y^2$ are independently halogen.

Hereinafter, the preparation method shown in reaction formula 2 will be described in detail.

In the preparation method shown in reaction formula 2 above according to the present invention, step 1 is to prepare a compound represented by formula 6 by reacting a compound represented by formula 4 with a compound represented by formula 5. Particularly, this step is to prepare a compound represented by formula 6 wherein alkyl is introduced through alkylation reaction using a phase-transfer catalyst.

At this time, as the phase-transfer catalyst, a conventional phase-transfer catalyst can be used, and preferably a quaternary ammonium salt can be used. In the present invention, TBAB (tetra-n-butylammonium bromide) was used, but not always limited thereto.

The solvent usable in the reaction is exemplified by ether solvents such as tetrahydrofuran, dioxane and 1,2-dimethoxyethane; aromatic hydrocarbon solvents such as benzene, toluene and xylene; lower alcohols such as methanol, ethanol, propanol and butanol; dimethylformamide (DMF); dimethylsulfoxide (DMSO); acetonitrile; and water, which can be used independently or in combination.

In addition, the base herein can be selected from the group consisting of such organic bases as N,N-dimethylaminopyridine (DMAP), pyridine, triethylamine, N,N-diisopropylethylamine and 1,8-diazabicyclo[5.4.0]-7-undecene (DBU), and such inorganic bases as sodium bicarbonate, sodium hydroxide and potassium hydroxide. The selected base can be used in an equivalent amount or excessive amount, alone or in combination.

In the preparation method shown in reaction formula 2 above according to the present invention, step 2 is to prepare a compound represented by formula by reacting the compound represented by formula 6 obtained in step 1 above with a compound represented by formula 7, and step 3 is to prepare a compound represented by formula 10 by reacting the compound represented by formula 8 obtained in step 2 above with a compound represented by formula 9. Particularly, the phthalimide bound compound represented by formula 8 is prepared by reacting the halogen of the compound represented by formula 6 and the amine of the phthalimide compound represented by formula 7 in step 2, and then the primary amine is prepared using the hydrazine compound represented by formula 10 in step 3.

Steps 2 and 3 above can be performed through the reaction conditions of —$NH_2$ production method (Gabriel Synthesis) using the general phthalimide well known to those skilled in the art. In this invention, the steps were performed as in the embodiments according to the present invention, but not always limited thereto.

In the preparation method shown in reaction formula 2 above according to the present invention, step 4 is to prepare a compound represented by formula 2a by reacting the compound represented by formula 10 obtained in step 3 above with a compound represented by formula 11. Particularly, the compound represented by formula 2a can be prepared by condensation reaction in the presence of a condensing agent and a base.

At this time, the condensing agent can be exemplified by organophosphorus reagents such as bis(2-oxo-3-oxazolidinyl)phosphonic chloride (BOP-Cl), benzotriazol-1-yloxytris(dimethylamino)phosphonium hexafluorophosphate (BOP) and diphenylphosphonylazide (DPPA); carbodiimide reagents such as dicyclohexylcarbodiimide (DCC), diisopropylcarbodiimide (DIC) and 1-ethyl-3-(3-dimethylaminopropyl)carbodiimide (EDCI); N,N-carbonyldiimidazole; and O-benzotriazole-N,N,N',N'-tetramethyl-uroniumhexafluorophosphate (HBTU), which can be used independently or in combination.

The base herein can be selected from the group consisting of such organic bases as N,N-dimethylaminopyridine (DMAP), pyridine, triethylamine, N,N-diisopropylethylamine and 1,8-diazabicyclo[5.4.0]-7-undecene (DBU), and such inorganic bases as sodium bicarbonate, sodium hydroxide and potassium hydroxide. The selected base can be used independently or in combination.

In addition, the solvent usable in the reaction is exemplified by ether solvents such as tetrahydrofuran, dioxane and 1,2-dimethoxyethane; aromatic hydrocarbon solvents such as benzene, toluene and xylene; lower alcohols such as methanol, ethanol, propanol and butanol; dimethylformamide (DMF); dimethylsulfoxide (DMSO); acetonitrile; and water, which can be used independently or in combination.

The derivative 2a of the compound represented by formula 2, wherein X is all —NHC(=O)— or —C(=O)NH—, can be prepared by the preparation method as shown in reaction formula 2 or 3.

The derivative 2a of the compound represented by formula 2, wherein X is all —NHC(=O)— or —C(=O)NH—, can be prepared by the preparation method comprising the following steps, as shown in reaction formula 3 below:

preparing a compound represented by formula 13 by reacting a compound represented by formula 12 with a compound represented by formula 5 (step 1);

preparing a compound represented by formula 10 by reacting the compound represented by formula 13 obtained in step 1 above with a compound represented by formula 9 (step 2); and preparing a compound represented by formula 2a by reacting the compound represented by formula 10 obtained in step 2 above with a compound represented by formula 11 (step 3).

[Reaction Formula 3]

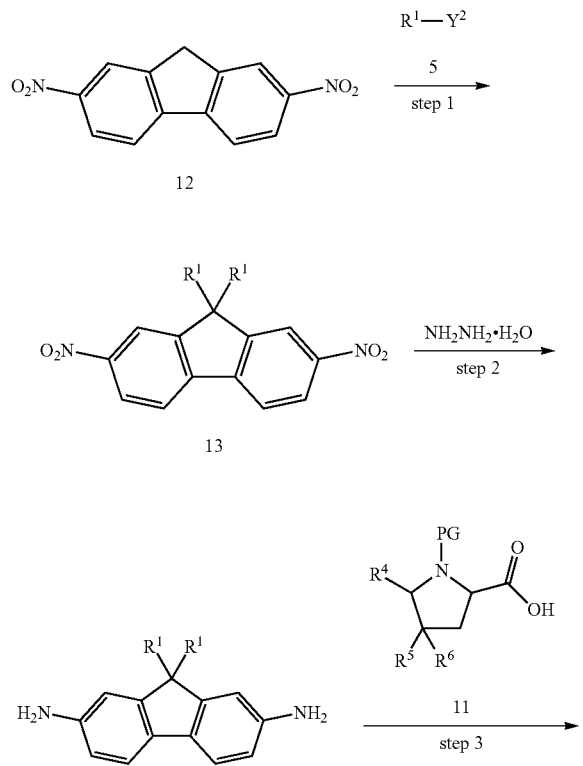

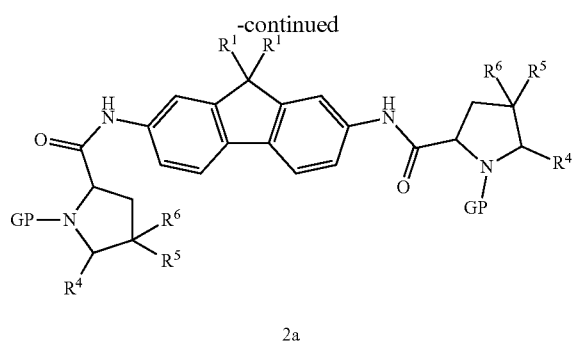

In reaction formula 3, $R^1$, $R^4$, $R^5$ and $R^6$ are as defined in formula 1 above;

PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc); and $Y^2$ is halogen.

Hereinafter, the preparation method shown in reaction formula 3 will be described in detail.

In the preparation method shown in reaction formula 3 above according to the present invention, step 1 is to prepare a compound represented by formula by reacting a compound represented by formula 12 with a compound represented by formula 5. Particularly, this step is to prepare a compound represented by formula 13 wherein alkyl is introduced through alkylation reaction in the presence of a base.

At this time, the base can be selected from the group consisting of such organic bases as N,N-dimethylaminopyridine (DMAP), pyridine, triethylamine, N,N-diisopropylethylamine and 1,8-diazabicyclo[5.4.0]-7-undecene (DBU), and such inorganic bases as sodium bicarbonate, sodium hydroxide and potassium hydroxide. The selected base can be used in an equivalent amount or excessive amount, alone or in combination. In the present invention, cesium carbonate was used, but not always limited thereto.

The solvent usable in the reaction is exemplified by ether solvents such as tetrahydrofuran, dioxane and 1,2-dimethoxyethane; aromatic hydrocarbon solvents such as benzene, toluene and xylene; lower alcohols such as methanol, ethanol, propanol and butanol; dimethylformamide (DMF); dimethylsulfoxide (DMSO); acetonitrile; and water, which can be used independently or in combination.

In the preparation method shown in reaction formula 3 above according to the present invention, step 2 is to prepare a compound represented by formula 10 by reacting the compound represented by formula 13 obtained in step 1 above with a compound represented by formula 9. Particularly, this step is to prepare the primary amine by reducing nitro ($NO_2$) of the compound represented by formula 13 in the presence of a metal catalyst and the hydrazine compound represented by formula 9.

Step 2 can be performed through the conventional method of reducing nitro group to amine known to those skilled in the art. In this invention, the step was performed as in the embodiment according to the present invention, but not always limited thereto.

In the preparation method shown in reaction formula 3 above according to the present invention, step 3 is to prepare a compound represented by formula 2a by reacting the compound represented by formula 10 obtained in step 2 above with a compound represented by formula 11.

Detailed description of step 3 is the same as step 4 of the preparation method shown in reaction formula 2.

The derivative 2b of the compound represented by formula 2, wherein one of X is imidazole and the other is —NHC(=O)— or —C(=O)NH—, can be prepared by the preparation method comprising the following steps, as shown in reaction formula 4 below:

preparing a compound represented by formula 15 by reacting a compound represented by formula 14 with a compound represented by formula 5 (step 1);

preparing a compound represented by formula 17 by reacting the compound represented by formula 15 obtained in step 1 above with a compound represented by formula 16 (step 2);

preparing a compound represented by formula 18 by reacting the compound represented by formula 17 obtained in step 2 above with a compound represented by formula 11 (step 3);

preparing a compound represented by formula 19 by reacting the compound represented by formula 18 obtained in step 3 above (step 4);

preparing a compound represented by formula 20 by reacting the compound represented by formula 19 obtained in step 4 above (step 5); and preparing a compound represented by formula 2b by reacting the compound represented by formula 20 obtained in step 5 above with a compound represented by formula 11 (step 6).

[Reaction Formula 4]

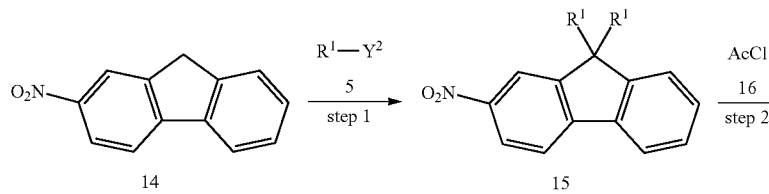

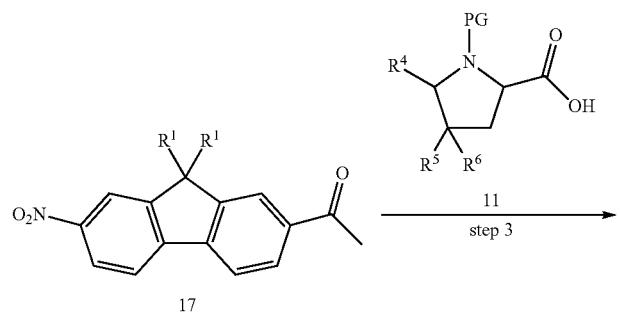

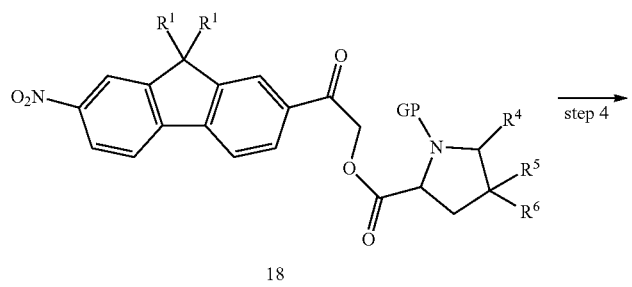

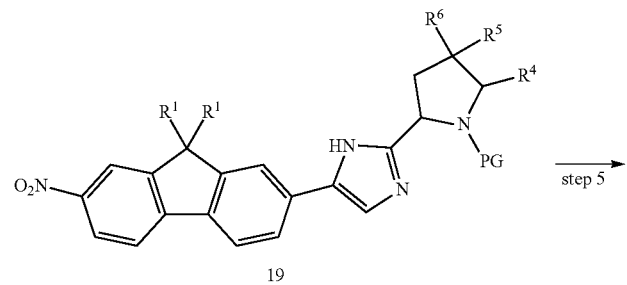

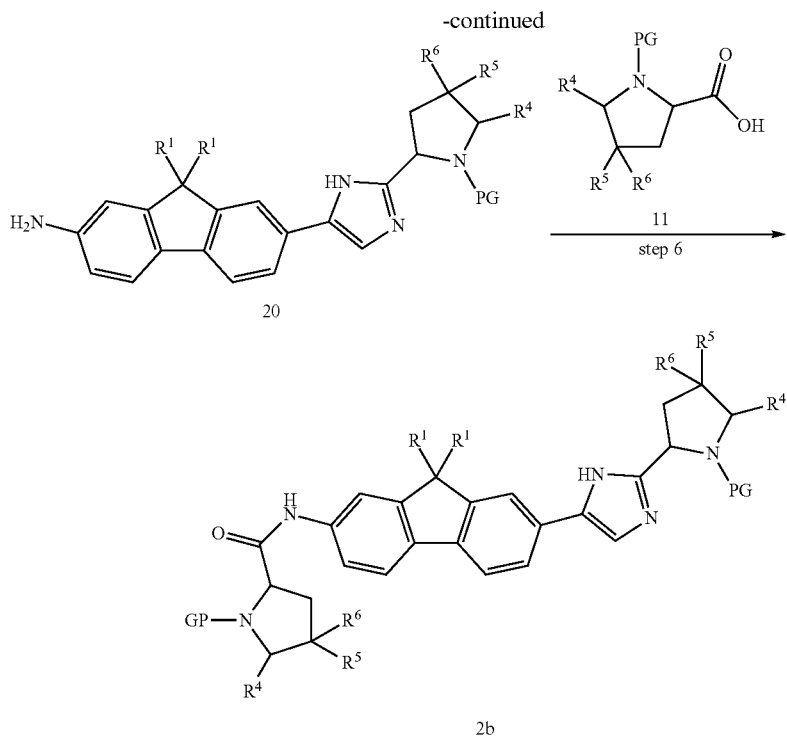

In reaction formula 4,

R[1], R[4], R[5] and R[6] are as defined in formula 1 above;

PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc); and Y[2] is halogen.

Hereinafter, the preparation method shown in reaction formula 4 will be described in detail.

In the preparation method shown in reaction formula 4 above according to the present invention, step 1 is to prepare a compound represented by formula by reacting a compound represented by formula 15 with a compound represented by formula 5.

Detailed description of step 1 is the same as step 1 of the preparation method shown in reaction formula 3.

In the preparation method shown in reaction formula 4 above according to the present invention, step 2 is to prepare a compound represented by formula 17 by reacting the compound represented by formula 15 obtained in step 1 above with a compound represented by formula 16. Particularly, this step is to introduce an acetyl group to the compound represented by formula 15 through Friedel-Crafts acylation.

Step 2 can be performed through the general Friedel-Crafts acylation conditions well known to those skilled in the art. In this invention, the step was performed as in the embodiment according to the present invention, but not always limited thereto.

In the preparation method shown in reaction formula 4 above according to the present invention, step 3 is to prepare a compound represented by formula 18 by reacting the compound represented by formula 17 obtained in step 2 above with a compound represented by formula 11. Particularly, this step is to prepare a compound represented by formula 18 by bromination of an acetyl group, and then reacting the compound represented by formula 11 in the presence of a base.

At this time, the said bromination can be performed by the general bromination conditions well known to those skilled in the art. In this invention, the bromination was performed using NBS (N-bromosuccinimide) or $CuBr_2$, but not always limited thereto.

The base herein can be selected from the group consisting of such organic bases as N,N-dimethylaminopyridine (DMAP), pyridine, triethylamine, N,N-diisopropylethylamine and 1,8-diazabicyclo[5.4.0]-7-undecene (DBU), and such inorganic bases as sodium bicarbonate, sodium hydroxide and potassium hydroxide. The selected base can be used in an equivalent amount or excessive amount, alone or in combination. In the present invention, DIPEA was used, but not always limited thereto.

The solvent usable in the reaction is exemplified by ether solvents such as tetrahydrofuran, dioxane and 1,2-dimethoxyethane; aromatic hydrocarbon solvents such as benzene, toluene and xylene; lower alcohols such as methanol, ethanol, propanol and butanol; dimethylformamide (DMF); dimethylsulfoxide (DMSO); acetonitrile; and water, which can be used independently or in combination.

In the preparation method shown in reaction formula 4 above according to the present invention, step 4 is to prepare a compound represented by formula 19 by reacting the compound represented by formula 18 obtained in step 3 above. Particularly, this step is to prepare imidazole by cyclization reaction of the compound represented by formula 18 using $NH_4OAc$.

In this invention, step 4 was performed as in the embodiment according to the present invention, but not always limited thereto.

In the preparation method shown in reaction formula 4 above according to the present invention, step 5 is to prepare a compound represented by formula 20 by reacting the compound represented by formula 19 obtained in step 4 above.

Detailed description of step 5 is the same as step 2 of the preparation method shown in reaction formula 3.

In the preparation method shown in reaction formula 4 above according to the present invention, step 6 is to prepare a compound represented by formula 2b by reacting the compound represented by formula 20 obtained in step 5 above with a compound represented by formula 11.

Detailed description of step 6 is the same as step 4 of the preparation method shown in reaction formula 2.

The present invention also provides a pharmaceutical composition for preventing or treating HCV-related liver disease comprising the compound represented by formula 1 above, the optical isomer thereof or the pharmaceutically acceptable salt thereof as an active ingredient.

Herein, the compound represented by formula 1 of the pharmaceutical composition exhibits an antiviral effect on HCV (hepatitis C virus) or HCV mutants.

In addition, the HCV mutant can be L31V, Y93H or L31V+Y93H (double mutant), or can be a mutant showing resistance other than the above, but not always limited thereto.

The HCV-related liver disease can be one or more liver diseases selected from the group consisting of acute hepatitis C, chronic hepatitis C, cirrhosis and hepatocellular carcinoma. At this time, the HCV-related liver disease can be caused by HCV mutation.

The compounds of examples according to the present invention were confirmed to inhibit HCV of genotypes 1b, 2a and 3a at low concentrations. It was also confirmed that the compounds of the present invention inhibited L31V, Y93H and L31V+Y93H (double mutant), the resistant mutants frequently observed in genotype 1b, at low concentrations. While the conventional HCV drugs inhibited genotype 1b selectively at low concentrations, but did not inhibit types 2a and 3a, whereas the compounds of examples according to the present invention exhibited excellent antiviral performance against genotypes 1b, 2a and 3a at low concentrations (see Experimental Example and Table 5).

The pharmaceutical composition of the present invention was confirmed to inhibit L31V and Y93H (single mutants) as well as L31V+Y93H (double mutant) showing stronger resistance at low concentrations. Therefore, the pharmaceutical composition of the present invention can be effectively used as a therapeutic agent targeting not only single mutants but also double or multiple mutants, and for the prevention or treatment of HCV-related liver disease by which the problem of resistant mutation against conventional therapeutic agents is solved.

The compound represented by formula 1 or the pharmaceutically acceptable salt thereof included in the pharmaceutical composition of the present invention can be administered orally or parenterally and be used in general forms of pharmaceutical formulation, but not always limited thereto.

The formulations for oral administration are exemplified by tablets, pills, hard/soft capsules, solutions, suspensions, emulsions, syrups, granules, elixirs, and troches, etc. These formulations can include diluents (for example: lactose, dextrose, sucrose, mannitol, sorbitol, cellulose, and/or glycine) and lubricants (for example: silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by formula 1 as an active ingredient can be administered by parenterally and the parenteral administration includes subcutaneous injection, intravenous injection, intramuscular injection, or intrathoracic injection.

To prepare the biphenyldiamide derivative represented by formula 1 or the pharmaceutically acceptable salt thereof as a formulation for parenteral administration, the biphenyldiamide derivative represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by formula 1 as an active ingredient can be determined according to age, weight, gender, administration method, health condition, and severity of disease. Preferably, the dosage can be 0.01~200 Ng/kg/day, which can be administered orally or parenterally once or several times a day, preferably once to three times a day at intervals of a certain time depending on the judgment of a doctor or a pharmacist.

In addition, the present invention provides a health functional food composition for preventing or ameliorating HCV-related liver disease comprising the compound represented by formula 1 above, the optical isomer thereof or the pharmaceutically acceptable salt thereof as an active ingredient.

Herein, the compound represented by formula 1 of the health functional food composition exhibits an antiviral effect on HCV (hepatitis C virus) or HCV mutants.

In addition, the HCV mutant can be L31V, Y93H or L31V+Y93H (double mutant), or can be a mutant showing resistance other than the above, but not always limited thereto.

The HCV-related liver disease can be one or more liver diseases selected from the group consisting of acute hepatitis C, chronic hepatitis C, cirrhosis and hepatocellular carcinoma. At this time, the HCV-related liver disease can be caused by HCV mutation.

In order to prevent or ameliorate liver disease caused by HCV, the compound represented by formula 1, the sitologically acceptable salt thereof or the optical isomer thereof can be added to a health functional food such as food and beverage.

For example, the above-mentioned substances can be added to drinks, meat, sausages, bread, biscuits, rice cakes, chocolates, candies, snacks, cookies, pizza, ramen, other noodles, gums, dairy products including ice cream, various soups, beverages, alcohol drinks and vitamin complex, dairy foods and dairy products, etc., and in wide sense, almost every food applicable in the production of health food can be included.

The compound represented by formula 1 according to the present invention, the sitologically acceptable salt thereof or the optical isomer thereof can be added to food as it is or as mixed with other food components according to the conventional method. The mixing ratio of active ingredients can be regulated according to the purpose of use (prevention or amelioration). In general, the compound of the present invention is preferably added to food or beverages by 0.1~90 weight part for the total weight of the food or beverages. However, if long term administration is required for health and hygiene or regulating health condition, the content can be lower than the above but higher content can be accepted as well since the compound of the present invention has been proved to be very safe.

The health functional beverage of the present invention is not particularly limited to other ingredients except for containing the compound as an essential ingredient at the indicated ratio, and can contain various flavors or natural carbohydrates as additional ingredients, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (for example: thaumatin, stevia extract, etc.) and synthetic sweetening agents (for example: saccharin, aspartame, etc.) can be included as a sweetening agent. The content of the natural carbohydrate is preferably 1~20 g and more preferably 5~12 g in 100 g of the health functional composition of the present invention.

In addition to the ingredients mentioned above, the health functional food composition comprising the compound represented by formula 1 according to the present invention, the sitologically acceptable salt thereof or the optical isomer thereof as an active ingredient can include in variety of nutrients, vitamins, minerals (electrolytes), flavors including natural flavors and synthetic flavors, coloring agents and extenders (for example: cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The health functional food composition of the present invention can also include natural fruit juice, fruit beverages and fruit flesh addable to vegetable beverages.

All the mentioned ingredients can be added singly or together. The mixing ratio of those ingredients does not matter in fact, but in general, each can be added by 0.1-20 weight part per 100 weight part of the health functional food composition of the present invention.

The present invention also provides a method for preventing or treating HCV-related liver disease, which comprises the step of administering a pharmaceutical composition or a health functional food composition comprising the compound represented by formula 1 above, the isomer thereof, the solvate thereof, the hydrate thereof or the pharmaceutically acceptable salt thereof as an active ingredient to a subject in need.

In addition, the present invention provides a use of the pharmaceutical composition or the health functional food composition comprising the compound represented by formula 1 above, the isomer thereof, the hydrate thereof or the pharmaceutically acceptable salt thereof in the prevention or treatment of HCV-related liver disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Preparation of dimethyl ((1R,1'R)-((2S,2'S)-(((9,9-dipropyl-9H-fluorene-2,7-diyl)bis(azanediyl))bis(carbonyl)bis(pyrrolidine-2,1-diyl)bis(2-oxo-1-phenylethane-2,1-diyl))dicarbamate

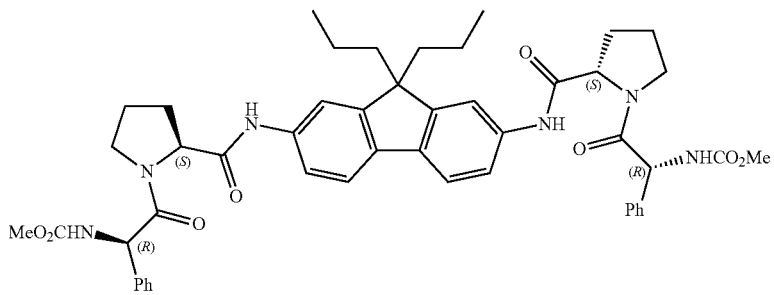

Step 1: Preparation of 9,9-dipropyl-2-nitro-9H-fluorene

DMF (100 mL) mixture containing 2,7-dinitrofluorene (10.0 g, 39.0 mmol) and $Cs_2CO_3$ (51.4 g, 117 mmol) was stirred at 0° C. in argon atmosphere. After 20 minutes, 1-iodopropane (10.7 mL, 93.7 mmol) was added thereto dropwise using a syringe, and the reaction mixture was stirred overnight while slowly raising the temperature to room temperature. The reactant was quenched with water and the water layer was extracted with EtOAc. The organic layer was washed with brine, dried over $MgSO_4$, filtered, and concentrated under reduced pressure. Silica gel mesh was prepared from the residue, and flash chromatography (eluent: EtOAc/hexane) was performed to give 9,9-dipropyl-2-nitro-9H-fluorene (11.29 g, 85%).

$^1$H-NMR (DMSO-$d_6$, δ=2.5 ppm, 400 MHz): 8.41 (s, 2H), 8.30-8.24 (m, 4H), 2.17 (t, 4H), 0.98 (m, 4H), 0.56 (t, 6H), 0.37 (m, 4H).

Step 2: Preparation of 9,9-dipropyl-9H-fluorene-2,7-diamine

Magnetic bar, $Fe_3O_4$ (119 mg, 0.514 mmol) and DMF (20 mL) were placed in a two-necked 100 mL round-bottom flask dried in an oven and the mixture was sonicated in an ultrasound bath for 1 minute in argon atmosphere. The compound obtained in step 1 (874 mg, 2.57 mmol) and hydrazine monohydrate (1.00 mL, 20.5 mmol) were added to the mixture, which was stirred at 80° C. in argon atmosphere until all the compound obtained in step 1 was exhausted. After magnetic separation of $Fe_3O_4$, the reaction mixture was diluted with water and extracted with EtOAc. The organic layer was washed with brine, dried over $MgSO_4$, filtered and concentrated in vacuo, from which 9,9-dipropyl-9H-fluorene-2,7-diamine (668 mg, 93%) was obtained without further purification.

Step 3: Preparation of (2S,2'S)-di-tert-butyl-2,2'-(((9,9-dipropyl-9H-fluorene-2,7-diyl)bis(azandiyl))bis(carbonyl))bis(pyrrolidine-1-carboxylate)

$CH_2Cl_2$ (0.5 mL) mixture containing N-Boc-L-proline (35 mg, 0.160 mmol), EDCI (1-ethyl-3-(3-dimethylaminopropyl)carbodiimide) (31 mg, 0.160 mmol), DIPEA (N,N-diisopropylethylamine) (56 μL, 0.321 mmol) and the compound obtained in step 2 (18 mg, 0.064 mmol) was stirred overnight at room temperature. The reaction residue was divided into $CH_2Cl_2$ layer and $H_2O$ layer, and then the organic layer was washed with 0.1 N HCl (aq) and brine, dried over $MgSO_4$, filtered, and concentrated in vacuo. Silica gel mesh was prepared from the residue, and flash chromatography (eluent: EtOAc/hexane) was performed to give (2S,2'S)-di-tert-butyl 2,2'-(((9,9-dipropyl-9H-fluorene-2,7-diyl)bis(azandiyl))bis(carbonyl))bis(pyrrolidine-1-carboxylate) (23 mg, 53%).

$^1$H-NMR (DMSO-$d_6$, δ=2.5 ppm, 400 MHz):

Step 4: Preparation of dimethyl ((1R,1'R)-((2S,2'S)-(((9,9-dipropyl-9H-fluorene-2,7-diyl)bis(azanediyl))bis(carbonyl))bis(pyrrolidine-2,1-diyl))bis(2-oxo-1-phenylethane-2,1-diyl))dicarbamate 2N HCl dioxane solution (0.5 mL) containing the (2S,2'S)-di-tert-butyl (2S,2'S)-di-tert-butyl 2,2'-(((9,9-dipropyl-9H-fluorene-2,7-diyl)bis(azandiyl))bis(carbonyl))bis(pyrrolidine-1-carboxylate) (19 mg, 0.040 mmol) obtained in step 3 above was stirred at room temperature for 2 hours. After the volatile elements were removed under reduced pressure, EDCI (19 mg, 0.100 mmol) and (R)-2-((methoxycarbonyl)amino)-2-phenylacetic acid (21 mg, 0.100 mmol) were added to $CH_2Cl_2$ (0.5 mL) solution containing DIPEA (35 μL, 0.200 mmol) for 4 minutes. The reaction mixture was stirred at room temperature for 18 hours. The residue was divided into $CH_2Cl_2$ layer and $H_2O$ layer, and then the organic layer was washed with $H_2O$ and brine, dried over $MgSO_4$, filtered, and concentrated in vacuo. Silica gel mesh was prepared from the residue, and flash chromatography (eluent: EtOAc/hexane) was performed to give a target compound (53%).

$^1$H-NMR (DMSO-$d_6$, δ=2.5 ppm, 400 MHz):

<Example 2> Preparation of dimethyl ((1R,1'R)-((2S,2'S)-(((9,9-dibutyl-9H-fluorene-2,7-diyl)bis(azanediyl))bis(carbonyl))bis(pyrrolidine-2,1-diyl))bis(2-oxo-1-phenylethane-2,1-diyl))dicarbamate

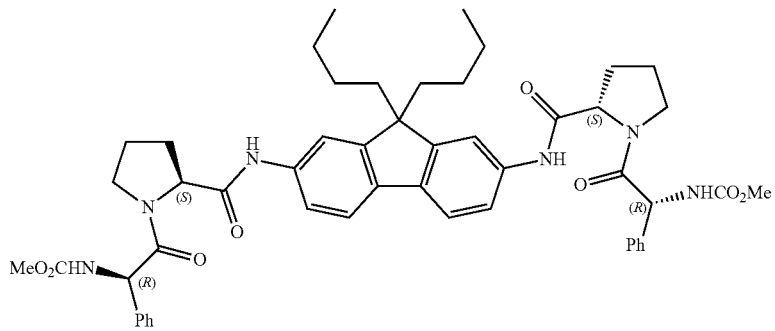

Step 1: Preparation of 9,9-dibutyl-2,7-dinitro-9H-fluorene $Cs_2CO_3$ was added to DMF (dimethylformamide) (100 mL) containing 2,7-dinitrofluorene (10.0 g, 39.0 mmol) at 0° C. in argon atmosphere. After 20 minutes, 1-iodobutane (11.1 mL, 97.6 mmol) was added to the reaction mixture dropwise using a syringe. The reactant was quenched with water and the water layer was extracted with EtOAc. The organic layer was washed with brine, dried over $MgSO_4$, filtered, and concentrated in vacuo. Silica gel mesh was prepared from the residue, and flash chromatography (eluent: EtOAc/hexane) was performed to give 9,9-dibutyl-2,7-dinitro-9H-fluorene (6.18 g, 47%).

$^1$H-NMR (DMSO-$d_6$, δ=2.5 ppm, 400 MHz): 8.41 (s, 2H), 8.30-8.24 (m, 4H), 2.17 (t, 4H), 0.98 (m, 4H), 0.56 (t, 6H), 0.37 (m, 4H).

Step 2: Preparation of 9,9-dibutyl-9H-fluorene-2,7-diamine

Magnetic bar, $Fe_3O_4$ (843 mg, 3.64 mmol) and DMF (110 mL) were placed in a two-necked 250 mL round-bottom flask dried in an oven and the mixture was sonicated in an ultrasound bath for 1 minute. The compound obtained in step 1 (6.18 g, 18.2 mmol) and hydrazine monohydrate (7.08 mL, 146 mmol) were added to the mixture, which was stirred at 80° C. in argon atmosphere until all the compound obtained in step 1 was exhausted. After magnetic separation of $Fe_3O_4$, the reaction mixture was diluted with water and extracted with EtOAc. The organic layer was washed with brine, dried over $MgSO_4$, filtered and concentrated in vacuo, from which 9,9-dibutyl-9H-fluorene-2,7-diamine (5.57 g, 99%) was obtained without further purification.

$^1$H-NMR (DMSO-$d_6$, δ=2.5 ppm, 400 MHz): 7.15 (d, 2H), 6.49 (d, 2H), 6.42 (dd, 2H), 4.87 (s, 4H), 1.73 (m, 4H), 1.02 (td, 4H), 0.64 (t, 6H), 0.52 (m, 4H).

Step 3: Preparation of (2S,2'S)-di-tert-butyl 2,2'-(((9,9-dibutyl-9H-fluorene-2,7-diyl)bis(azandiyl))bis(carbonyl))bis(pyrrolidine-1-carboxylate)

(2S,2'S)-di-tert-butyl 2,2'-(((9,9-dibutyl-9H-fluorene-2,7-diyl)bis(azandiyl))bis(carbonyl))bis(pyrrolidine-1-carboxylate) (9.60 g, 86%) was obtained by the same manner as described in step 3 of Example 1 above.

$^1$H-NMR (DMSO-$d_6$, δ=2.5 ppm, 400 MHz): 10.03 (s, 2H), 7.76 (s, 1H), 7.63 (m, 4H), 7.48 (d, 1H), 4.29-4.17 (m, 2H), 3.41 (m, 2H), 3.34 (m, 2H), 2.20 (m, 2H), 1.92-1.78 (m, 10H), 1.40 (s, 6H), 1.24 (s, 12H), 1.01 (m, 4H), 0.60 (m, 6H), 0.50 (m, 4H).

Step 4: Preparation of dimethyl ((1R,1'R)-((2S,2'S)-(((9,9-dibutyl-9H-fluorene-2,7-diyl)bis(azanediyl))bis(carbonyl))bis(pyrrolidine-2,1-diyl))bis(2-oxo-1-phenylethane-2,1-diyl))dicarbamate A target compound (3.49 g, 53%) was obtained by the same manner as described in step 4 of Example 3.

$^1$H-NMR (DMSO-$d_6$, δ=2.5 ppm, 400 MHz): 10.30-9.96 (m, 2H), 7.74-7.51 (m, 8H), 7.42-7.30 (m, 10H), 5.52 (d, 2H), 4.43 (d, 2H), 3.82 (m, 2H), 3.55 (s, 6H), 3.19 (m, 2H), 1.99-1.79 (m, 12H), 1.05 (m, 4H), 0.64 (m, 6H), 0.52 (m, 4H).

<Example 3> Preparation of methyl ((S)-1-((S)-2-(5-(9,9-dipropyl-7-((S)-1-((R)-2-((methoxycarbonyl)amino)-2-phenylacetyl)pyrrolidine-2-carboxamido)-9H-fluoren-2-yl)-1H-imidazole-2-yl)pyrrolidine-1-yl)-3-methyl-1-oxobutane-2-yl)carbamate

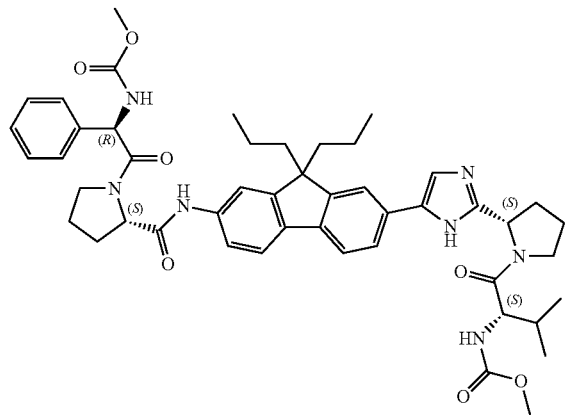

Step 1: Preparation of 2-nitro-9,9-dipropyl-9H-fluorene

DMF (50 mL) containing 2-nitro-9H-fluorene (3 g, 14.2 mmol) and $Cs_2CO_3$ (13.9 g, 42.6 mmol) was stirred at 0° C. for 30 minutes in argon atmosphere. Bromopropane (3.10 mL, 34.1 mmol) was added to the reaction mixture, which was stirred overnight at room temperature. The reactant was quenched with water and the water layer was extracted with EtOAc. The organic layer was washed with brine, dried over $MgSO_4$, filtered, and concentrated in vacuo. Silica gel mesh was prepared from the residue, and flash chromatography (eluent: EtOAc/hexane) was performed to give 9,9-diethyl-2-nitro-9H-fluorene (2.99 g, 71%).

Step 2: Preparation of 1-(7-nitro-9,9-dipropyl-9H-fluoren-2-yl)ethane-1-one $AlCl_3$ (1.89 g, 14.2 mmol) was added to anhydrous $CH_2Cl_2$ (20 mL) containing 9,9-dipropyl-2-nitro-9H-fluorene (2.99 g, 10.1 mmol) obtained in step 1 above at room temperature in argon atmosphere. The temperature of the reaction mixture was raised to 40° C. Acetyl chloride (865 uL, 12.2 mmol) was added dropwise to the solution. The reaction mixture was stirred overnight. The reactant was quenched with 10% HCl (aq) and stirred at 0° C. for 10 minutes. The reactant was separated into two layers and the water layer was extracted with $CH_2Cl_2$. The combined organic layer was washed with saturated $NaHCO_3$ (aq), dried over $MgSO_4$, filtered and concentrated in vacuo. Silica gel mesh was prepared from the residue, and flash chromatography (eluent: EtOAc/hexane) was performed to give 1-(7-nitro-9,9-dipropyl-9H-fluoren-2-yl)ethane-1-one (2.04 g, 60%).

$^1$H-NMR (CDCl$_3$, δ=7.26 ppm, 400 MHz,): 8.24-8.19 (m, 2H), 7.99 (s, 1H), 7.96 (s, 1H), 7.85-7.82 (dd, 2H), 2.64 (s, 3H), 2.03-2.00 (t, 4H), 0.60-0.52 (m, 10H).

Step 3: Preparation of (S)-1-tert-butyl 2-(2-(7-nitro-9,9-dipropyl-9H-fluoren-2-yl)-2-oxoethyl) pyrrolidine-1,2-dicarboxylate Ethyl acetate (10 mL)/chloroform (10 mL) containing 1-(7-nitro-9,9-dipropyl-9H-fluoren-2-yl)ethane-1-one (2.04 g, 6.04 mmol) obtained in step 2 and cooper (II) bromide (1.62 g, 7.25 mmol) was heated and refluxed for 8 hours. The mixture was filtered to remove cooper (II) bromide. The filtrate was concentrated in vacuo to give a yellow solid. The crude reaction mixture was dissolved in ACN (acetonitrile) (16 mL), to which N-Boc-L-proline (2.55 g, 11.8 mmol) and DIPEA (2.40 mL, 13.8 mmol) were added. The mixture was stirred at room temperature until the starting material disappeared. The volatile elements were evaporated under reduced pressure and the residue was divided into EtOAc layer and water layer. The organic layer was washed with brine, dried over $MgSO_4$, filtered, and concentrated in vacuo. Column chromatography (eluent: EtOAc/hexane) was performed with the residue to give (S)-1-tert-butyl 2-(2-(7-nitro-9,9-dipropyl-9H-fluoren-2-yl)-2-oxoethyl) pyrrolidine-1,2-dicarboxylate (2.2 g, yield of step 2: 96%).

Step 4: Preparation of (S)-tert-butyl 2-(5-(7-nitro-9,9-dipropyl-9H-fluoren-2-yl)-1H-imidazole-2-yl) pyrrolidine-1-carboxylate 1-(Tert-butyl) 2-(2-(7-nitro-9,9-dipropyl-9H-fluoren-2-yl)-2-oxoethyl) (S)-pyrrolidine-1,2-dicarboxylate (2.67 g, 4.85 mmol) obtained in step 3 above, NH₄OAc (5.61 g, 72.8 mmol) and toluene (20 mL) were added to a sealed tube, which was heated at 90° C. for 20 hours. The volatile elements were removed in vacuo and the residue was divided into EtOAc layer and water layer. The organic layer was separated and the water layer was further extracted with EtOAc. The combined organic layer was washed with brine, dried over MgSO₄, filtered and concentrated in vacuo. Column chromatography (eluent: EtOAc/hexane) was performed with the residue to give (S)-tert-butyl 2-(5-(7-nitro-9,9-dipropyl-9H-fluoren-2-yl)-1H-imidazole-2-yl)pyrrolidine-1-carboxylate (1.37 g, 81%).

Step 5: Preparation of methyl ((S)-3-methyl-1-((S)-2-(5-(7-nitro-9,9-dipropyl-9H-fluorene-2-yl)-1H-imidazole-2-yl)pyrrolidine-1-yl)-1-oxobutane-2-yl)carbamate (S)-tert-butyl 2-(5-(7-nitro-9,9-dipropyl-9H-fluorene-2-yl)-1H-imidazole-2-yl)pyrrolidine-1-carboxylate (1.37 g, 2.58 mmol) obtained in step 4 above and 2N HCl dioxane (20 mL) were stirred at room temperature for 2 hours. The volatile elements were removed in vacuo and the reaction residue was dissolved in CH₂Cl₂ (10 mL). EDCI (1.29 g, 6.71 mmol), HOBt (906 mg, 6.71 mmol), (methoxycarbonyl)-L-valine (1.08 g, 6.19 mmol) and DIPEA (2.25 mL, 12.9 mmol) were added to the solution. The reaction mixture was stirred overnight at room temperature. The residue was divided into CH₂Cl₂ layer and H₂O layer. The organic layer was washed with H₂O and brine, dried over MgSO₄, filtered, and concentrated in vacuo. Silica gel mesh was prepared from the residue, and flash chromatography (eluent: EtOAc/hexane) was performed to give methyl ((S)-3-methyl-1-((S)-2-(5-(7-nitro-9,9-dipropyl-9H-fluorene-2-yl)-1H-imidazole-2-yl)pyrrolidine-1-yl)-1-oxobutane-2-yl)carbamate (1.12 g, 74%).

Step 6: Preparation of methyl ((S)-1-((S)-2-(5-(7-amino-9,9-dipropyl-9H-fluorene-2-yl)-1H-imidazole-2-yl)pyrrolidine-1-yl)-3-methyl-1-oxobutane-2-yl)carbamate Methyl ((S)-1-((S)-2-(5-(7-amino-9,9-dipropyl-9H-fluorene-2-yl)-1H-imidazole-2-yl)pyrrolidine-1-yl)-3-methyl-1-oxobutane-2-yl)carbamate (806 mg, 76%) was obtained by the same manner as described in step 2 of Example 4.

Step 7: Preparation of (S)-tert-butyl 2-((7-(2-((S)-1-((S)-2-((methoxycarbonyl)amino)-3-methylbutanoyl)pyrrolidine-2-yl)-1H-imidazole-5-yl)-9,9-dipropyl-9H-fluorene-2-yl)carbamoyl)pyrrolidine-1-carboxylate (S)-tert-butyl 2-((7-(2-((S)-1-((S)-2-(793 mg, 99%) was obtained by the same manner as described in step 4 of Example 3.
LC/MS: Anal. Calcd. For [M+H]⁺: C43H59N6O6: 755.4; found 755.4.

Step 8: Preparation of methyl ((S)-1-((S)-2-(5-(9,9-dipropyl-7-((S)-1-((R)-2-((methoxycarbonyl)amino)-2-phenylacetyl)pyrrolidine-2-carboxyamido)-9H-fluorene-2-yl)-1H-imidazole-2-yl)pyrrolidine-1-yl)-3-methyl-1-oxobutane-2-yl)carbamate A target compound (718 mg, 85%) was obtained by the same manner as described in step 5 of Example 3.
LC/MS: Anal. Calcd. For [M+H]⁺: C48H60N7O7: 846.5; found 846.4.

The compounds of Examples 1 to 42 of the present invention were prepared by the same method as any one of Examples 1-3, and the chemical structures and analytical data (NMR or LC/MS) of the compounds of Examples are shown in Tables 1 to 4 below.

TABLE 1

| Example | Chemical Structure | Compound Name | NMR or LC/MS |
|---|---|---|---|
| 1 | 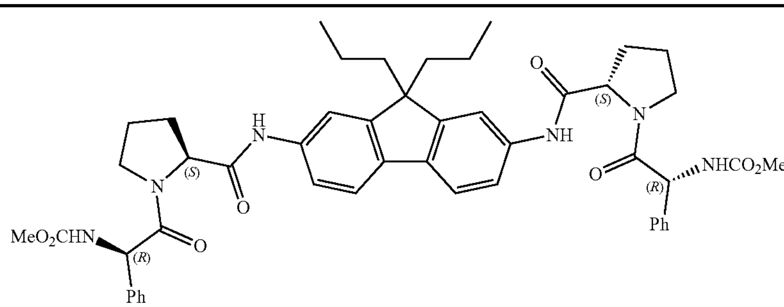 | dimethyl ((1R,1'R)-((2S,2'S)-(((9,9-dipropyl-9H-fluorene-2,7-diyl)bis (azanediyl)) bis(carbonyl)) bis(pyrrolidine-2,1-diyl))bis(2-oxo-1-phenylethane-2,1-diyl)) dicarbamate | LC/MS: Anal. Calcd. For [M + H]⁺: C49H57N6O8: 857.4; found 857.3 |

TABLE 1-continued

| Example | Chemical Structure | Compound Name | NMR or LC/MS |
|---|---|---|---|
| 2 | 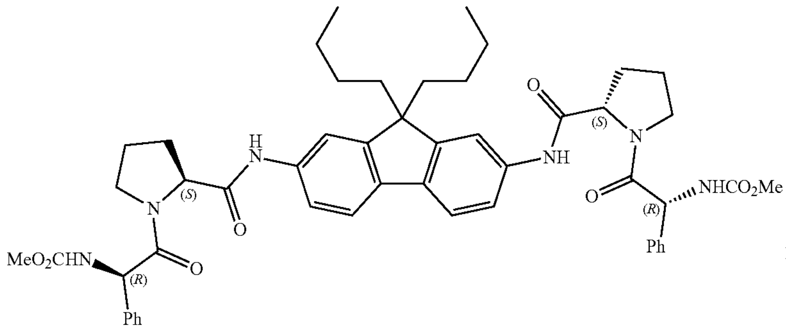 | dimethyl ((1R,1'R)-((2S,2'S)-(((9,9-dibutyl-9H-fluorene-2,7-diyl)bis(azanediyl))bis(carbonyl))bis(pyrrolidine-2,1-diyl))bis(2-oxo-1-phenylethane-2,1-diyl))dicarbamate | $^1$H-NMR (DMSO-$d_6$, δ ppm, 400 MHz): 10.30-9.96 (m, 2H), 7.74-7.51 (m, 8H), 7.42-7.30 (m, 10H), 5.52 (d, 2H), 4.43 (d, 2H), 3.82 (m, 2H), 3.55 (s, 6H), 3.19 (m, 2H), 1.99-1.79 (m, 12H), 1.05 (m, 4H), 0.64 (m, 6H), 0.52 (m, 4H). LC/MS: Anal. Calcd. For [M + H]$^+$: C51H61N6O8: 885.5; found 885.4 |
| 3 | 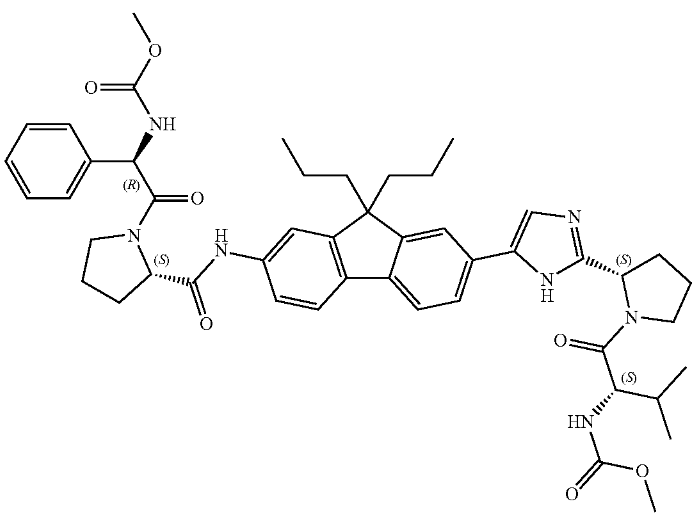 | methyl ((S)-1-((S)-2-(5-(9,9-dipropyl-7-((S)-1-((R)-2-((methoxycarbonyl)amino)-2-phenylacetyl)pyrrolidine-2-carboxyamido)-9H-fluoren-2-yl)-1H-imidazole-2-yl)pyrrolidine-1-yl)-3-methyl-1-oxobutane-2-yl)carbamate | LC/MS: Anal. Calcd. For [M + H]$^+$: C48H60N7O7: 846.5; found 846.4 |
| 4 | 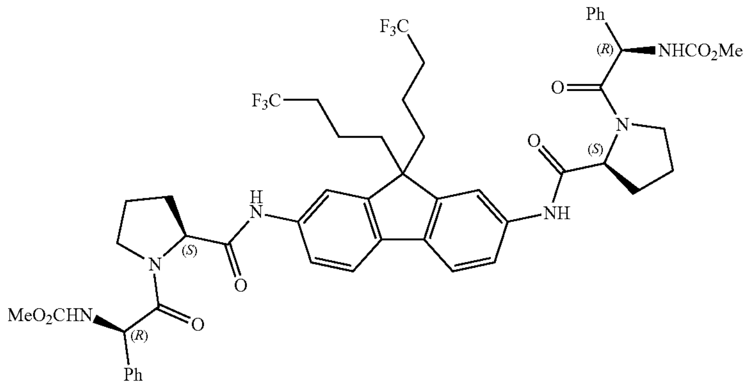 | dimethyl ((1R,1'R)-((2S,2'S)-(((9,9-bis(4,4,4-trifluorobutyl)-9H-fluorene-2,7-diyl)bis(azanediyl))bis(carbonyl))bis(pyrrolidine-2,1-diyl))bis(2-oxo-1-phenylethane-2,1-diyl))dicarbamate | LC/MS: Anal. Calcd. For [M + H]$^+$: $C_{51}H_{55}F_6N_6O_8^+$: 993.4; found 993.3. |

TABLE 1-continued

| Example | Chemical Structure | Compound Name | NMR or LC/MS |
|---|---|---|---|
| 5 | 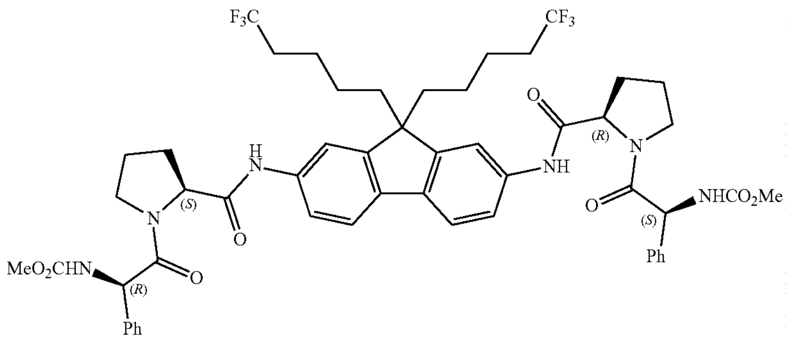 | methyl ((R)-2-((S)-2-((7-((R)-1-((S)-2-((methoxycarbonyl)amino)-2-phenylacetyl)pyrrolidine-2-carboxyamido)-9,9-bis(5,5,5-trifluoropentyl)-9H-fluorene-2-yl)carbamoyl)pyrrolidine-1-yl)-2-oxo-1-phenylethyl)carbamate | LC/MS: Anal. Calcd. For [M + H]$^+$: C$_{53}$H$_{59}$F$_6$N$_6$O$_8$$^+$: 1021.4; found 1021.3. |
| 6 | 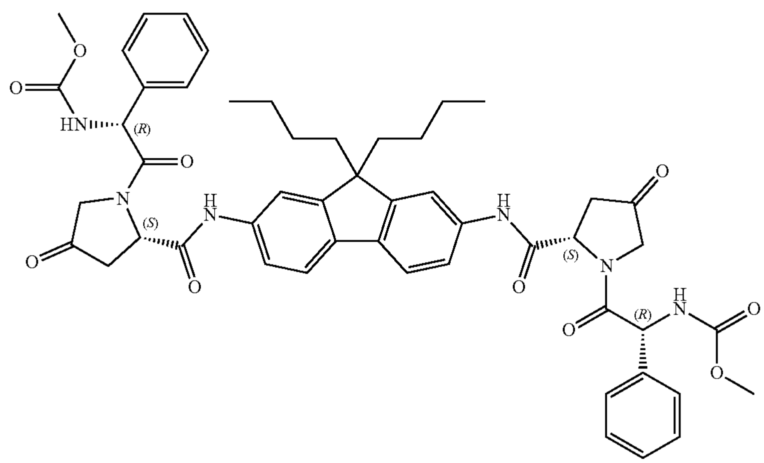 | dimethyl ((1R,1'R)-((5S,5'S)-(((9,9-dibutyl-9H-fluorene-2,7-diyl)bis(azanediyl))bis(carbonyl))bis(3-oxopyrrolidine-5,1-diyl))bis(2-oxo-1-phenylethane-2,1-diyl))dicarbamate | LC/MS: Anal. Calcd. For [M + H]$^+$: C51H56N6O10: 913.4; found 913.3 |
| 7 | 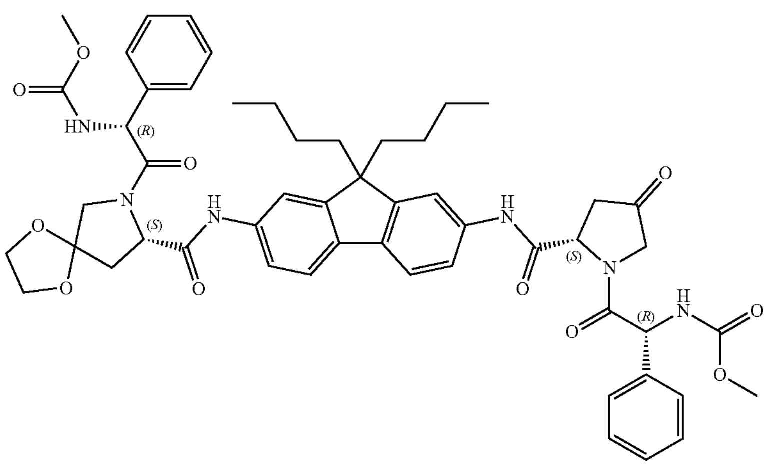 | methyl ((R)-2-((S)-8-((9,9-dibutyl-7-((S)-1-((R)-2-((methoxycarbonyl)amino)-2-phenylacetyl)-4-oxopyrrolidine-2-carboxyamido)-9H-fluorene-2-yl)carbamoyl)-1,4-dioxa-7-azaspiro[4.4]nonane-7-yl)-2-oxo-1-phenylethyl)carbamate | LC/MS: Anal. Calcd. For [M + H]$^+$: C53H61N6O11: 957.4; found 957.5 |

TABLE 1-continued

| Example | Chemical Structure | Compound Name | NMR or LC/MS |
|---|---|---|---|
| 8 | 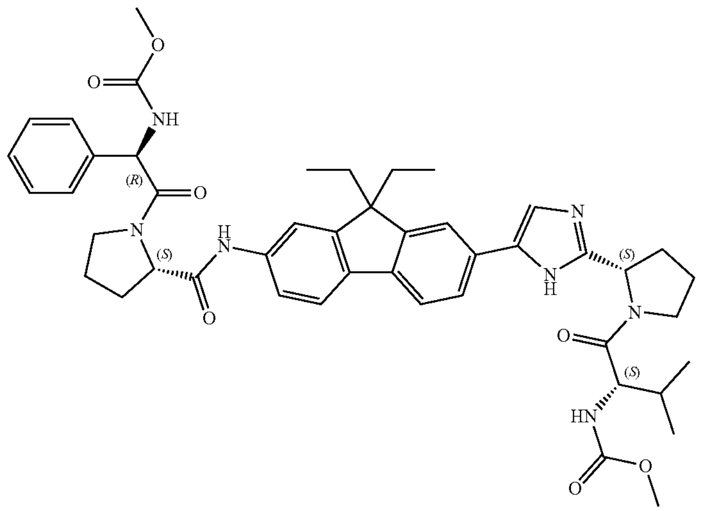 | methyl ((S)-1-((S)-2-(5-(9,9-diethyl-7-((S)-1-((R)-2-((methoxycarbonyl)amino)-2-phenylacetyl)pyrrolidine-2-carboxyamido)-9H-fluorene-2-yl)-1H-imidazole-2-yl)pyrrolidine-1-yl)-3-methyl-1-oxobutane-2-yl)carbamate | LC/MS: Anal. Calcd. For [M + H]+ C46H55N7O7: 818.4; found 818.4. |
| 9 | 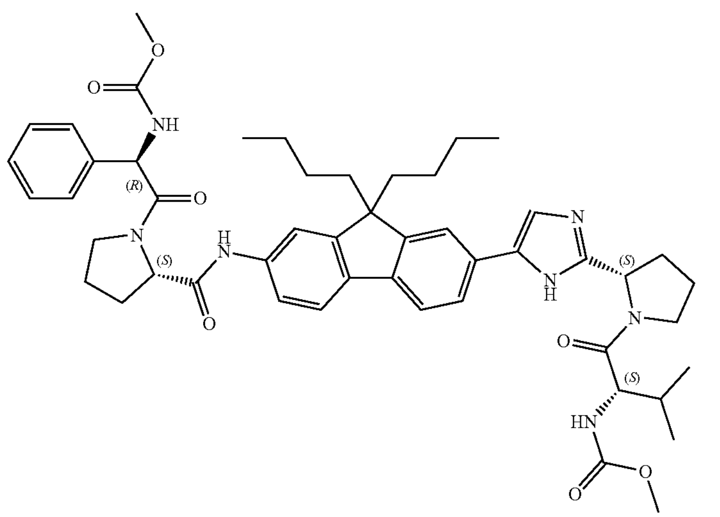 | methyl ((S)-1-((S)-2-(5-(9,9-dibutyl-7-((S)-1-((R)-2-((methoxycarbonyl)amino)-2-phenylacetyl)pyrrolidine-2-carboxyamido)-9H-fluorene-2-yl)-1H-imidazole-2-yl)pyrrolidine-1-yl)-3-methyl-1-oxobutane-2-yl)carbamate | LC/MS: Anal. Calcd. For [M + H]+ C50H64N7O7: 874.5; found 874.4. |
| 10 | 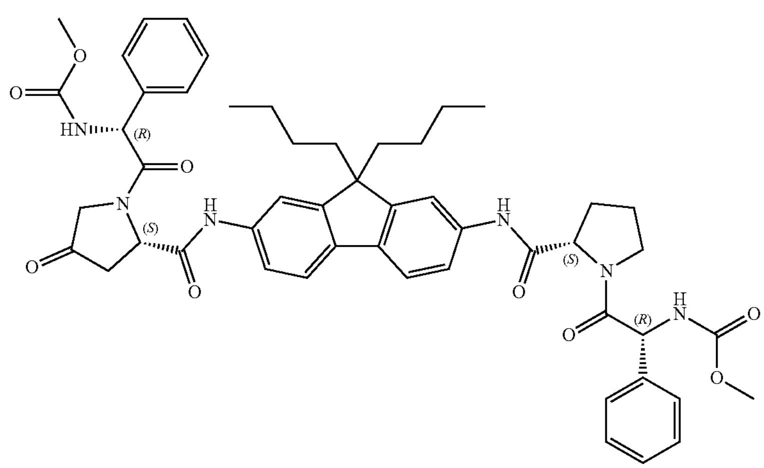 | methyl ((R)-2-((S)-2-((9,9-dibutyl-7-((S)-1-((R)-2-((methoxycarbonyl)amino)-2-phenylacetyl)pyrrolidine-2-carboxyamido)-9H-fluorene-2-yl)carbamoyl)-4-oxopyrrolidine-1-yl)-2-oxo-1-phenylethyl)carbamate | LC/MS: Anal. Calcd. For [M + H]+: C51H59N6O9: 900.1; found 900.2 |

TABLE 2

| Example | Chemical Structure | Compound Name | NMR or LC/MS |
|---|---|---|---|
| 11 | 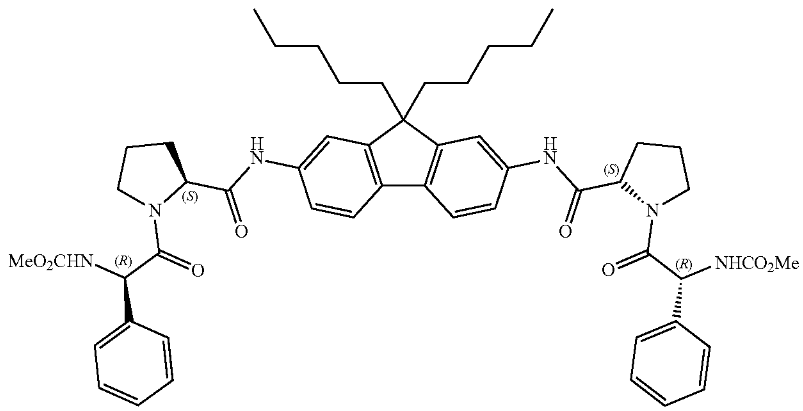 | dimethyl ((1R,1'R)-((2S,2'S)-(((9,9-dipentyl-9H-fluorene-2,7-diyl)bis(azanediyl))bis(carbonyl))bis(pyrrolidine-2,1-diyl))bis(2-oxo-1-phenylethane-2,1-diyl))dicarbamate | 1H-NMR (DMSO-d$_6$, δ ppm, 400 MHz): 10.30-9.96 (m, 2H), 7.74-7.51 (m, 8H), 7.42-7.30 (m, 10H), 5.52 (d, 2H), 4.43 (d, 2H), 3.82 (m, 2H), 3.55 (s, 6H), 3.19 (m, 2H), 1.99-1.79 (m, 12H), 1.05 (m, 4H), 0.64 (m, 6H), 0.52 (m, 4H). LC/MS: Anal. Calcd. For [M + H]$^+$: C53H65N6O8: 913.5; found 913.3 |
| 12 | 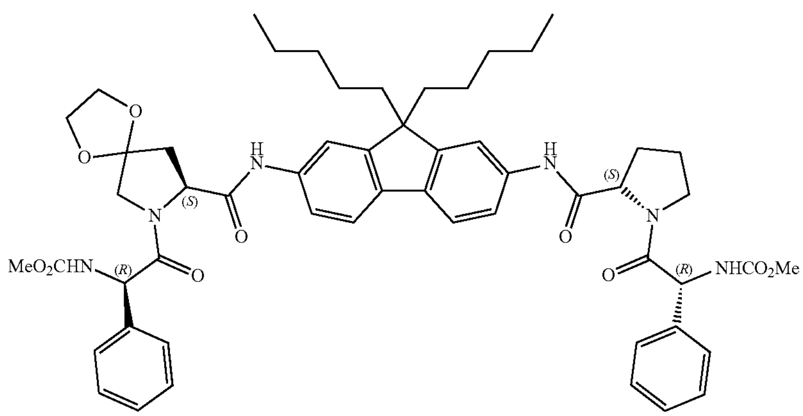 | methyl ((R)-2-((S)-2-((7-((S)-7-((R)-2-((methoxycarbonyl)amino)-2-phenylacetyl)-1,4-dioxa-7-azaspiro[4.4]nonane-8-carboxamido)-9,9-dipentyl-9H-fluoren-2-yl)carbamoyl)pyrrolidin-1-yl)-2-oxo-1-phenylethyl)carbamate | LC/MS: Anal. Calcd. For [M + H]$^+$: C55H67N6O10: 971.5; found 971.4 |
| 13 | 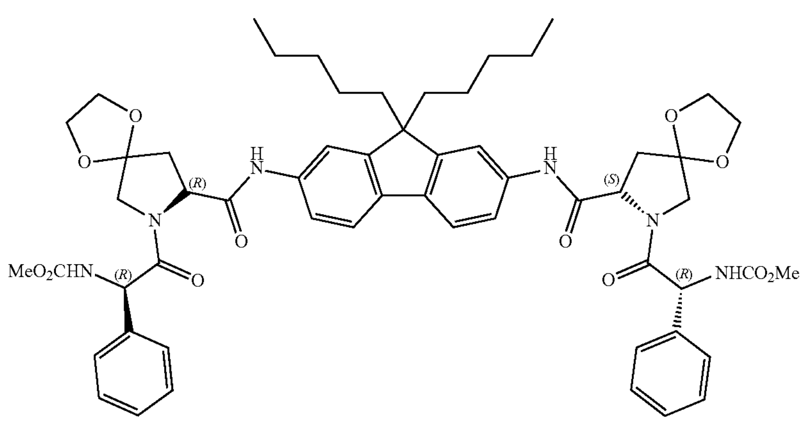 | dimethyl ((1R,1'R)-((8S,8'S)-(((9,9-dipentyl-9H-fluorene-2,7-diyl)bis(azanediyl))bis(carbonyl))bis(1,4-dioxa-7-azaspiro[4.4]nonane-8,7-diyl))bis(2-oxo-1-phenylethane-2,1-diyl))dicarbamate | LC/MS: Anal. Calcd. For [M + H]$^+$: C57H69N6O12: 1029.5; found 1029.5 |

TABLE 2-continued

| Example | Chemical Structure | Compound Name | NMR or LC/MS |
|---|---|---|---|
| 14 | 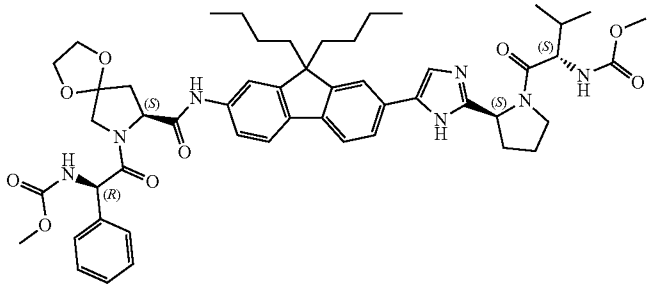 | methyl ((S)-1-((S)-2-(5-(9,9-dibutyl-7-((S)-7-((R)-2-((methoxycarbonyl)amino)-2-phenylacetyl)-1,4-dioxa-7-azaspiro[4.4]nonane-8-carboxyamido)-9H-fluoren-2-yl)-1H-imidazole-2-yl)pyrrolidine-1-yl)-3-methyl-1-oxobutane-2-yl)carbamate | LC/MS: Anal. Calcd. For [M + H]⁺: C52H66N7O9: 932.5; found 932.1 |
| 15 | 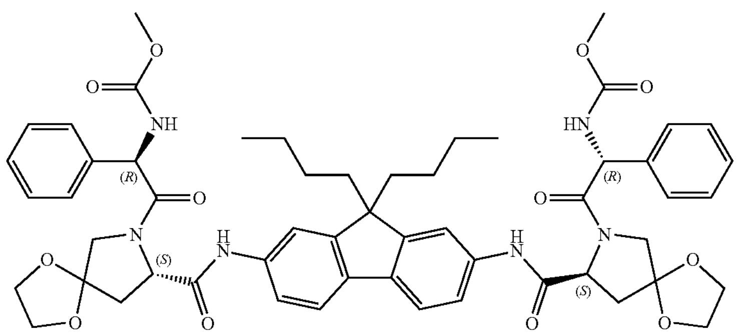 | dimethyl ((1R,1'R)-((8S,8'S)-(((9,9-dibutyl-9H-fluorene-2,7-diyl)bis(azanediyl))bis(carbonyl))bis(1,4-dioxa-7-azaspiro[4.4]nonane-8,7-diyl))bis(2-oxo-1-phenylethane-2,1-diyl))dicarbamate | LC/MS: Anal. Calcd. For [M + H]⁺: C55H64N6NaO12: 1023.4; found 1024.1 |
| 16 | 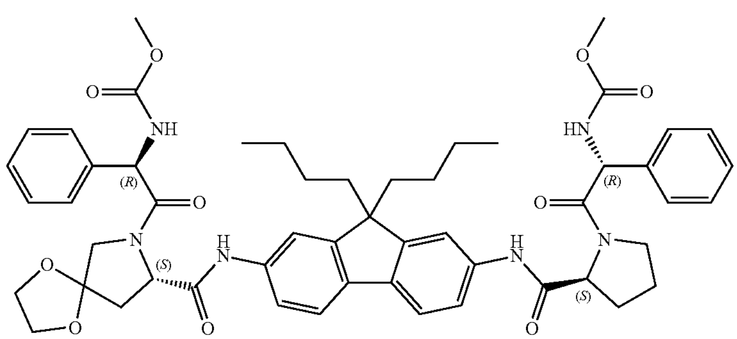 | methyl ((R)-2-((S)-8-((9,9-dibutyl-7-((S)-1-((R)-2-((methoxycarbonyl)amino)-2-phenylacetyl)pyrrolidine-2-carboxyamido)-9H-fluoren-2-yl)carbamoyl)-1,4-dioxa-7-azaspiro[4.4]nonane-7-yl)-2-oxo-1-phenylethyl)carbamate | LC/MS: Anal. Calcd. For [M + H]⁺: C53H63N6O10: 943.5; found 944.4 |
| 17 | 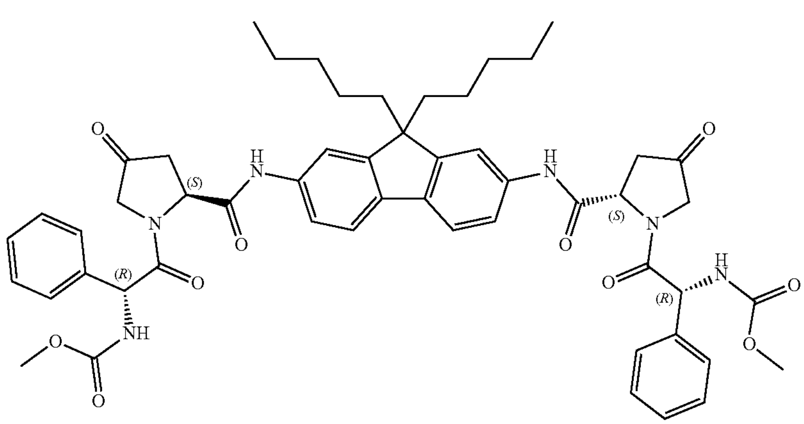 | dimethyl ((1R,1'R)-((5S,5'S)-(((9,9-dipentyl-9H-fluorene-2,7-diyl)bis(azanediyl))bis(carbonyl))bis(3-oxopyrrolidine-5,1-diyl))bis(2-oxo-1-phenylethane-2,1-diyl))dicarbamate | LC/MS: Anal. Calcd. For [M + H]⁺: C53H61N6O10: 941.4; found 941.3 |

TABLE 2-continued

| Example | Chemical Structure | Compound Name | NMR or LC/MS |
|---|---|---|---|
| 18 | 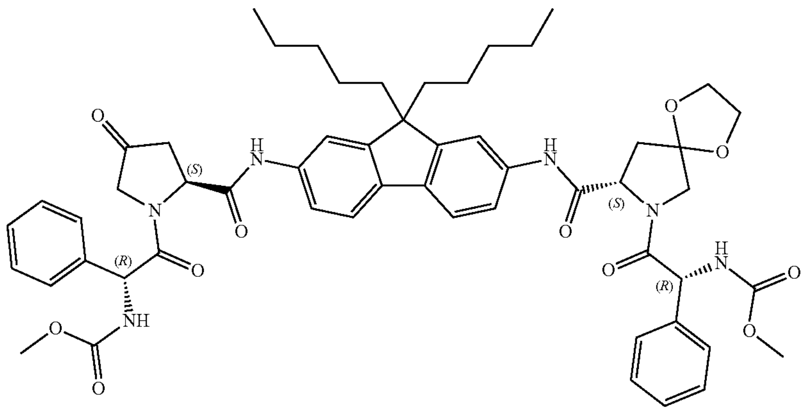 | methyl ((R)-2-((S)-8-((7-((S)-1-((R)-2-((methoxy-carbonyl)amino)-2-phenylacetyl)-4-oxopyrrolidine-2-carboxyamido)-9,9-dipentyl-9H-fluorene-2-yl)carbamoyl)-1,4-dioxa-7-azaspiro[4.4]nonane-7-yl)-2-oxo-1-phenylethyl)carbamate | LC/MS: Anal. Calcd. For [M + H]⁺: C55H65N6O11: 985.5; found 985.3 |
| 19 | 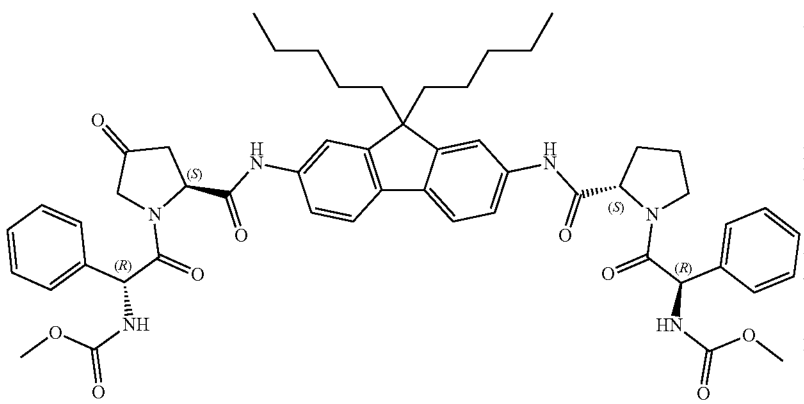 | methyl ((R)-2-((S)-2-((7-((S)-1-((R)-2-((methoxy-carbonyl)amino)-2-phenylacetyl)pyrrolidine-2-carboxyamido)-9,9-dipentyl-9H-fluorene-2-yl)carbamoyl)-4-oxopyrrolidine-1-yl)-2-oxo-1-phenylethyl)carbamate | LC/MS: Anal. Calcd. For [M + H]⁺: C53H63N6O9: 927.5; found 928.1 |
| 20 | 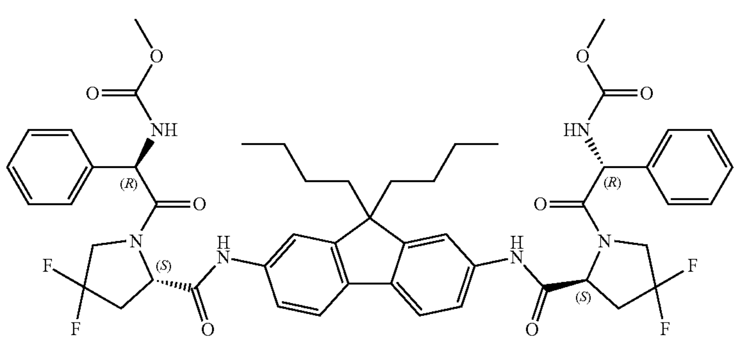 | dimethyl ((1R,1'R)-((5S,5'S)-(((9,9-dibutyl-9H-fluorene-2,7-diyl)bis(azanediyl))bis(carbonyl))bis(3,3-difluoro-pyrrolidine-5,1-diyl))bis(2-oxo-1-phenylethane-2,1-diyl))dicarbamate | LC/MS: Anal. Calcd. For [M + H]⁺: C51H57F4N6O8: 957.4; found 958.3 |

TABLE 3

| Example | Chemical Structure | Compound Name | NMR or LC/MS |
|---|---|---|---|
| 21 | 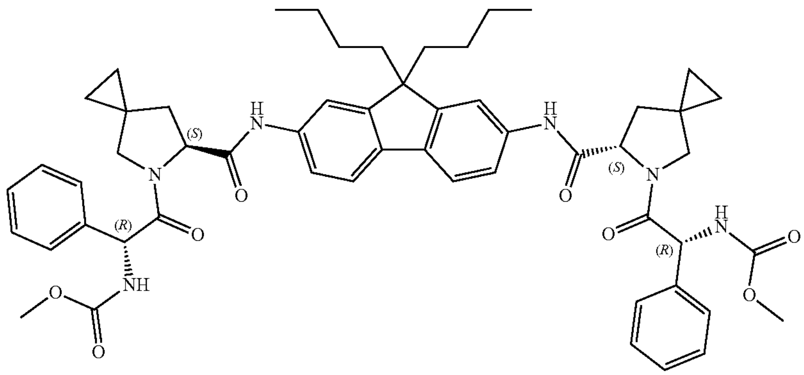 | dimethyl ((1R,1'R)-((6S,6'S)-(((9,9-dibutyl-9H-fluorene-2,7-diyl)bis(azanediyl))bis(carbonyl))bis(5-azaspiro[2.4]heptane-6,5-diyl))bis(2-oxo-1-phenylethane-2,1-diyl)) dicarbamate | LC/MS: Anal. Calcd. For [M + H]⁺: $C_{55}H_{65}N_6O_8$: 937.5; found 937.4 |
| 22 | 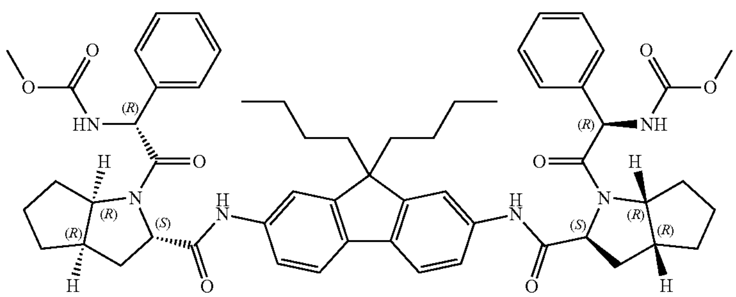 | dimethyl ((1R,1'R)-((2S,2'S,3aR,3a'R,6aR,6a'R)-(((9,9-dibutyl-9H-fluorene-2,7-diyl)bis(azanediyl))bis(carbonyl))bis(hexahydrocyclopenta[b]pyrrole-2,1(2H)-diyl))bis(2-oxo-1-phenylethane-2,1-diyl)) dicarbamate | LC/MS: Anal. Calcd. For [M + H]⁺ $C_{57}H_{69}N_6O_8$: 965.5; found 965.5 |
| 23 | 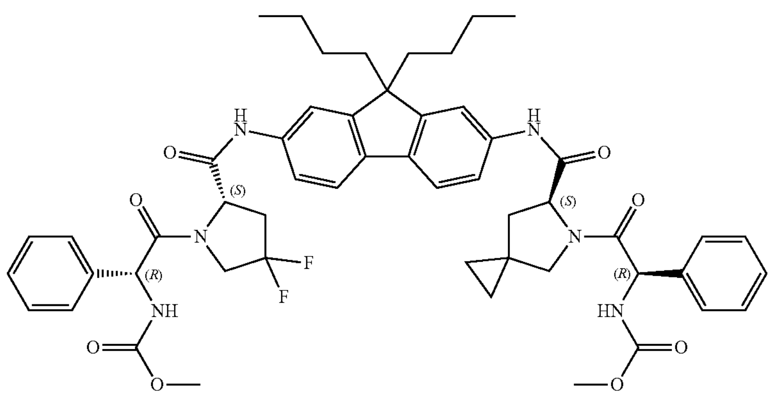 | dimethyl ((1R,1'R)-((2S,2'S,3aR,3a'R,6aR,6a'R)-(((9,9-dibutyl-9H-fluorene-2,7-diyl)bis(azanediyl))bis(carbonyl))bis(hexahydrocyclopenta[b]pyrrole-2,1(2H)-diyl))bis(2-oxo-1-phenylethane-2,1-diyl)) dicarbamate | LC/MS: Anal. Calcd. For [M + H]⁺ $C_{53}H_{61}F_2N_6O_8$: 947.5; found: 947.4 |
| 24 | 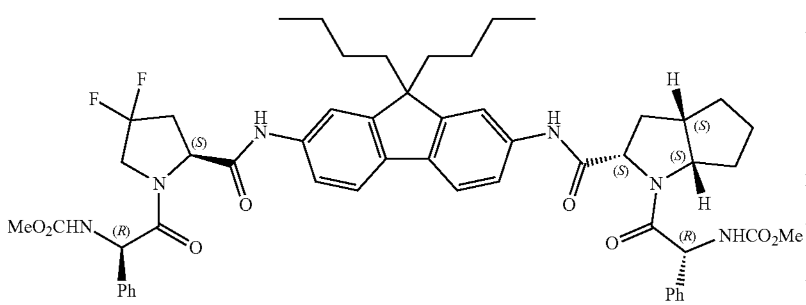 | methyl ((R)-2-((S)-2-((9,9-dibutyl-7-((S)-5-((R)-2-((methoxycarbonyl)amino)-2-phenylacetyl)-5-azaspiro[2.4]heptane-6-carboxyamido)-9H-fluorene-2-yl)carbamoyl)-4,4-difluoropyrrolidine-1-yl)-2-oxo-1-phenylethyl) carbamate | LC/MS: Anal. Calcd. For [M + H]⁺ $C_{54}H_{63}F_2N_6O_8$: 961.5; found 961.4 |

TABLE 3-continued

| Example | Chemical Structure | Compound Name | NMR or LC/MS |
|---|---|---|---|
| 25 | 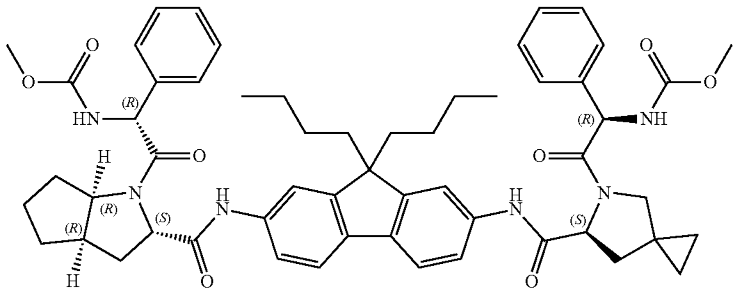 | methyl ((R)-2-((S)-6-((9,9-dibutyl-7-((2S,3aR,6aR)-1-((R)-2-((methoxycarbonyl)amino)-2-phenylacetyl)octahydrocyclopenta[b]pyrrole-2-carboxyamido)-9H-fluorene-2-yl)carbamoyl)-5-azaspiro[2.4]heptane-5-yl)-2-oxo-1-phenylethyl)carbamate | LC/MS: Anal. Calcd. For [M + H]⁺ $C_{56}H_{67}N_6O_8$: 951.5; found: 951.5 |
| 26 | 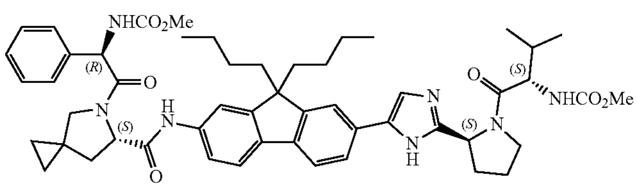 | methyl ((S)-1-((S)-2-(5-(9,9-dibutyl-7-((S)-5-((R)-2-((methoxycarbonyl)amino)-2-phenylacetyl)-5-azaspiro[2.4]heptane-6-carboxyamido)-9H-fluorene-2-yl)-1H-imidazole-2-yl)pyrrolidine-1-yl)-3-methyl-1-oxobutane-2-yl)carbamate | LC/MS: Anal. Calcd. For [M + H]⁺ $C_{52}H_{66}N_7O_7$: 900.5; found: 900.4 |
| 27 | 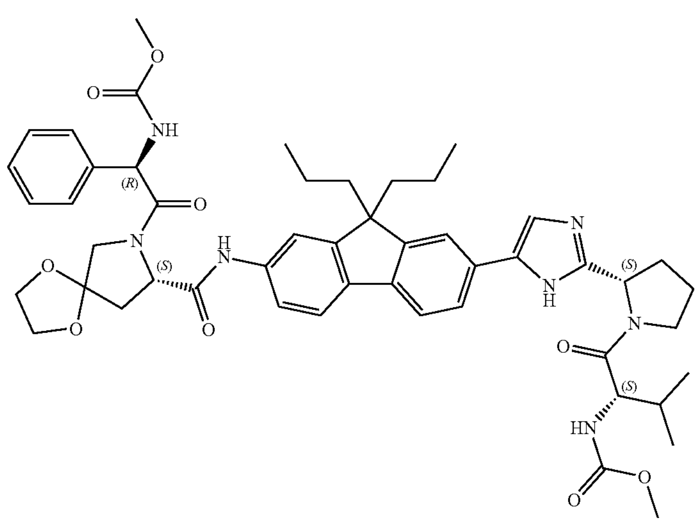 | methyl ((S)-1-((S)-2-(5-(7-((S)-7-((R)-2-((methoxycarbonyl)amino)-2-phenylacetyl)-1,4-dioxa-7-azaspiro[4.4]nonane-8-carboxyamido)-9,9-dipropyl-9H-fluorene-2-yl)-1H-imidazole-2-yl)pyrrolidine-1-yl)-3-methyl-1-oxobutane-2-yl)carbamate | LC/MS: Anal. Calcd. For [M + H]⁺: $C_{50}H_{62}N_7O_9$: 904.5; found 904.4 |

TABLE 3-continued

| Example | Chemical Structure | Compound Name | NMR or LC/MS |
|---|---|---|---|
| 28 | 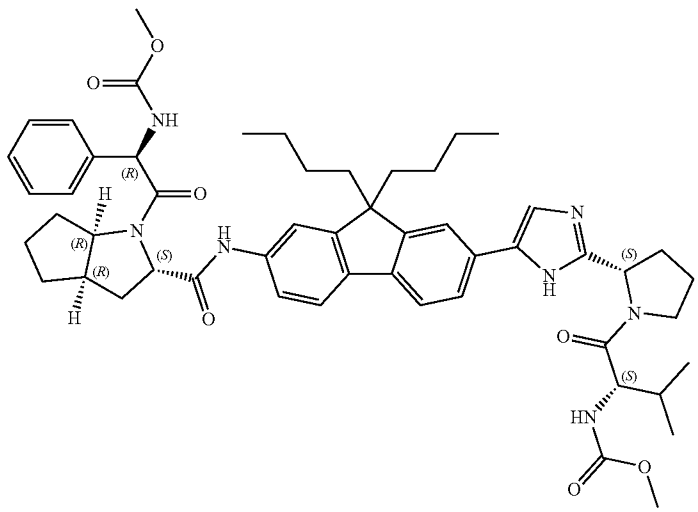 | methyl ((S)-1-((S)-2-(5-(9,9-dibutyl-7-((2S,3aR,6aR)-1-((R)-2-((methoxycarbonyl)amino)-2-phenylacetyl)octahydrocyclopenta[b]pyrrole-2-carboxyamido)-9H-fluorene-2-yl)-1H-imidazole-2-yl)pyrrolidine-1-yl)-3-methyl-1-oxobutane-2-yl)carbamate | LC/MS: Anal. Calcd. For [M + H]$^+$ $C_{41}H_{55}N_6O_6$: 914.52; found 914.5. |
| 29 | 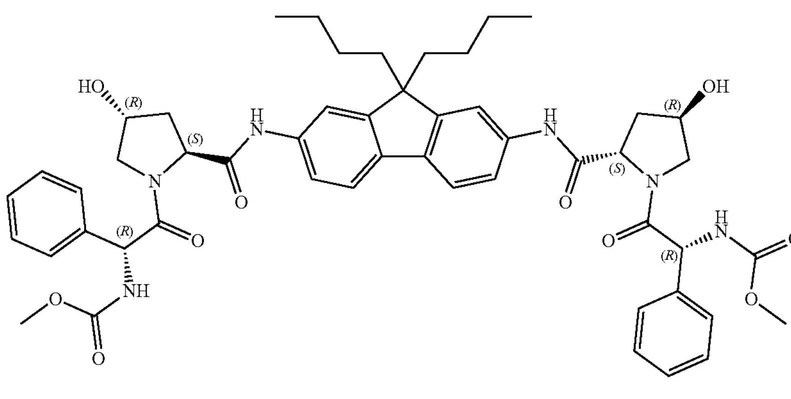 | dimethyl ((1R,1'R)-((3R,3'R,5S,5'S)-(((9,9-dibutyl-9H-fluorene-2,7-diyl)bis(azanediyl))bis(carbonyl))bis(3-hydroxypyrrolidine-5,1-diyl))bis(2-oxo-1-phenylethane-2,1-diyl))dicarbamate | LC/MS: Anal. Calcd. For [M + H]$^+$: $C_{51}H_{61}N_6O_{10}$: 917.4; found 917.3 |
| 30 | 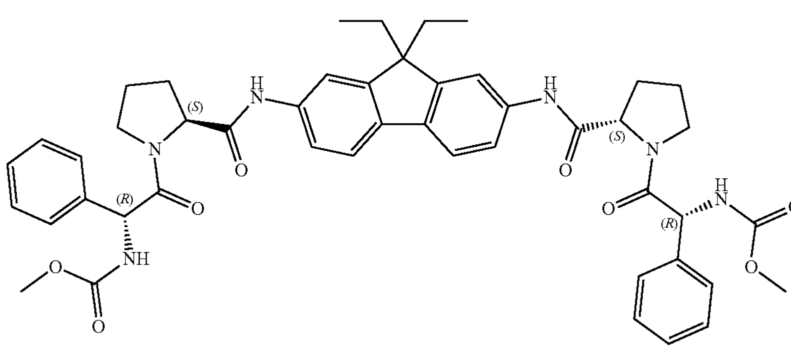 | dimethyl (1R,1'R)-2,2'-((2S,2'S)-2,2'-(9,9-diethyl-9H-fluorene-2,7-diyl)bis(azanediyl)bis(oxomethylene)bis(pyrrolidine-2,1-diyl))bis(2-oxo-1-phenylethane-2,1-diyl)dicarbamate | LC/MS: Anal. Calcd. For [M + H]$^+$: $C_{47}H_{53}N_6O_8$: 829.4; found 829.3 |

TABLE 4

| Example | Chemical Structure | Compound Name | NMR or LC/MS |
|---|---|---|---|
| 31 | 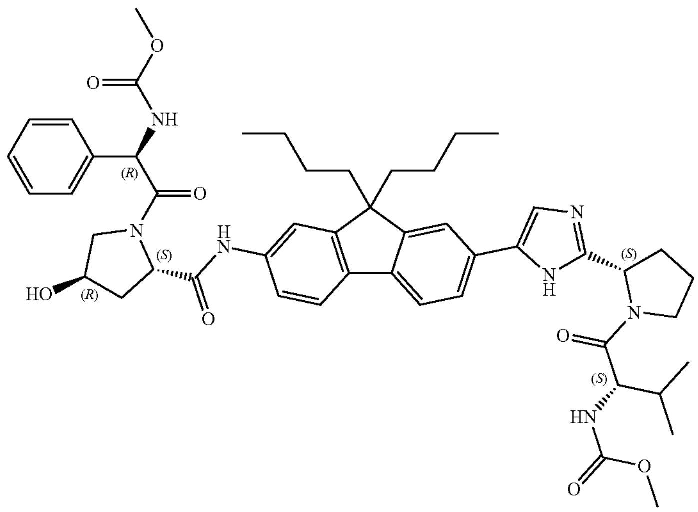 | methyl((S)-1-((S)-2-(5-(9,9-dibutyl-7-((2S,4R)-4-hydroxy-1-((R)-2-((methoxycarbonyl)amino)-2-phenylacetyl)pyrrolidine-2-carboxyamido)-9H-fluoren-2-yl)-1H-imidazole-2-yl)pyrrolidine-1-yl)-3-methyl-1-oxobutane-2-yl)carbamate | LC/MS: Anal. Calcd. For [M + H]⁺: C50H64N7O8: 890.5; found 890.3 |
| 32 | 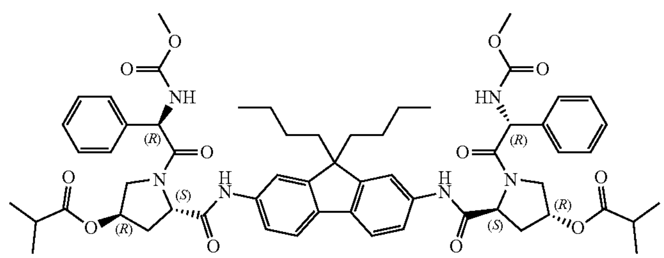 | (3R,3'R,5S,5'S,52R)-5,5'-(9,9-dibutyl-9H-fluorene-2,7-diyl)bis(azanediyl)bis(oxomethylene)bis(1-((R)-2-(methoxycarbonylamino)-2-phenylacetyl)pyrrolidine-5,3-diyl) bis(2-methylpropanoate) | LC/MS: Anal. Calcd. For [M + H]⁺: C59H73N6O12: 1057.5; found 1057.5 |
| 33 | 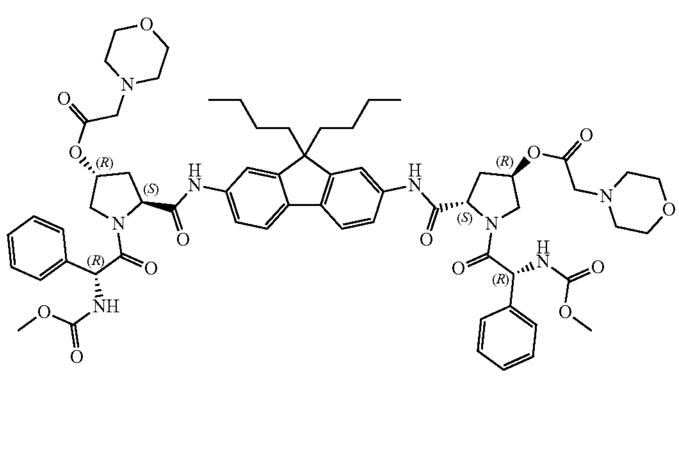 | (3R,3'R,5S,5'S,52R)-5,5'-(9,9-dibutyl-9H-fluorene-2,7-diyl)bis(azanediyl)bis(oxomethylene)bis(1-((R)-2-(methoxycarbonylamino)-2-phenylacetyl)pyrrolidine-5,3-diyl) bis(2-morpholinoacetate) | LC/MS: Anal. Calcd. For [M + H]⁺: C63H79N8O14: 1171.6; found 1171.4 |

TABLE 4-continued

| Example | Chemical Structure | Compound Name | NMR or LC/MS |
|---|---|---|---|
| 34 | 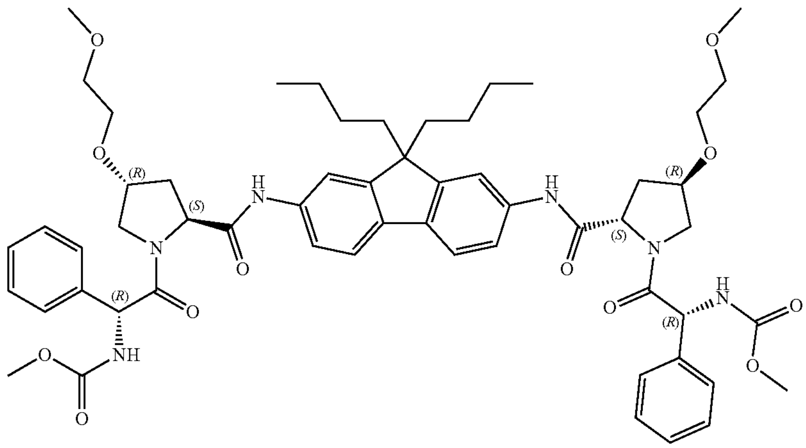 | dimethyl (1R,1'R)-2,2'-((3R,3'R,5S,5'S)-5,5'-(9,9-dibutyl-9H-fluorene-2,7-diyl)bis(azanediyl)bis(oxomethylene)bis(3-(2-methoxyethoxy)pyrrolidine-5,1-diyl))bis(2-oxo-1-phenylethane-2,1-diyl)dicarbamate | LC/MS: Anal. Calcd. For [M + H]+: C57H73N6O12: 1033.5; found 1033.4 |
| 35 | 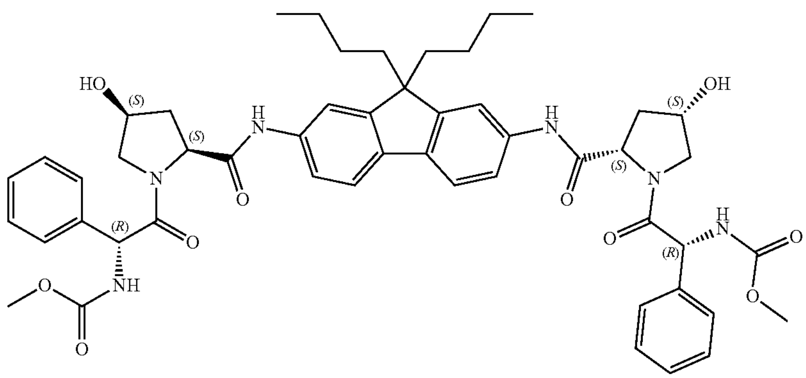 | dimethyl (1R,1'R)-2,2'-((3S,3'S,5S,5'S)-5,5'-(9,9-dibutyl-9H-fluorene-2,7-diyl)bis(azanediyl)bis(oxomethylene)bis(3-hydroxypyrrolidine-5,1-diyl))bis(2-oxo-1-phenylethane-2,1-diyl)dicarbamate | LC/MS: Anal. Calcd. For [M + H]+: C51H61N6O10: 917.4; found 917.3 |
| 36 | 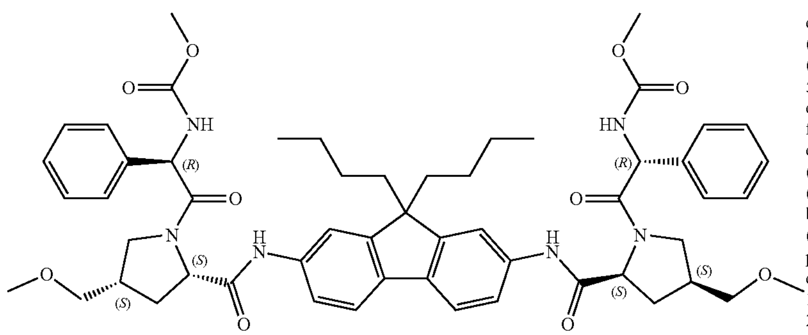 | dimethyl (1R,1'R)-2,2'-((3S,3'S,5S,5'S)-5,5'-(9,9-dibutyl-9H-fluorene-2,7-diyl)bis(azanediyl)bis(oxomethylene)bis(3-(methoxymethyl)pyrrolidine-5,1-diyl))bis(2-oxo-1-phenylethane-2,1-diyl)dicarbamate | LC/MS: Anal. Calcd. For [M + H]+ C55H69N6O10: 973.5; found: 973.3 |
| 37 | 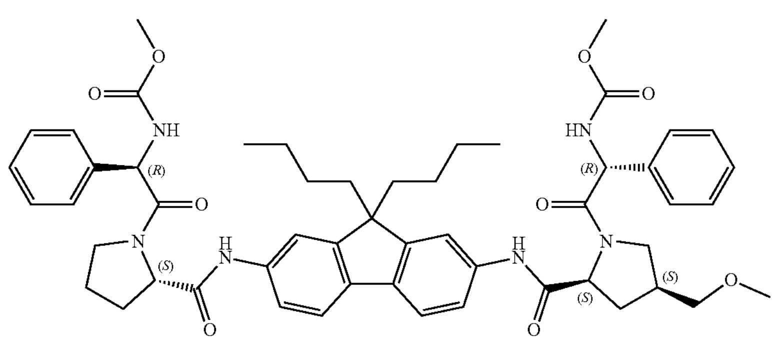 | methyl ((R)-2-((2S,4S)-2-((9,9-dibutyl-7-((S)-1-((R)-2-((methoxycarbonyl)amino)-2-phenylacetyl)pyrrolidine-2-carboxyamido)-9H-fluoren-2-yl)carbamoyl)-4-(methoxymethyl)pyrrolidine-1-yl)-2-oxo-1-phenylethyl)carbamate | LC/MS: Anal. Calcd. For [M + H]+ C53H65N6O9: 929.5; found: 929.3 |

TABLE 4-continued

| Example | Chemical Structure | Compound Name | NMR or LC/MS |
|---|---|---|---|
| 38 | 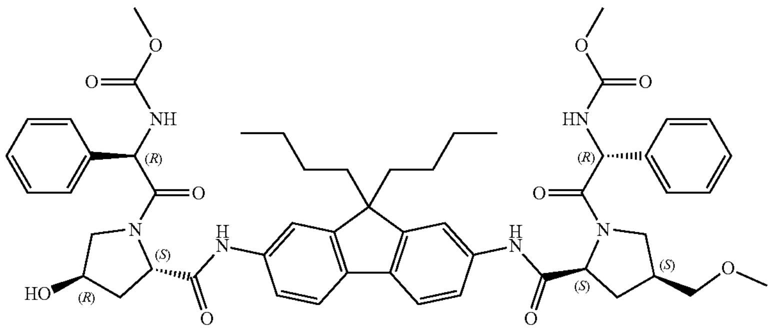 | methyl ((R)-2-((2S,4S)-2-((9,9-dibutyl-7-((2S,4R)-4-hydroxy-1-((R)-2-((methoxycarbonyl)amino)-2-phenylacetyl)pyrrolidine-2-carboxyamido)-9H-fluoren-2-yl)carbamoyl)-4-(methoxymethyl)pyrrolidine-1-yl)-2-oxo-1-phenylethyl)carbamate | LC/MS: Anal. Calcd. For [M + H]$^+$ C53H65N6O10: 945.5; found: 945.3 |
| 39 | 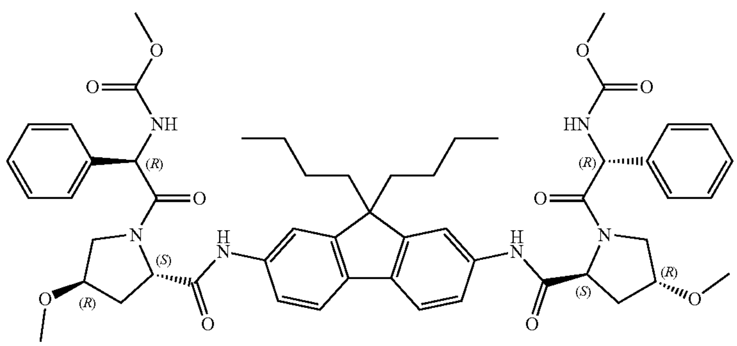 | dimethyl (1R,1'R)-2,2'-((3R,3'R,5S,5'S)-5,5'-(9,9-dibutyl-9H-fluorene-2,7-diyl)bis(azanediyl)bis(oxomethylene)bis(3-methoxypyrrolidine-5,1-diyl))bis(2-oxo-1-phenylethane-2,1-diyl)dicarbamate | LC/MS: Anal. Calcd. For [M + H]$^+$ C$_{53}$H$_{65}$N$_6$O$_{10}$$^+$: 945.5; found 945.4 |
| 40 | 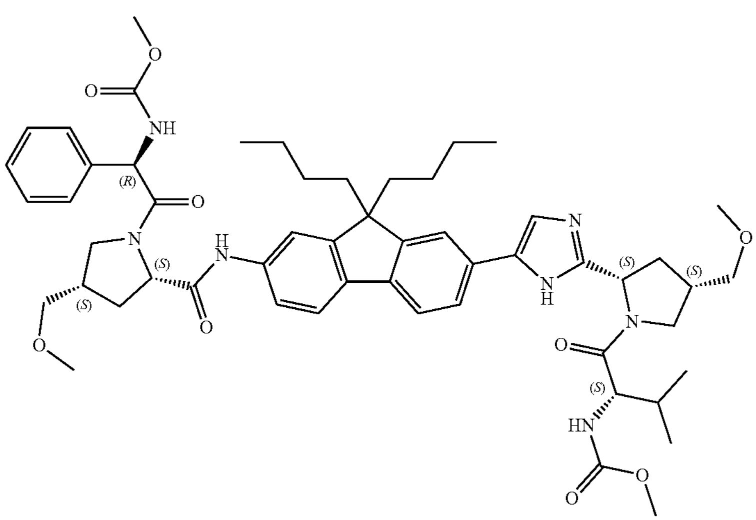 | methyl ((S)-1-((2S,4S)-2-(5-(9,9-dibutyl-7-((2S,4S)-1-((R)-2-((methoxycarbonyl)amino)-2-phenylacetyl)-4-(methoxymethyl)pyrrolidine-2-carboxyamido)-9H-fluoren-2-yl)-1H-imidazol-2-yl)-4-(methoxymethyl)pyrrolidine-1-yl)-3-methyl-1-oxobutane-2-yl)carbamate | LC/MS: Anal. Calcd. For [M + H]$^+$ C$_{54}$H$_{72}$N$_7$O$_9$$^+$: 962.5; found 962.4 |

TABLE 4-continued

| Example | Chemical Structure | Compound Name | NMR or LC/MS |
|---|---|---|---|
| 41 | 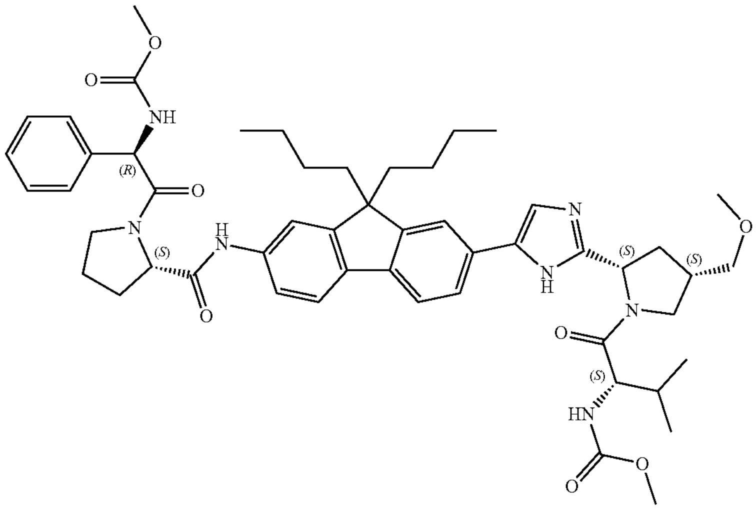 | methyl ((S)-1-((2S,4S)-2-(5-(9,9-dibutyl-7-((S)-1-((R)-2-((methoxycarbonyl)amino)-2-phenylacetyl)pyrrolidine-2-carboxyamido)-9H-fluorene-2-yl)-1H-imidazole-2-yl)-4-(methoxymethyl)pyrrolidine-1-yl)-3-methyl-1-oxobutane-2-yl)carbamate | LC/MS: Anal. Calcd. For [M + H]$^+$ C$_{52}$H$_{68}$N$_7$O$_8$$^+$: 918.5; found 918.4 |
| 42 | 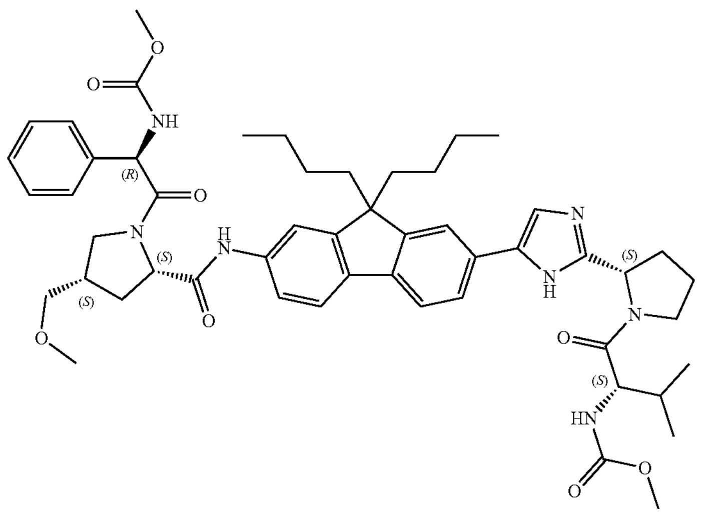 | methyl ((S)-1-((S)-2-(5-(9,9-dibutyl-7-((2S,4S)-1-((R)-2-((methoxycarbonyl)amino)-2-phenylacetyl)-4-(methoxymethyl)pyrrolidine-2-carboxyamido)-9H-fluorene-2-yl)-1H-imidazole-2-yl)pyrrolidine-1-yl)-3-methyl-1-oxobutane-2-yl)carbamate | LC/MS: Anal. Calcd. For [M + H]$^+$ C$_{52}$H$_{68}$N$_7$O$_8$$^+$: 918.5; found 918.4 |

<Experimental Example 1> Measurement of Anti-HCV Activity of Compounds of Examples Using HCVcc Step 1: Cell Line and Cell Culture Huh 7.5.1 cells were grown in Dulbecco's Modified Eagle's medium (DMEM; Gibco) supplemented with antibiotics (100 U/mL penicillin, 10 μg/mL streptomycin) and 10% heat-inactivated fetal bovine serum (ΔFBS; PEAK) in a CO$_2$ incubator at 37° C. with 6.0% humidity.

Step 2: Virus Production

Huh7.5.1 cells were transfected with in vitro transcription RNA of JFH5a-Rluc-ad34, a derivative of JFH1 with adaptive mutations in E2 and p7 regions, by electroporation. JFH5a-Rluc-ad34 virus contains Renilla luciferase (Rluc), which is convenient for virus proliferation assay. The cell culture medium containing HCV was collected 3-5 days after the electroporation and then filtered through a 0.45 μM pore size filter.

Step 3: Antiviral Activity Test Using Infectious HCV Particles

Huh 7.5.1 cells were inoculated with JFH5a-Rluc-ad34 virus and incubated for 4 hours. Four hours after the virus inoculation, the Huh7.5.1 cells infected with HCV were cultured in the medium containing the compound of examples serially diluted. Three days later, the cells were harvested and the intracellular luciferase activity was measured using Renilla luciferase assay system (Promega). Finally, the luciferase activity was normalized with those obtained from the negative control cells (mock-treated cells).

<Experimental Example 2> Measurement of Anti-HCV Activity of Compounds of Examples Using HCV Replicon Step 1: Cell Line and Cell Culture Anti-HCV activity of the compounds of examples was tested using Huh 7.5.1 cells containing bicistronic HCV replicon NK5.1-Gluc (genotype 1b) and S52-Feo (genotype 3a). The first open reading frame (ORF) included a Reporter gene (*Gaussia* luciferase; 1b, Firefly luciferase; 3a) fused with foot-and-mouth disease virus (FMDV) 2a gene and neomycin phosphotransferase gene and the second ORF HCV nonstructural gene NS3-5. The replicon-containing cells were cultured under the same conditions as described above with additional antibiotic G418 (0.5 mg/ml, Calbiochem).

Step 2: Antiviral Activity Test Using HCV Replicon

Huh 7.5.1 cells containing the HCV replicon NK5.1-Gluc (GT1b) or S52-Feo (GT-3a) were incubated in a 12-well plate ($5 \times 10^4$ cells per well). After 16 hours, the replicon containing cells were inoculated with the medium containing the compounds of examples diluted serially for 3 days. After the compound treatment, in the case of NK5.1-Gluc, the cell culture medium was collected and the Gaussia luciferase activity was measured using Renilla luciferase assay system (Promega). In the case of S52-Feo, the cells were harvested and the luciferase activity was measured using firefly luciferase assay system (Promega). The luciferase activity was normalized with those obtained from the negative control cells (mock-treated cells).

<Experimental Example 3> Transiently Transfected Assay of Genotype 1b Resistance Mutant RNAs Replicon genomes substituted with Y93H, L31V and L31V+Y93H (double mutant), the resistance mutants to Daclatasvir with mutations at the NS5A protein domain 1.

These HCV resistance mutant genomes were linearized with scal restriction enzyme, and then the mutated HCV RNA was synthesized through in vitro transcription. Huh 7.5.1 cells were individually electroporated with HCV RNA with resistant mutations and plated in a 12 well plate. After 4 hours, Huh7.5.1 cells were seeded in DMEM containing the compounds of examples serially diluted for 3 days. Three days later, the cells were harvested and the intracellular luciferase activity was measured. The luciferase activity was normalized with those obtained from the negative control cells (mock-treated cells).

TABLE 5

| Example | HCV wt. GT-1b | HCV wt. GT-2a | HCV wt. GT-3a | HCV Mutation L31V | HCV Mutation Y93H | HCV Mutation L31V + Y93H |
|---|---|---|---|---|---|---|
| 1 | B | D | C | C | D | E |
| 2 | A | D | B | A | C | D |
| 3 | B | B | B | B | B | D |
| 4 | A | D | B | C | E | D |
| 5 | A | D | B | C | E | E |
| 6 | B | C | B | A | C | D |
| 7 | B | D | B | A | B | C |
| 8 | A | A | B | B | B | D |
| 9 | A | B | B | B | B | C |
| 10 | A | C | B | A | C | D |
| 11 | A | D | B | A | D | D |
| 12 | A | D | B | A | C | D |
| 13 | A | D | C | A | A | B |
| 14 | A | B | B | A | A | D |
| 15 | A | D | C | A | B | B |
| 16 | A | D | B | A | B | D |
| 17 | A | D | B | A | C | D |
| 18 | B | D | C | B | C | D |
| 19 | B | D | D | B | C | D |

TABLE 5-continued

| Example | HCV wt. GT-1b | HCV wt. GT-2a | HCV wt. GT-3a | HCV Mutation L31V | HCV Mutation Y93H | HCV Mutation L31V + Y93H |
|---|---|---|---|---|---|---|
| 20 | A | D | B | B | D | — |
| 21 | A | C | B | B | D | D |
| 22 | A | D | B | A | B | E |
| 23 | — | — | — | A | D | E |
| 24 | — | — | — | A | D | D |
| 25 | A | D | B | A | D | D |
| 26 | A | B | B | B | C | E |
| 27 | A | B | B | A | A | D |
| 28 | A | B | B | B | C | E |
| 29 | A | C | B | B | B | B |
| 30 | B | C | C | C | D | E |
| 31 | B | C | C | C | B | D |
| 32 | A | C | B | B | B | B |
| 33 | B | C | C | B | B | C |
| 34 | C | D | D | B | B | D |
| 35 | B | D | B | A | C | D |
| 36 | A | C | B | A | A | C |
| 37 | A | C | A | A | B | D |
| 38 | B | C | B | A | A | B |
| 39 | B | D | C | A | B | D |
| 40 | A | B | C | A | B | D |
| 41 | B | B | C | A | B | D |
| 42 | B | C | C | A | B | D |

In Table 5,
A: 1 pM < $EC_{50}$ < 10 pM;
B: 10 pM < $EC_{50}$ < 100 pM;
C: 100 pM < $EC_{50}$ < 1 nM;
D: 1 nM < $EC_{50}$ < 100 nM; and
E: $EC_{50}$ > 100 nM.

As shown in table 5, it was confirmed that the compounds of examples according to the present invention inhibited not only HCV of genotypes 1b, 2a and 3a, but also L31V, Y93H and L31V+Y93H (double mutant), the resistance mutants frequently observed in genotype 1b, at low concentrations.

While the conventional HCV drugs inhibited genotype 1b selectively at low concentrations, but did not inhibit types 2a and 3a, whereas the compounds of examples according to the present invention exhibited excellent antiviral performance against genotypes 1b, 2a and 3a at low concentrations.

The pharmaceutical composition of the present invention was confirmed to inhibit L31V and Y93H (single mutants) as well as L31V+Y93H (double mutant) showing stronger resistance at low concentrations. Therefore, the pharmaceutical composition of the present invention can be effectively used as a therapeutic agent targeting not only single mutants but also double or multiple mutants, and for the prevention or treatment of HCV-related liver disease by which the problem of resistant mutation against conventional therapeutic agents is solved.

<Manufacturing Example 1> Preparation of Powders

| Derivative represented by formula 1 | 2 g |
|---|---|
| Lactose | 1 g |

Powders were prepared by mixing all the above components, which were filled in airtight packs according to the conventional method for preparing powders.

<Manufacturing Example 2> Preparation of Tablets

| | |
|---|---|
| Derivative represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

<Manufacturing Example 3> Preparation of Capsules

| | |
|---|---|
| Derivative represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<Manufacturing Example 4> Preparation of Injectable Solutions

| | |
|---|---|
| Derivative represented by formula 1 | 100 mg |
| Mannitol | 180 mg |
| $Na_2HPO_4 \cdot 2H_2O$ | 26 mg |
| Distilled water | 2974 mg |

Injectable solutions were prepared by containing all the above components in the amounts indicated according to the conventional method for preparing injectable solutions.

<Manufacturing Example 5> Preparation of Health Food

| | |
|---|---|
| Derivative represented by formula 1 | 500 ng |
| Vitamin complex | proper amount |
| Vitamin A acetate | 70 mg |
| Vitamin E | 1.0 mg |
| Vitamin | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinamide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate | 15 mg |
| Calcium phosphate, dibasic | 55 mg |
| Potassium citrate | 90 mg |
| Calcium carbonate | 100 mg |
| Magnesium chloride | 24.8 mg |

The vitamins and minerals appropriate for health food were mixed according to the preferred mixing ratio but the composition ratio can be adjusted arbitrarily. After mixing the above components according to the conventional method for preparing health food, granules were prepared and the granules were used for the preparation of a health food composition according to the conventional method.

<Manufacturing Example 6> Preparation of Health Beverage

| | |
|---|---|
| Derivative represented by formula 1 | 500 ng |
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverage. The mixture was heated at 85° C. for 1 hour with stirring. The resulting solution was filtered and loaded in sterilized containers, which were sealed and sterilized again, stored in a refrigerator until they would be used for the preparation of a composition for health beverage.

The constituents appropriate for favorite beverage were mixed according to the preferred mixing ratio but the composition ratio can be adjusted according to regional and ethnic preferences such as demand class, demand country, and purpose of use, etc.

INDUSTRIAL APPLICABILITY

A fluorene derivative according to the present invention can be used in a pharmaceutical composition for prevention or treatment of HCV-caused liver disease, such as acute hepatitis C, chronic hepatitis C, liver cirrhosis, hepatocellular cancer, etc., particularly, liver disease caused by mutants of HCV. The derivative can be useful in a pharmaceutical composition for prevention or treatment of HCV-related liver disease by which the problem of resistant mutation against conventional therapeutic agents is solved.

What is claimed is:

1. A compound represented by Formula 1 below, an optical isomer thereof or a pharmaceutically acceptable salt thereof:

[Formula 1]

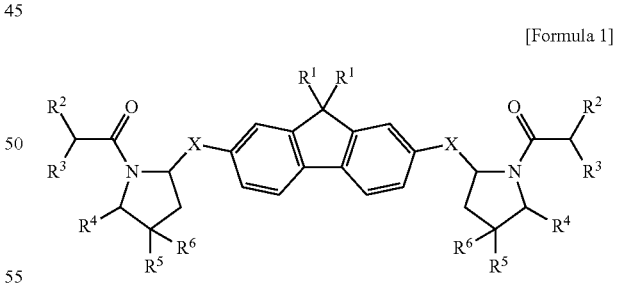

in Formula 1,
each of two Xs is independently —NHC(=O)—, —C(=O)NH— or imidazolylene, in which at least one of X is necessarily —NHC(=O)— or —C(=O)NH—;
$R^1$ is —$(CH_2)_3CH_3$, —$(CH_2)_4CH_3$, —$(CH_2)_3CF_3$, or —$(CH_2)_4CF_3$, or $(CH_2)_4CF_3$;
$R^2$ is straight or branched $C_{1-10}$ alkoxycarbonylamino;
$R^3$ is straight or branched $C_{1-10}$ alkyl or $C_{6-10}$ aryl;
$R^4$ is hydrogen, or, can form $C_{3-7}$ cycloalkyl along with one of $R^5$ and $R^6$, and C atoms to which they are attached; and R[5] and R[6] are independently hydrogen, —OH, halogen, straight or branched $C_{1-10}$ alkoxy, straight or branched $C_{1-10}$ alkoxy-$C_{1-4}$ alkyl, $O(CH_2)_2OCH_3$ or —O(C=O)R[a], wherein R[a] is straight or branched $C_{1-10}$ alkyl or 5 or 6 membered heterocycloalkyl containing one or more heteroatoms selected from the group consisting of N, O and S—straight or branched $C_{1-4}$ alkyl, or, can form carbonyl, $C_{3-7}$ cycloalkyl or 3-7 membered heterocycloalkyl containing one or more O atoms along with C atoms to which they are attached.

2. The compound, the optical isomer thereof or the pharmaceutically acceptable salt thereof according to claim 1, wherein:

R[2] is straight or branched $C_{1-6}$ alkoxycarbonylamino;

R[3] is straight or branched $C_{1-6}$ alkyl or phenyl;

R[4] is hydrogen, or, can form $C_{3-5}$ cycloalkyl along with one of R[5] and R[6], and C atoms to which they are attached; and R[5] and R[6] are independently hydrogen, —OH, halogen, straight or branched $C_{1-6}$ alkoxy, straight or branched $C_{1-6}$ alkoxy-$C_{1-2}$ alkyl or —O(C=O)R[a], wherein R[a] is straight or branched $C_{1-6}$ alkyl or 6 membered heterocycloalkyl containing one or more heteroatoms selected from the group consisting of N, O and S—$C_{1-2}$ alkyl, or R[5] and R[6] together can form carbonyl, $C_{3-5}$ cycloalkyl or 3-5 membered heterocycloalkyl containing one or more O atoms along with C atoms to which they are attached.

3. The compound, the optical isomer thereof or the pharmaceutically acceptable salt thereof according to claim 1, wherein:

R[2] is straight or branched $C_{1-4}$ alkoxycarbonylamino;

R[3] is straight or branched $C_{1-4}$ alkyl or phenyl;

R[4] is hydrogen or can form cyclopropyl or cyclopentyl along with one of R[5] and R[6], and C atoms to which they are attached; and R[5] and R[6] are independently hydrogen, —OH, halogen, straight or branched $C_{1-4}$ alkoxy, straight or branched $C_{1-4}$ alkoxy-$C_{1-2}$ alkyl or —O(C=O)R[a], wherein R[a] is straight or branched $C_{1-4}$ alkyl or morpholinyl-$C_{1-2}$ alkyl, or R[5] and R[6] together can form carbonyl, $C_{3-5}$ cycloalkyl or 5 membered heterocycloalkyl containing one or more O atoms along with C atoms to which they are attached.

4. The compound, the optical isomer thereof or the pharmaceutically acceptable salt thereof according to claim 1, wherein:

each of two Xs is independently

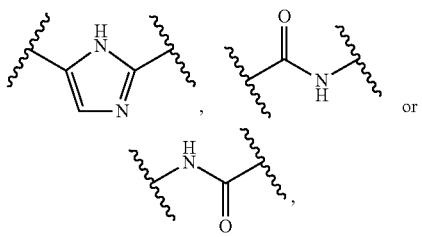

in which at least one of X is necessarily

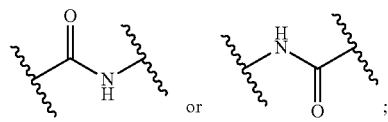 [SMILES: *NC(*)=O ; *NC(*)=O]

R[2] is

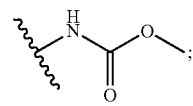

R[3] is isopropyl or phenyl;

R[4] is hydrogen or can form cyclopentyl along with one of R[5] and R[6], and C atoms to which they are attached; and R[5] and R[6] are independently hydrogen, —OH, —F, —$OCH_3$, —$CH_2OCH_3$, —$O(CH_2)_2OCH_3$,

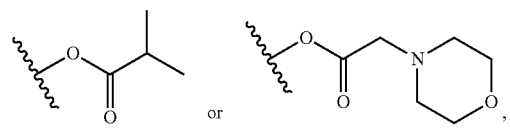

or R[5] and R[6] together can form carbonyl, cyclopropyl or 1,3-dioxolanyl along with C atoms to which they are attached.

5. The compound, the optical isomer thereof or the pharmaceutically acceptable salt thereof according to claim 1, wherein the compound represented by formula 1 is any one selected from the group consisting of the following compounds

[Formula 1-2]

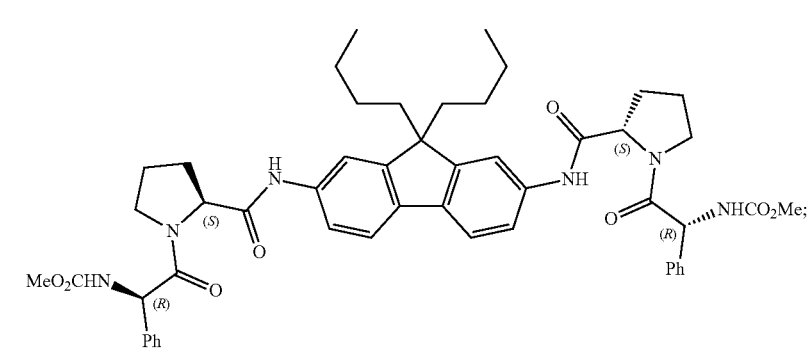

-continued
[Formula 1-4]
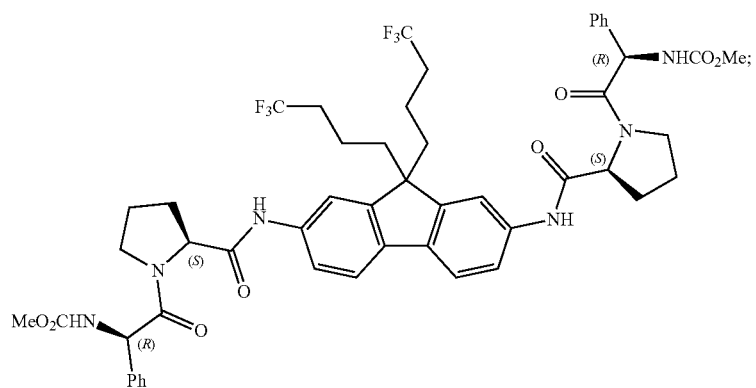
[Formula 1-5]
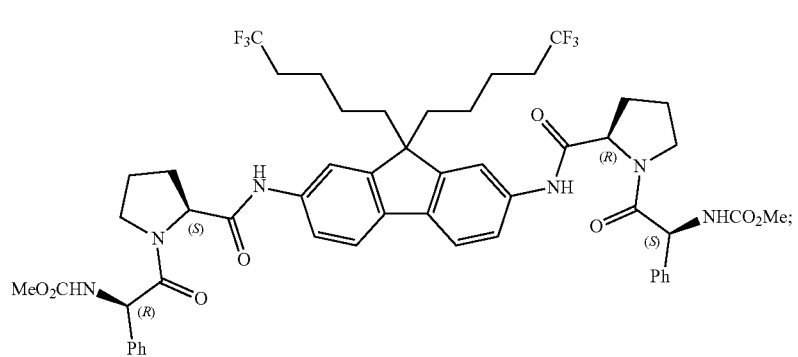
[Formula 1-6]
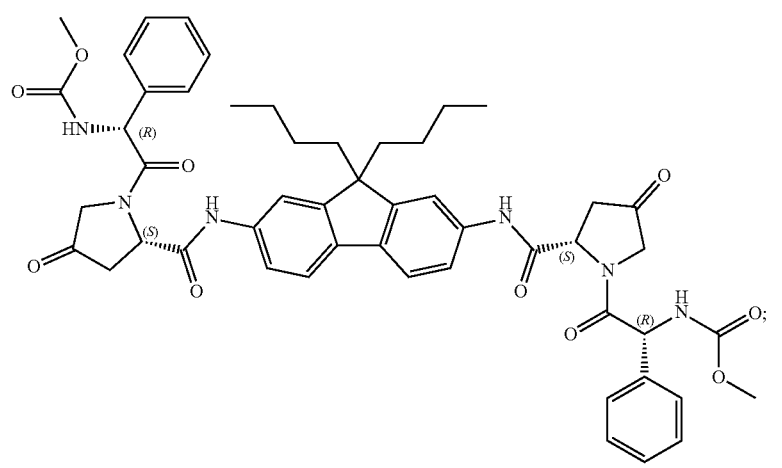
[Formula 1-7]
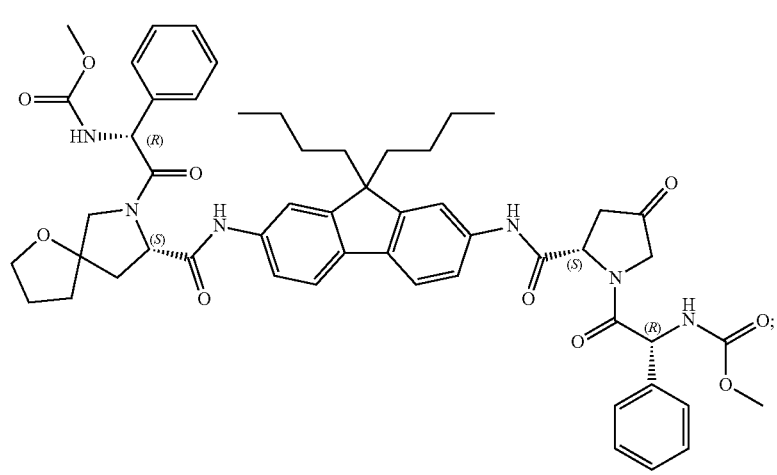

[Formula 1-9]
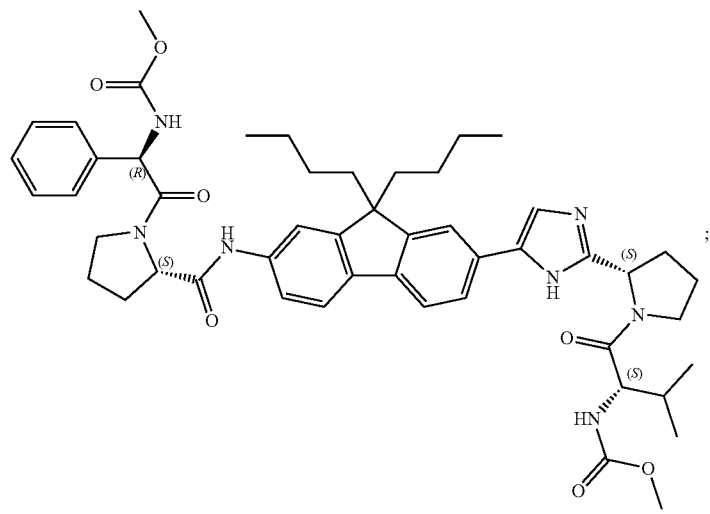
[Formula 1-10]
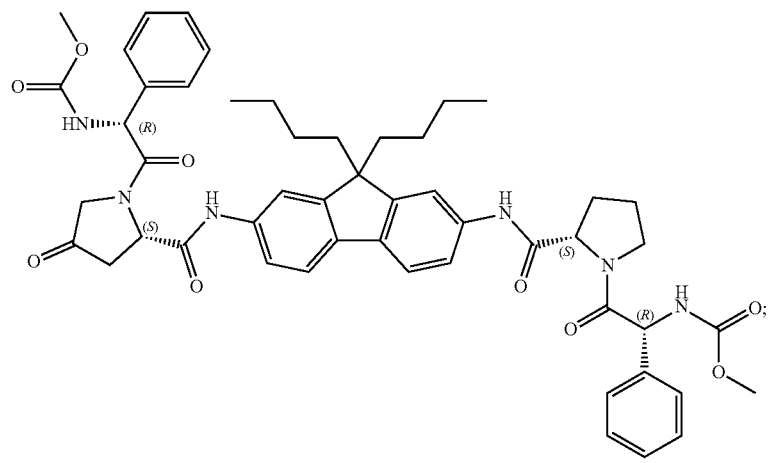
[Formula 1-11]
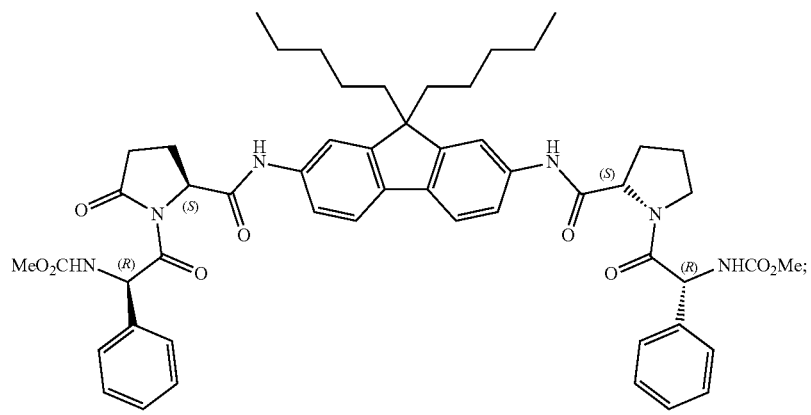

[Formula 1-12]
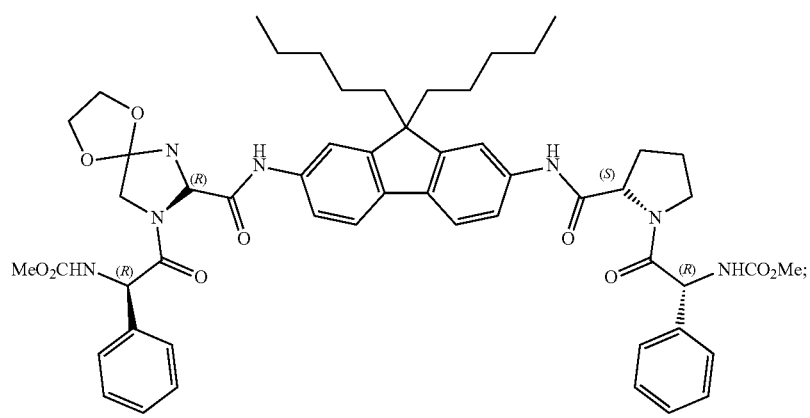
[Formula 1-13]
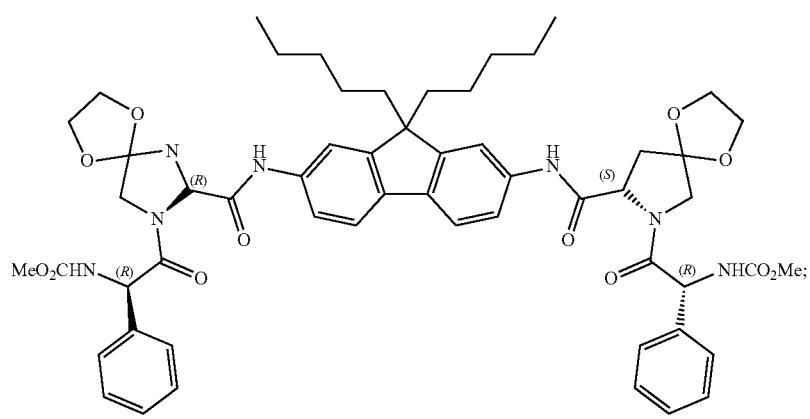
[Formula 1-14]
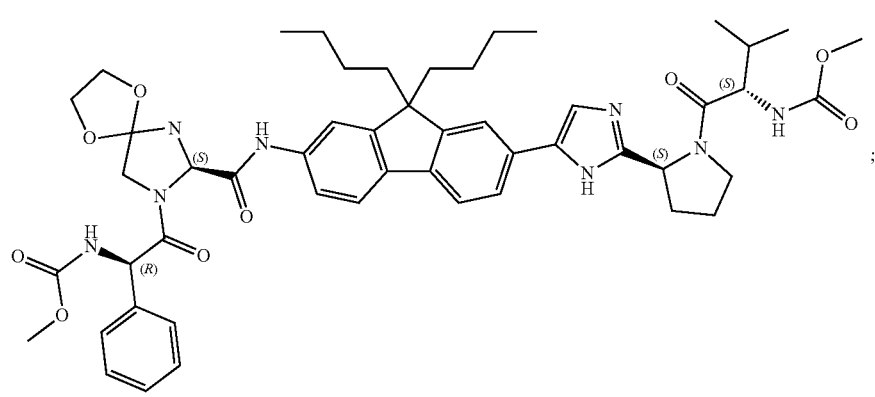
[Formula 1-15]
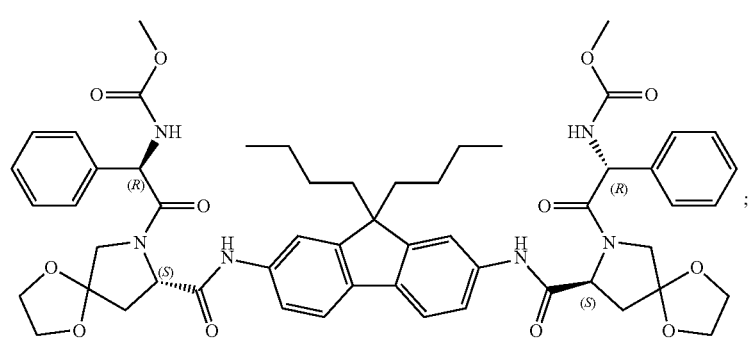

[Formula 1-16]
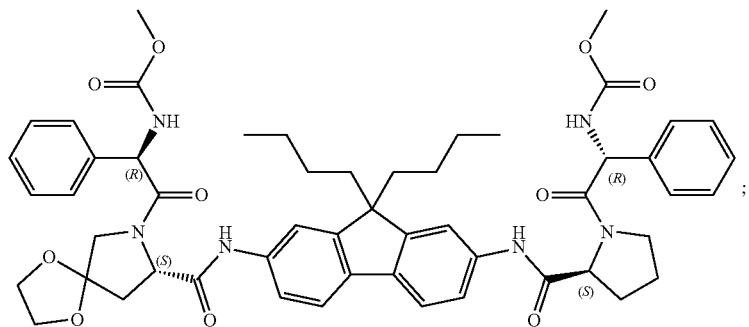
[Formula 1-17]
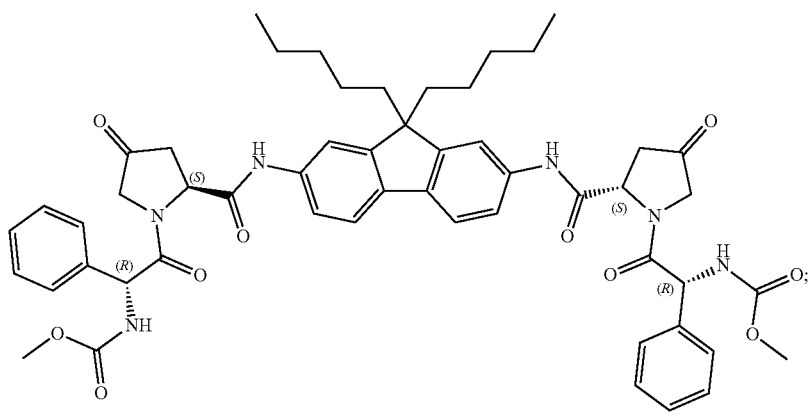
[Formula 1-18]
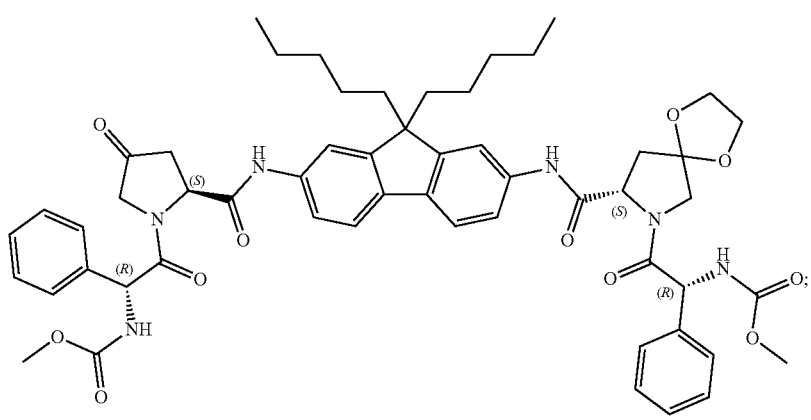
[Formula 1-19]
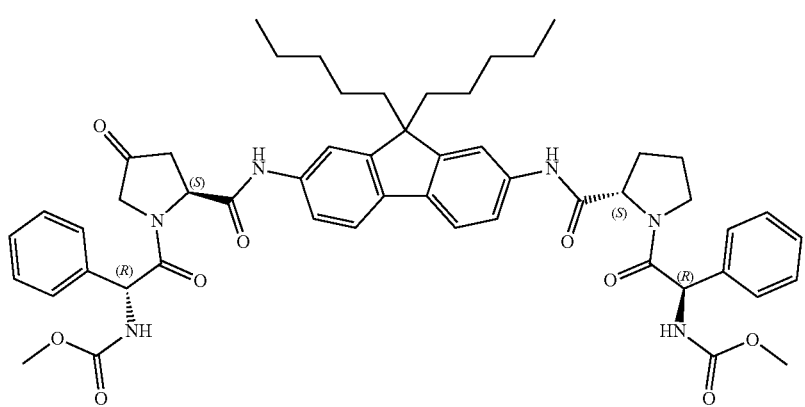

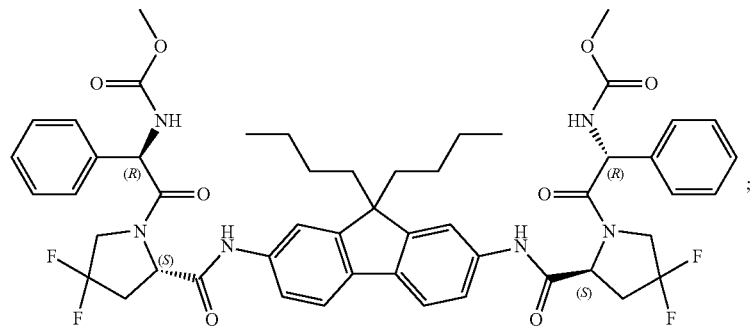
[Formula 1-20]
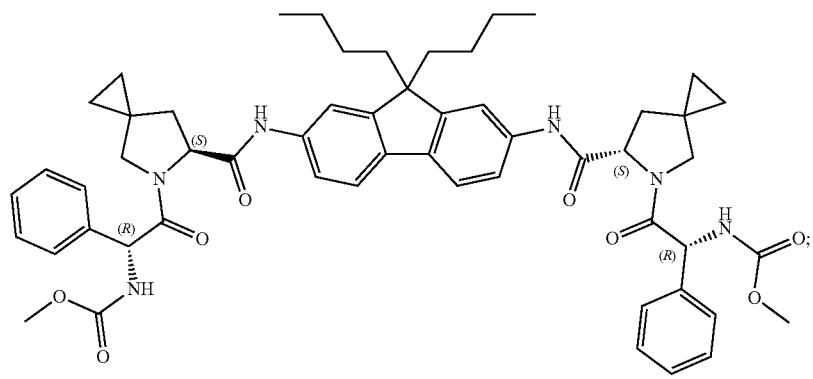
[Formula 1-21]
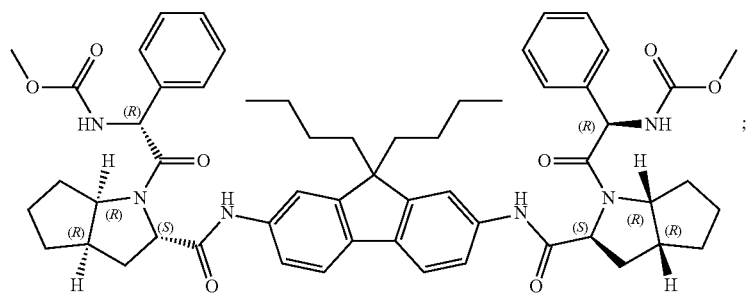
[Formula 1-22]
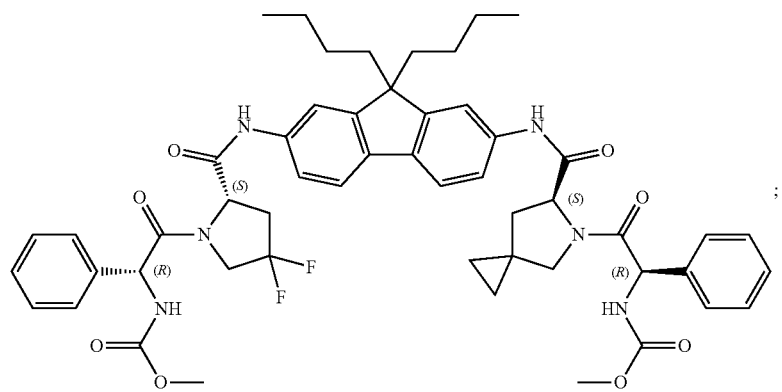
[Formula 1-23]

[Formula 1-24]
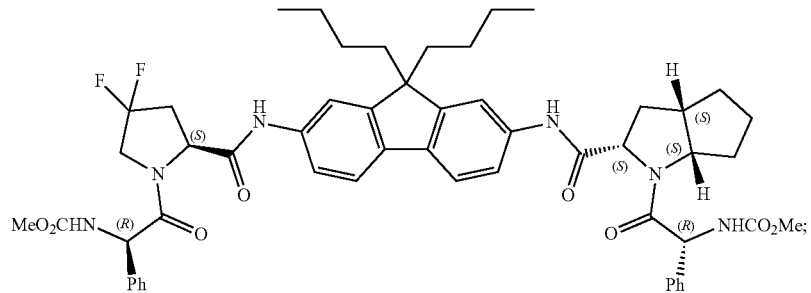
[Formula 1-25]
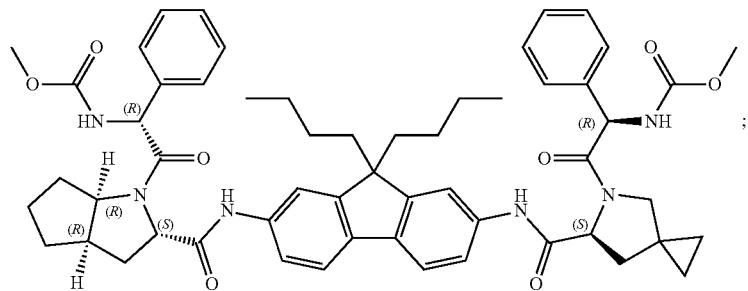
[Formula 1-26]
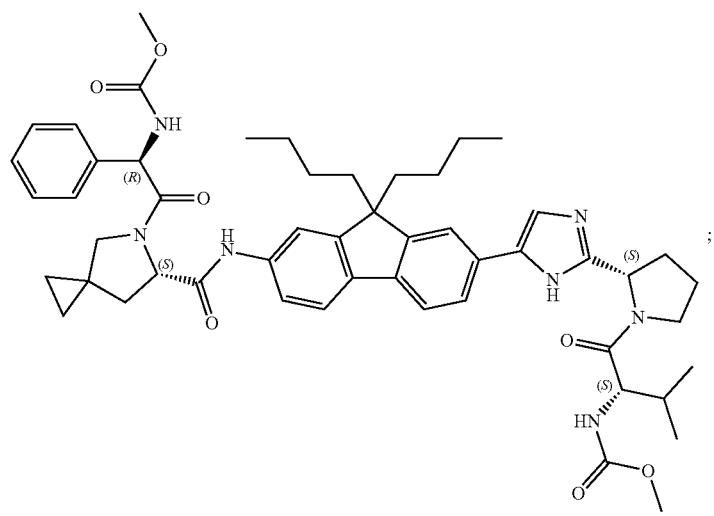
[Formula 1-28]
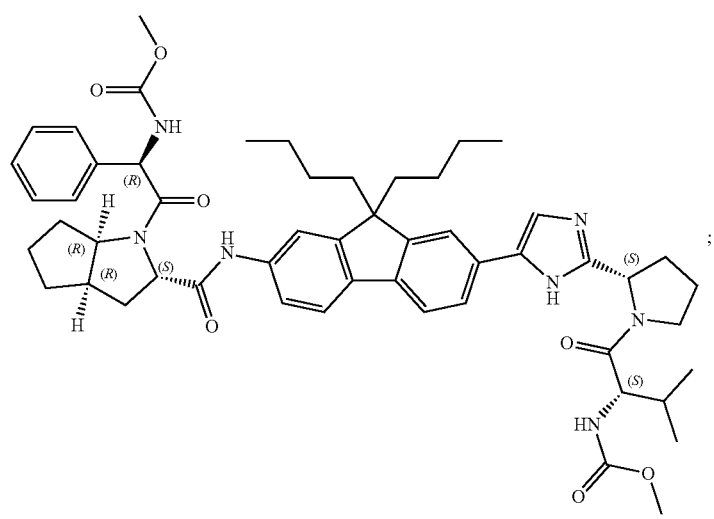

[Formula 1-29]
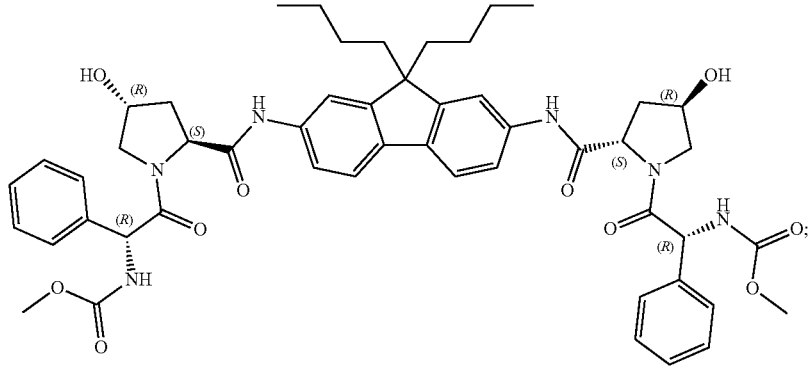
[Formula 1-31]
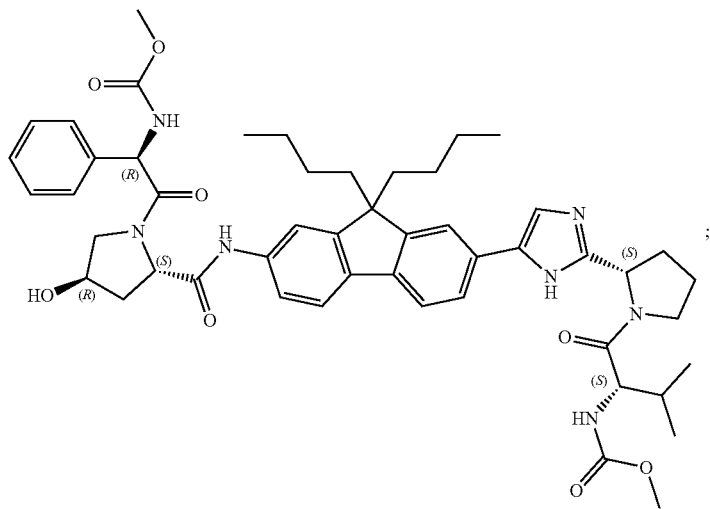
[Formula 1-32]
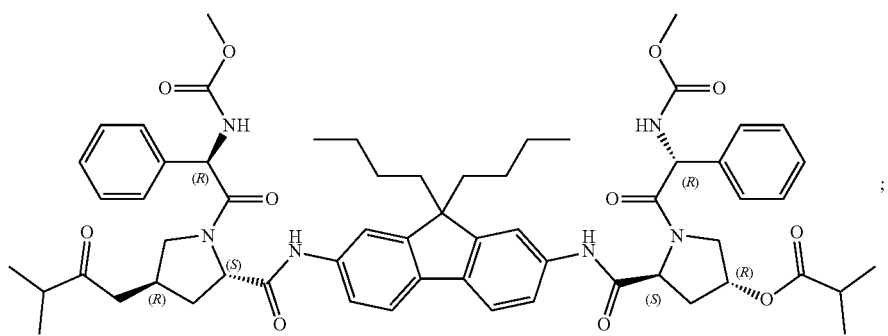

[Formula 1-33]
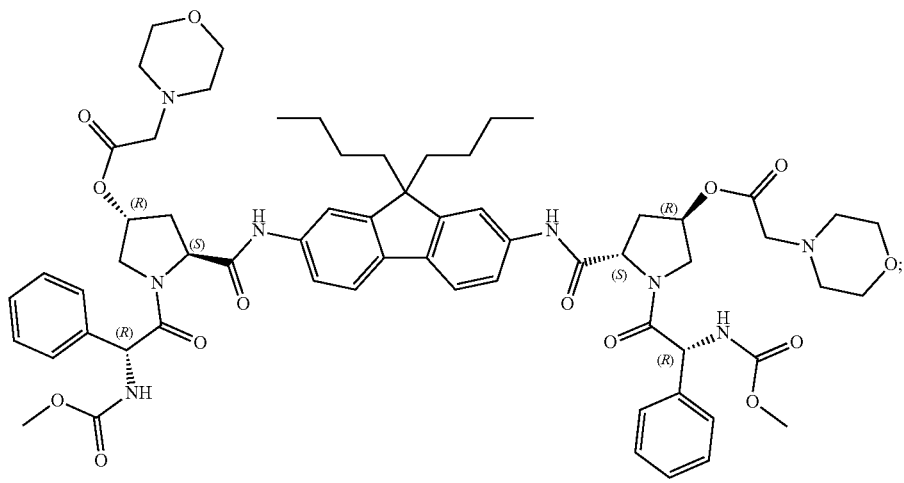
[Formula 1-34]
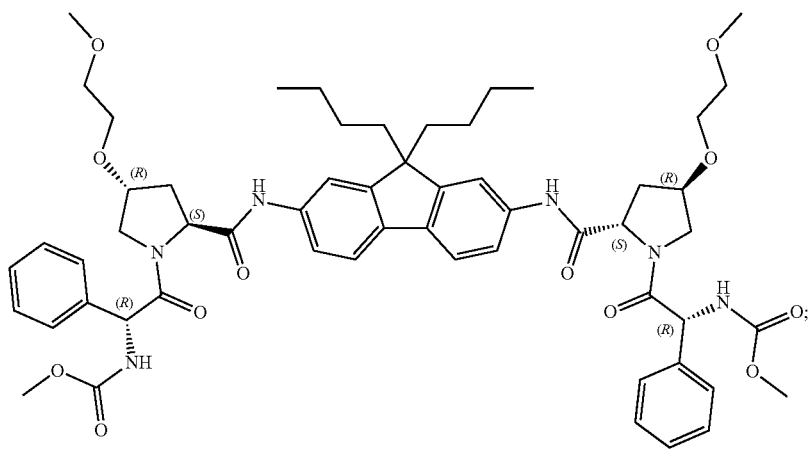
[Formula 1-35]
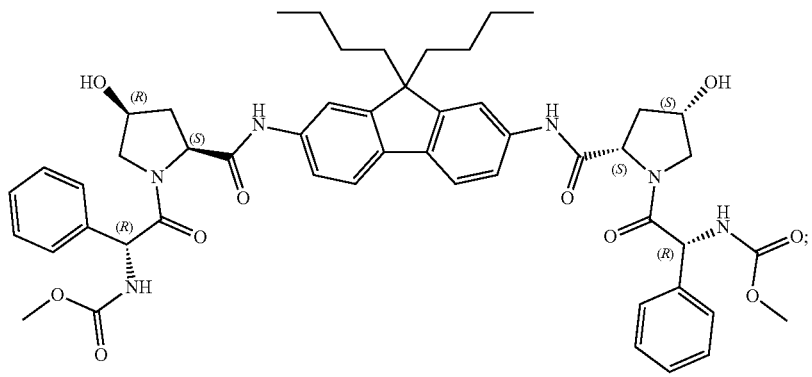
[Formula 1-36]
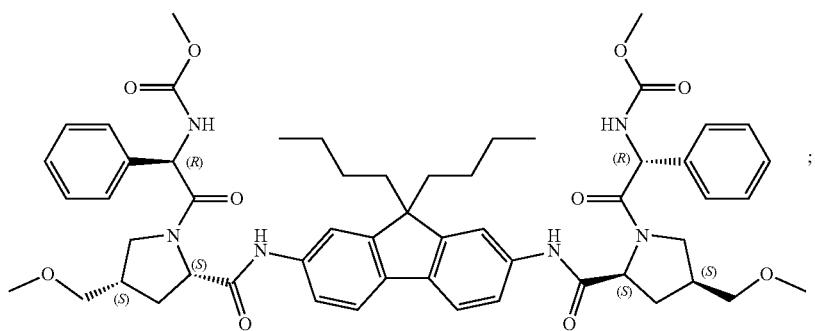

[Formula 1-37]
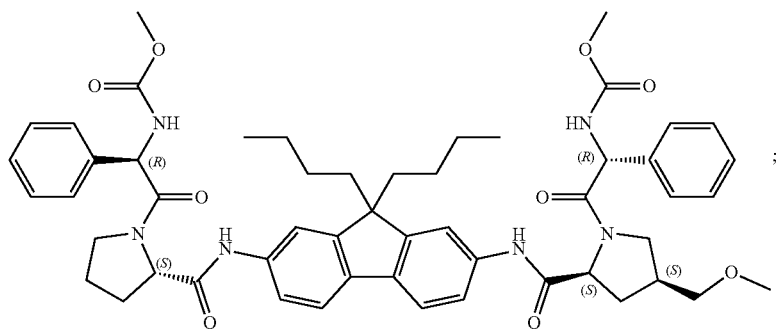
[Formula 1-38]
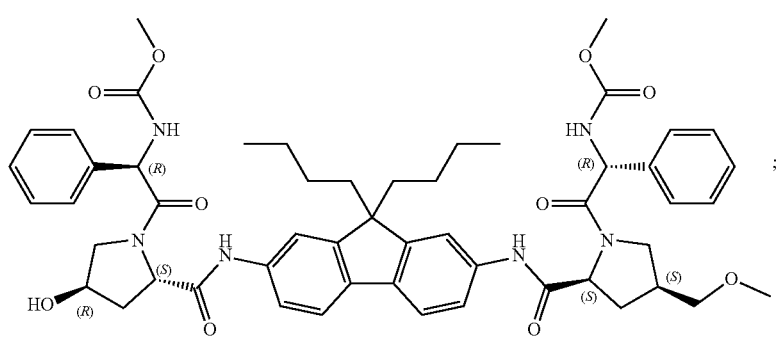
[Formula 1-39]
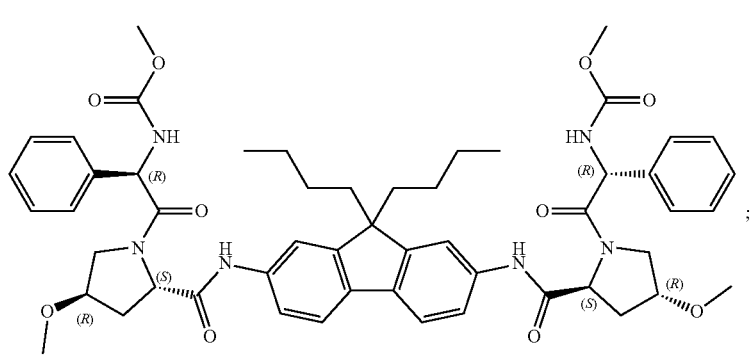
[Formula 1-40]
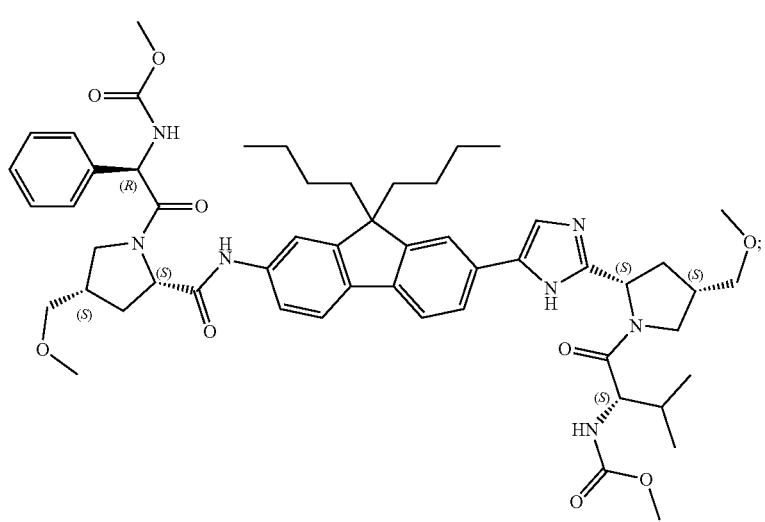

-continued

[Formula 1-41]

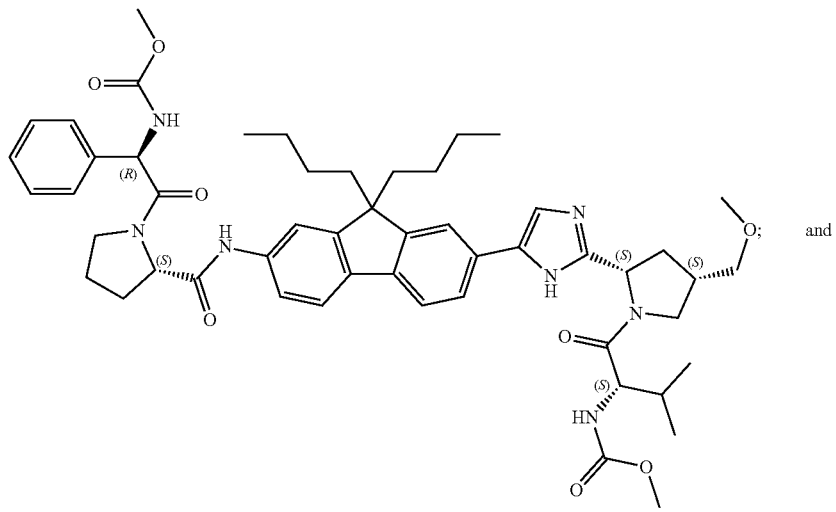

and

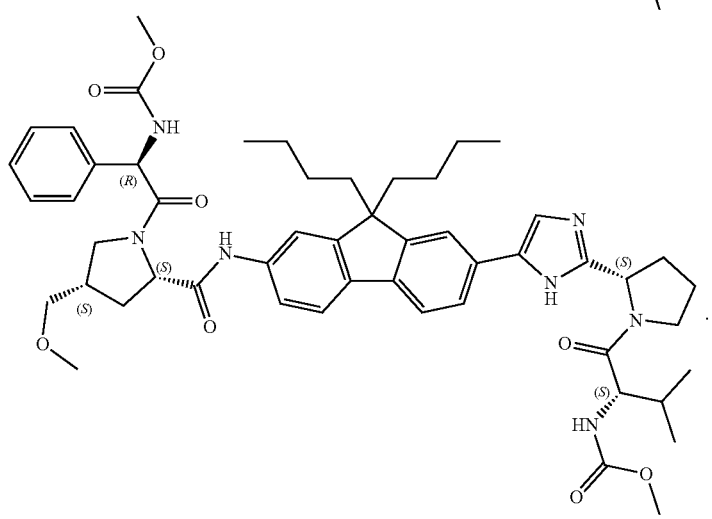

6. A method for preparation of a compound represented by formula 1 of claim 1 comprising the step of preparing the compound represented by formula 1 by reacting a compound represented by formula 2 with a compound represented by formula 3, as shown in reaction formula 1 below:

[Reaction Formula 1]

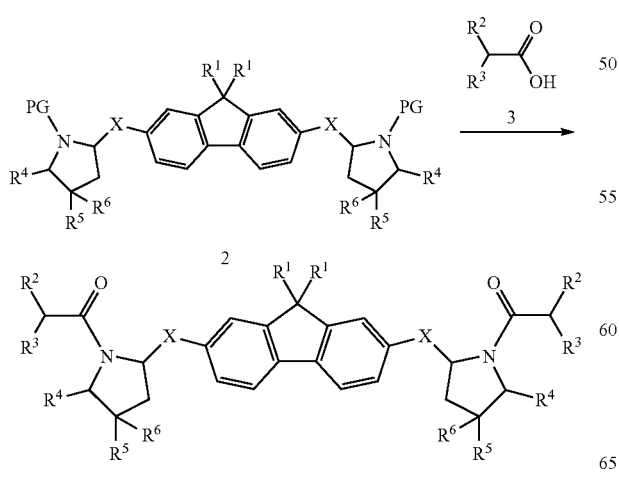

wherein $R^1$, $R^2$, $R^3$, $R^4$, $R^5$, $R^6$ and X are as defined in formula 1 of claim 1; and PG is an amine protecting group selected from the group consisting of t-butyloxycarbonyl (BOC), carbobenzyloxy (Cbz), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc) and aryloxycarbonyl (Alloc).

7. A method of treating a subject having a HCV-related liver disease, said method comprising administering an effective amount of compound represented by chemical formula 1 of claim 1, the optical isomer thereof or the pharmaceutically acceptable salt thereof as an active ingredient.

8. The method according to claim 7, wherein the compound exhibits an antiviral effect on HCV (hepatitis C virus) or HCV mutants.

9. The method according to claim 8, wherein the HCV mutant is L31V, Y93H or L31V+Y93H (double mutant).

10. The method according to claim 7, wherein the HCV-related liver disease is one or more diseases selected from the group consisting of acute hepatitis C, chronic hepatitis C, cirrhosis and hepatocellular carcinoma.

11. The method according to claim 7, wherein the HCV-related liver disease is caused by HCV mutation.

12. A health functional food composition for preventing or ameliorating HCV-related disease comprising the compound represented by formula 1 of claim 1, the optical isomer thereof or the pharmaceutically acceptable salt thereof as an active ingredient.

\* \* \* \* \*